United States Patent
Wittkowski

(10) Patent No.: US 11,103,473 B2
(45) Date of Patent: Aug. 31, 2021

(54) TREATMENT AND PREVENTION OF AUTISM AND AUTISM SPECTRUM DISORDERS

(71) Applicant: ASDERA LLC, New York, NY (US)

(72) Inventor: Knut M. Wittkowski, New York, NY (US)

(73) Assignee: Asdera LLC, New York, NY (US)

(*) Notice: Subject to any disclaimer, the term of this patent is extended or adjusted under 35 U.S.C. 154(b) by 0 days.

(21) Appl. No.: 14/916,665

(22) PCT Filed: Sep. 5, 2014

(86) PCT No.: PCT/US2014/054421
§ 371 (c)(1),
(2) Date: Mar. 4, 2016

(87) PCT Pub. No.: WO2015/035258
PCT Pub. Date: Mar. 12, 2015

(65) Prior Publication Data
US 2016/0206581 A1 Jul. 21, 2016

Related U.S. Application Data

(60) Provisional application No. 61/874,979, filed on Sep. 6, 2013, provisional application No. 61/911,998, filed (Continued)

(51) Int. Cl.
*A61K 47/48* (2006.01)
*A61K 31/195* (2006.01)
(Continued)

(52) U.S. Cl.
CPC .......... *A61K 31/196* (2013.01); *A61K 31/195* (2013.01); *A61K 31/197* (2013.01);
(Continued)

(58) Field of Classification Search
CPC ...... A61K 31/196; A61K 45/06; A61K 31/44; A61K 47/55; A61K 31/197; A61K 31/195; A61P 25/28; A61P 25/00
See application file for complete search history.

(56) References Cited

U.S. PATENT DOCUMENTS 7,932,294 B2   4/2011  Satyam
2011/0172188 A1  7/2011  Mouthon et al.

FOREIGN PATENT DOCUMENTS

CN   101704761 B   5/2010
EP   14841451.9    9/2014
(Continued)

OTHER PUBLICATIONS

Mazefsky, Variability in Adaptive Behavior in Autism: Evidence for the Importance of Family History, J. Abnorm. Child Psychol., 2008, 36, pp. 591-599.*
(Continued)

*Primary Examiner* — Savitha M Rao
*Assistant Examiner* — Andrew P Lee
(74) *Attorney, Agent, or Firm* — Ballard Spahr LLP

(57) ABSTRACT

In some embodiments, the present invention provides certain compositions and methods that may be useful in the treatment and/or prevention of a neurodevelopmental disorder, such as autism or an autism spectrum disorder (ASD). In some such embodiments, compositions are provided that contain at least one fenamate active agent, such as mefenamic acid, or an analogue or derivative thereof. In some embodiments, such compositions may also comprise an additional active agent, such as gabapentin, or an analogue or derivative thereof.

20 Claims, 20 Drawing Sheets

Related U.S. Application Data on Dec. 4, 2013, provisional application No. 61/919,501, filed on Dec. 20, 2013.

(51) Int. Cl.
| | |
|---|---|
| *A61K 31/196* | (2006.01) |
| *A61K 45/06* | (2006.01) |
| *A61K 31/44* | (2006.01) |
| *A61K 47/55* | (2017.01) |
| *A61K 31/197* | (2006.01) |

(52) U.S. Cl.
CPC .............. *A61K 31/44* (2013.01); *A61K 45/06* (2013.01); *A61K 47/55* (2017.08)

(56) References Cited

FOREIGN PATENT DOCUMENTS

| EP | 3041577 | 7/2016 | | |
|---|---|---|---|---|
| WO | WO 2013016696 | 1/2013 | | |
| WO | WO 2013016696 A1 * | 1/2013 | ............ | A61K 47/481 |
| WO | WO-2013/064579 A1 | 5/2013 | | |
| WO | WO 2013064579 A1 * | 5/2013 | ............. | A61K 45/06 |
| WO | WO-2013-163455 A2 | 10/2013 | | |
| WO | PCT/US2014/054421 | 9/2014 | | |
| WO | WO 2015/035258 | 3/2015 | | |

OTHER PUBLICATIONS

Mahdi, Design, Synthesis and Hydrolytic Behavior of Mutual Prodrugs of NSAIDs with Gabapentin Using Glycol Spacers, Pharmaceuticals, 2012, 5, pp. 1080-1091.*
Arbelaez LF, Bergmann U, et al. "Interaction of Matrix Metalloproteinases-2 and -9 with Pregnancy Zone Protein and α2-Macroglobulin", (1997) *Arch Biochem Biophys* 347:62-8.
Banerjee, et al: "Poly(ethylene glycol)-Prodrug Conjugates: Concept, Design, and Applications", Journal of Drug Delivery, vol. 2012 (2012), Article ID 103973, 17 pages, http://dx.doi.org/10.1155/2012/103973.
Berg J, Yang H, et al. (2012) *Journal of Cell Science* 125:1367-71.
Berx G, van Roy F (2009) *Cold Spring Harb Perspect Biol* 1:a003129.
Boonyaratanakornkit V, Scott MP, et al. (2001) *Mol Cell* 8:269-80.
Bosl W, Tierney A, et al. (2011) *BMC Medicine* 9:18.
Bouyain S, Watkins DJ (2010) *Proceedings of the National Academy of Sciences* 107:2443-8.
Brinton RD, Thompson RF, et al. (2008) *Front Neuroendocrinol* 29:313-39.
Champion GD, Graham GG "Pharmacokinetics of Non-Steroidal Anti-Inflammatory Agents", (1978) *Aust N Z J Med* 8 Suppl 1:94-100.
Chawarska K, Macari S, et al. (2013) *Biol Psychiatry* 74:195-203.
Chen Y, Wang F, et al. (2011) *J Cell Biol* 194:905-20.
Chetty C, Vanamala SK, et al. (2012) *Cell Signal* 24:549-59.
Christian SL, Brune CW, et al. (2008) *Biol Psychiatry* 63:1111-7; Table S2 AU018704.
Chung RH, Ma D, et al. (2011) *Mol Autism* 3:2.
Cichy J, Pure E (2003) *J Cell Biol* 161:839-43.
Cleveland WS, Devlin SJ (1988) *J Am Statist Assoc* 83:596-610.
Coyne et al: "Characterization of the interaction between fenamates and hippocampal neuron $GABA_A$ receptors", Neurochemistry International, Elsevier, Amsterdam, NL, vol. 51, No. 6-7,Oct. 5, 2007 (Oct. 5, 2007), pp. 440-446, XP022287613, ISSN: 0197-0186, 001: 10.1 016/J.NEUINT.2007.04.017.
Dawson: "Early behavioral intervention, brain plasticity, and the prevention of autism spectrum disorder", Development and Psychopathology 20 (2008), 775-803.
De Campos ML, Baldan-Cimatti HM, et al. (2012) *Drug Metab Lett* 6:235-41.
Deutsch CK, Joseph RM "Brief Report: Cognitive Correlates of Enlarged Head Circumference in Children with Autism", (2003) *J Autism Dev Disord* 33:209-15.
Elison JT, Paterson SJ, et al. (2013) *Am J Psychiatry* 170:899-908.
Elsabbagh M, Mercure E, et al. (2012) *Curr Biol* 22:338-42.
Fernandez M, Lao-Peregrin C, et al. (2010) *Epilepsia* 51:384-90.
Fisher RA (1948) *The American Statistician* 2:30.
Greenwood IA, Leblanc N "Overlapping pharmacology of Ca2+-activated CIS and K+ channels", (2007) *Trends Pharmacol Sci* 28:1-5.
Guglielmo Riccardo et al: "Managing disruptive and compulsive behaviors in adult with autistic disorder with gabapentin.", Journal of Clinical Psychopharmacology, Apr. 2013, vol. 33, No. 2, Apr. 2013 (Apr. 2013), pp. 273-274, XP008184730, ISSN: 1533-712X.
HapMap (2007) Nature 449:851-61.
Hildebrand JD, Soriano P (1999) *Cell* 99:485-97.
Hollingworth P, "Paediatric Rheumatology: Review the Use of Non-Steroidal Anti-Inflammatory Drugs in Paediatric Rheumatic Diseases", (1993) *Br J Rheumatol* 32:73-7.
Hu VW, Frank BC, et al. (2006) *BMC Genomics* 7:118.
Ito K, Niida Y, et al. "Pharmacokinetics of mefenamic acid in preterm infants with patent ductus arteriosus", (1994) *Acta Paediatr Jpn* 36:387-91.
Jain, et al.: "Mutual prodrugs containing bio-cleavable and drug releasable disulfide linkers", Bioorganic Chemistry, vol. 49, Aug. 2013, pp. 40-48.
Jilani JA, Pillai GK, et al. "Evaluation of Hydroxyethyl Esters of Mefenamic Acid and Diclofenac as Prodrugs", (1997) *Drug Dev Ind Pharm* 23:319-23.
Khan MS, Akhter M (2005) *Pharmazie* 60:110-4.
Kuhlenbaumer G, Hannibal MC, et al., "Mutations in SEPT9 cause hereditary neuralgic amyotrophy", (2005) *Nat Genet* 37:1044-6).
Kumar RA, Sudi J, et al. (2010) *J Med Genet* 47:81-90.
Kunzelmann K, Tian Y, et al., "Anoctamins", (2011) *Pflügers Archiv European Journal of Physiology* 462:195-208.
Kylliainen A, Hietanen JK (2006) *J Autism Dev Disord* 36:517-25.
Lainhart JE, Bigler ED, et al. (2006) *Am J Med Genet A* 140:2257-74.
Lane RF, St George-Hyslop P, et al. (2012) *J Neurosci* 32:14080-6.
Laumonnier F, Roger S, et al. (2006) *Am J Psychiatry* 163:1622-9.
Lemonnier et al: "A randomised controlled trial of bumetanide in the treatment of autism in children", Translational Psychiatry, vol. 2, No. 12, Dec. 1, 2012 (Dec. 1, 2012), p. e202, XP055056334, 001: 10.1 038/tp.2012.124.
Li C, Li M, et al. (2008) *Hum Hered* 65:129-41.
Losel R, Wehling M (2003) *Nat Rev Mol Cell Biol* 4:46-56.
McCaffery P, Deutsch CK (2005) *Prog Neurobiol* 77:38-56.
McGurk KA, Remmel RP, et al., "Reactivity of mefenamic acid 1-o-acyl glucuronide with proteins in vitro and ex vivo", (1996) *Drug Metab Dispos* 24:842-9.
Mikhael AN et al: "Synthesis of Some New Fenamic and Naphthalene Propionic Acid Esters of Pharmacological Activities", Egyptian Journal of Pharmaceutical Sciences, National Information and Documentation Centre (NIDOC), EG, vol. 33, No. 1/02, Jan. 1, 1992 (Jan. 1, 1992), pp. 149-166, XP000578258, ISSN: 0301-5068.
Ng TM, Konopka E, et al., "Comparison of Bumetanide- and Metolazone-Based Diuretic Regimens to Furosemide in Acute Heart Failure", (2013) *J Cardiovasc Pharmacol Ther* 18:345-53.
Ohlan S, Nanda S, et al. (2013) *Med Chem Res* 22:5120-8.
Ozonoff S, Williams BJ, et al., "Parental report of the early development of children with regressive autism the delays-plus-regression phenotype", (2005) Autism 9:461-86.
Pearson TA, Manolio TA (2008) *JAMA* 299:1335-44.
Peng ST, Su CH, et al. (2007) *Int J Oncol* 31:1119-26.
Peretz A, Degani-Katzav N, et al. (2007) *PLoS One* 2:e1332.
Pinto D, Pagnamenta AT, et al. (2010) *Nature* 466:368-72.
Prasad Durga et al: "Synthesis of Prodrugs of Mefenamic Acid and Their In Vivo Evaluation", International Journal of Pharmacy and Pharmaceutical Sciences, vol. 6, No. 7, Jul. 29, 2014 (Jul. 29, 2014), pp. 437-442, XP055376658.
Pringsheim T, Davenport WJ, et al., "Acute treatment and prevention of menstrually related migraine headache: Evidence-based review", (2008) *Neurology* 70:1555-63.

(56) References Cited

OTHER PUBLICATIONS

Public Assessment Report for paediatric studies submitted in accordance with Article 45 of Regulation (EC) No. 1901/2006, as amended; Mefenamic Acid; UK/W/037/pdWS/001 (Sep. 17, 2012).
Richler J, Luyster R, et al. (2006) J Autism Dev Disord 36:299-316.
Robison AJ, Bass MA, et al. (2005) *J Biol Chem* 280:35329-36.
Rutter M, Andersen-Wood L, et al. (1999) *J Child Psychol Psychiatry* 40:537-49.
Sanders Stephan J, Ercan-Sencicek AG, et al. (2011) *Neuron* 70:863-85.
Sato J, Kudo N, et al. (1997) *Biol Pharmacol Bull* 20:443-5.
Schluth-Bolard C, Labalme A, et al. (2013) *J Med Genet* 50:144-50.
Schork AJ, Thompson WK, et al. (2013) *PLoS Genet* 9:e1003449.
Shah K, Shrivastava S, et al. (2013) *Med Chem Res* 22:70-7.
Shah K, Shrivastava SK, et al. (2014) *Pak J Pharm Sci* 27:917-23.
Shimoda Y, Watanabe K (2009) *Cell Adh Migr* 3:64-70.
Smoller, et al.: "Identification of risk loci with shared effects on five major psychiatric disorders: a genome-wide analysis." Lancet (London, England), ISSN: 1474-547X, vol. 381, Issue: 9875, p. 1371-9, Publication Year: 2013.
Splawski, et al: "CaV1.2 Calcium Channel Dysfunction Causes a Multisystem Disorder Including Arrhythmia and Autism", Cell, vol. 119, Issue 1, p. 19-31, Oct. 1, 2004.
Srivastava DP, Woolfrey KM, et al. (2012) *PLoS Biol* 10:e1001350.
Takagi T, Jin W, et al. (2006) *Brain Res* 1108:88-97.
Takeuchi T, Misaki A, et al. (2000) *J Neurochem* 74:1489-97.
Tall AR, Mistilis SP (1975) *J Int Med Res* 3:176-82.
Teng KK, Felice S, et al. (2010) *Developmental Neurobiology* 70:350-9.
Thomas P, Pang Y (2012) *Neuroendocrinology* 96:162-71.
Tonks NK (2006) *Nat Rev Mol Cell Biol* 7:833-46.
Valnegri P, Montrasio C, et al. (2011) *Hum Mol Genet* 20:4797-809.
Velingkar VS, Desai DM, et al. (2011) *Int J Drug Design Discovery* 2:548-58.
Venuti MC, Young JM, et al. (1989) *Pharm Res* 6:867-73.
Verkman AS, Galietta LJV (2009) *Nat Rev Drug Discov* 8:153-71.
Wang Z, Shen D, et al. (2004) *Science* 304:1164-6.
Wang K, Zhang H, et al. (2009) *Nature* 459:528-33.
Wei X, Walia V, et al. (2011) *Nat Genet* 43:442-6.
Winder CV, Wax J, et al. (1962) *J Pharmacol Exp Ther* 138:405-13.
Winder CV, Kaump DH, et al. (1966) *Rheumatology* VIII:7-49.
Wittkowski KM (1988) *J Am Statist Assoc* 83:1163-70, 87:258.
Wittkowski et al: "A novel computational biostatistics approach implies impaired dephosphorylation of growth factor receptors as associated with severity of autism", Translational Psychiatry, vol. 4, No. 1, Jan. 28, 2014 (Jan. 28, 2014), p. e354, XP055376737, 001: 10.1 038/tp.2013.124.
Wu JY, Kuban KC, et al. (2005) *J Child Neurol* 20:790-5.
Yau HJ, Baranauskas G, et al. (2010) *J Physiol* 588:3869-82.
Yoshimura Y, Kikuchi M, et al. (2013) *PLoS One* 8:e80126.
Zöller M (2011) *Nat Rev Cancer* 11:254-67.
Zou H, Yu Y, et al. (2011) Genes Brain Behav 10:615-24.
Zuko A, Bouyain S, et al. (2011) *Adv Protein Chem Struct Biol* 84:143-80.
PCT International Search Report from Priority application PCT/US2014-054421 dated Dec. 22, 2014.
EP Supplementary Search Report from related application EP14841451.9 dated May 30, 2017.
Communication pursuant to Article 94(3) EPC was dated Jun. 19, 2019 by the European Patent Office for EP Application No. 14841451.9, filed on Sep. 5, 2014 and published as EP 3041577 on Jul. 13, 2016 (Applicant—Wittkowski) (11 pages).
Zhiyu, et al. (2016) "The Inflammasome: an Emerging Therapeutic Oncotarget for Cancer Prevention," Oncotarget 7(31): 50766.
International Preliminary Report on Patentability dated Mar. 8, 2016 by the International Searching Authority for International Application No. PCT/US2014/054421, filed on Sep. 5, 2013 and published as WO/2015/035258 on Mar. 12, 2015 (Applicant—The Rockefeller University) (9 Pages).
U.S. Appl. No. 61/874,979, filed Sep. 6, 2013, Knut Wittkowski.
U.S. Appl. No. 61/911,998, filed Dec. 4, 2013, Knut Wittkowski.
U.S. Appl. No. 61/919,501, filed Dec. 20, 2013, Knut Wittkowski.

\* cited by examiner

AGP II: Ras Pathway

TREATMENT AND PREVENTION OF AUTISM AND AUTISM SPECTRUM DISORDERS

CROSS-REFERENCE TO RELATED APPLICATIONS

This application is a U.S. National Stage entry under 35 U.S.C. § 371 of International Patent Application No. PCT/US2014/054421, filed Sep. 5, 2014, which claims the benefit of priority of U.S. Provisional Patent Application No. 61/874,979, filed Sep. 6, 2013, U.S. Provisional Patent Application No. 61/911,998, filed Dec. 4, 2013, and U.S. Provisional Patent Application No. 61/919,501, filed Dec. 20, 2013, the contents of each of which are hereby incorporated by reference.

STATEMENT REGARDING FEDERALLY SPONSORED RESEARCH

This invention was made with government support under grant number UL1 RR024143 awarded by the U.S. National Center for Research Resources (NCRR), grant number UL1 TR000043 awarded by the U.S. National Center for Research Resources and the National Center for Advancing Translational Sciences (NCATS), and grant number UL1 TR000038 awarded by the U.S. National Center for Advancing Translational Sciences (NCATS). The government has certain rights in the invention.

COPYRIGHT AND INCORPORATION BY REFERENCE

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

For the purposes of those jurisdictions that permit incorporation by reference, the text of all documents cited herein is hereby incorporated by reference in its entirety.

BACKGROUND

Autism and Autism Spectrum Disorders (ASDs) include a broad range of developmental brain disorders that share a complex and heterogeneous etiology characterized by fundamental deficits in social reciprocity, impaired language and communication skills, as well as repetitive and stereotypic behavior. About 1% of the population are directly affected and many more as family members.

Every year, about 20,000 children develop symptoms of ASDs in the U.S. alone. About 50% of them experience loss of previously acquired social behaviors or communication skills (regression) (Ozonoff S, Williams B J, et al. (2005) *Autism* 9:461-86; Richler J, Luyster R, et al. (2006) *J Autism Dev Disord* 36:299-316), yet the currently available pharmacological interventions address only the symptoms of autism, at best, and do not address the underlying disease or its progression. The few drugs approved for treatment of autism merely address irritability associated with autism. There is currently no approved pharmacological intervention to prevent regression to more severe forms of autism and ASDs. A child developing a life-long disability poses an approximately $10M burden on society in terms of lost income for the patient and often one of the parents as well as direct cost for treatment and assisted living. Multiplied by 20,000 children per year in need for life-long assistance in the U.S. alone, the lack of adequate treatment costs society an estimated $200B per year. More importantly, the social and emotional consequences of a life-long disability on the patient and his or her family are significant and immeasurable.

There is a need for a better understanding of the genetic risk factors underlying autism and ASDs. Such findings and genetic analyses can be useful for defining drug targets, and developing therapeutic compounds and treatment methods which target the mechanisms underlying autism and ASDs, so that, instead of only treating symptoms, therapeutic approaches for autism and ASDs can be developed to prevent the onset of disease, delay the progression of disease, and/or cure the disease.

SUMMARY OF THE INVENTION

Some of the main aspects of the present invention are summarized below. Additional aspects of the present invention are described in the Detailed Description of the Invention, Examples, Drawings and Claims sections of this patent application. The description in each of the sections of this patent application is intended to be read in conjunction with the other sections. Furthermore, the various embodiments described in each of the sections of this patent application can combined in various different ways, and all such combinations are intended to fall within the scope of the present invention.

In one aspect, the present invention provides a method of treating autism or an ASD in a subject, the method comprising administering to the subject an effective amount of a fenamate, or an analogue or derivative thereof, either alone or in combination with one or more additional active agents. For example, in one embodiment, the present invention provides a method of treating autism or an ASD in a subject, the method comprising administering to the subject an effective amount of the fenamate mefenamic acid (MFA), or an analogue or derivative thereof, either alone or in combination with one or more additional active agents. In one embodiment, such an additional active agent may be a calcium channel modulator, such as gabapentin, or an analogue or derivative thereof. In one embodiment the present invention provides a method of treating autism or an ASD in a subject, the method comprising administering to the subject an effective amount of MFA or an MFA prodrug in combination with an effective amount of gabapentin or a gabapentin prodrug. In some such embodiments the MFA and the gabapentin are comprised within the same prodrug molecule. In some such embodiments the MFA and the gabapentin are comprised within the same prodrug molecule.

In one aspect, the present invention provides a method of improving one or more indicators or symptoms of autism or an ASD in a subject, the method comprising administering to a subject exhibiting one or more indicators or symptoms of autism or an ASD, an effective amount of a fenamate, or an analogue or derivative thereof, either alone or in combination with one or more additional active agents, wherein the indicator is selected from the group consisting of abnormal behavior, abnormal eye tracking response, abnormal skin conductance response, abnormal electroencephalography (EEG) response, and/or abnormal magnetoencephalography (MEG) response. In one embodiment, the "improving" comprises an increase of at least 1% in a measurement of the one or more indicators or symptoms. For example, in one embodiment, the present invention provides a method of improving one or more indicators or symptoms of autism or an ASD in a subject, the method comprising administering to a subject exhibiting one or more indicators or symptoms of autism or an ASD an effective amount of the fenamate MFA, or an analogue or derivative thereof, either alone or in combination with one or more additional active agents. In one embodiment, such an additional active agent may be a calcium channel modulator, such as gabapentin, or an analogue or derivative thereof. In one embodiment the present invention provides a method of improving one or more indicators or symptoms of autism or an ASD in a subject, the method comprising administering to a subject exhibiting one or more indicators or symptoms of autism or an ASD, an effective amount of MFA or an MFA prodrug in combination with an effective amount of gabapentin or a gabapentin prodrug.

In some embodiments, the fenamate used in the various methods and compositions described herein is selected from the group consisting of fenamic acid, mefenamic acid (MFA), tolfenamic acid (TFA), flufenamic acid (FFA), meclofenamic acid (CFA), and analogues and derivatives thereof. In some embodiments, the fenamate is MFA. In some embodiments, the fenamate, such as MFA, is administered to the subject at a dose of about 1 mg to about 500 mg per day. In some embodiments, the fenamate, such as MFA, is administered to the subject at a dose of about 25 mg to about 75 mg per day. In some embodiments, the fenamate, such as MFA, is administered to the subject at a dose of at least 0.1 mg, at least 0.5 mg, at least 1 mg, at least 5 mg, at least 10 mg, at least 20 mg, at least 30 mg, at least 40 mg, at least 50 mg, at least 75 mg, at least 100 mg, or at least 200 mg per day. In some embodiments, the fenamate, such as MFA, is administered to the subject at a dose in the range of 1 to 1000 mg, 1 to 750 mg, 1 to 500 mg, 1 to 250 mg, 1 to 100 mg, 1 to 50 mg, 1 to 25 mg, 25 to 1000 mg, 25 to 500 mg, 25 to 100 mg, 25 to 75 mg or 25 to 50 mg per day. In some such embodiments, each of the dosages described above is mg/kg/day. Additional dosages that may be used are provided in the Detailed Description section of this patent application.

In some embodiments, the present invention comprises administering to a subject one or more active agents selected from the group consisting of potassium channel modulators, chloride channel modulators (including CaCCs), and calcium channel modulators. In some embodiments, the present invention comprises administering to a subject both a fenamate, or an analogue or derivative thereof, and one or more additional active agents selected from the group consisting of potassium channel modulators, chloride channel modulators (including CaCCs), and calcium channel modulators. In some embodiments, the present invention comprises administering to a subject both a fenamate, or an analogue or derivative thereof, and an additional active agent that is a potassium channel modulator. In some embodiments, the present invention comprises administering to a subject both a fenamate, or an analogue or derivative thereof, and an additional active agent that is a chloride channel modulator (such as a CaCC modulator). In some embodiments, the present invention comprises administering to a subject both a fenamate, or an analogue or derivative thereof, and an additional active agent that is a calcium channel modulator. In some embodiments, the present invention comprises administering to a subject both a fenamate, or an analogue or derivative thereof, and two or more additional active agents selected from the group consisting of calcium channel modulators, chloride channel modulators, and potassium channel modulators. In some embodiments, where calcium channel modulators are used, the calcium channel modulator may be selected from the group consisting of gabapentin, pregabalin, or atagabalin, or an analogue or derivative thereof.

In some embodiments the present invention provides a method of treating a neurodevelopmental disease or disorder, such as autism or an ASD, in a subject, the method comprising administering to the subject an effective amount of a chloride channel modulator. In some embodiments the present invention provides a method of treating a neurodevelopmental disease or disorder, such as autism or an ASD, in a subject, the method comprising administering to the subject an effective amount of a CaCC modulator. In some embodiments the present invention provides a method of treating a neurodevelopmental disease or disorder, such as autism or an ASD, in a subject, the method comprising administering to the subject an effective amount of a calcium channel modulator. In some embodiments, the present invention provides a method of treating a neurodevelopmental disease or disorder, such as autism or an ASD in a subject, the method comprising administering to the subject an effective amount of a potassium channel modulator. In some embodiments the present invention provides a method of treating a neurodevelopmental disease or disorder, such as autism or an ASD, in a subject, the method comprising administering to the subject an effective amount of both a chloride channel modulator and a potassium channel modulator. In some embodiments the present invention provides a method of treating a neurodevelopmental disease or disorder, such as autism or an ASD, in a subject, the method comprising administering to the subject an effective amount of a chloride channel modulator, a potassium channel modulator, and a calcium channel modulator.

In some embodiments, where CaCC modulators are used, the CaCC modulator is a modulator of an anoctamin CaCC. In some such embodiments, the CaCC modulator is a modulator of an ANO1, ANO2, ANO3, ANO4, ANO5, ANO6, ANO7, ANO8, ANO9, or ANO10 anoctamin CaCC. In some embodiments, the CaCC modulator is a fenamate, or an analogue or derivative thereof. In some embodiments, the CaCC modulator is selected from the group consisting of fenamic acid, MFA, TFA, FFA, NFA and CFA, and analogues and derivatives thereof. In some embodiments, the CaCC modulator is MFA or an analog or derivative thereof, and is administered to the subject at a dose of about 25 mg/kg/day to about 75 mg/kg/day, or one or the other dosages or dosage ranges described above and/or in the Detailed Description section of this patent application.

In some embodiments, the potassium channel modulator is a fenamate, or an analogue or derivative thereof. In some embodiments, the potassium channel modulator is selected from the group consisting of fenamic acid, MFA, TFA, FFA, NFA and CFA, and analogues and derivatives thereof. In some embodiments, the potassium channel modulator is MFA or an analog or derivative thereof, and is administered to the subject at a dose of about 25 mg/kg/day to about 75 mg/kg/day, or one or the other dosages or dosage ranges described above and/or in the Detailed Description section of this patent application.

In some embodiments, the methods of the invention further comprise administering to the subject a voltage-activated $Ca^{2+}$ channel modulator—in addition to a chloride channel and/or potassium channel modulator as described above (such as a fenamate). In one embodiment, the voltage-operated calcium channel (VOCC) modulator is gabapentin, pregabalin, or atagabalin, or an analogue or derivative thereof. Thus in one embodiment the present invention provides, a method of treating a neurodevelopmental disease or disorder, such as autism or an ASD in a subject, the method comprising administering to the subject an effective amount of gabapentin, pregabalin, or atagabalin, or an analogue or derivative thereof.

In some embodiments, the subjects treated according to the methods described herein, or treated using the compositions described herein, are human. In some embodiments, the subject may be a human child of any age, including a newborn. In another embodiment, the subject may be a human child of at least 1 month, 2 months, 3 months, 4 months, 5 months, 6 months, 9 months, or 12 months in age. In another embodiment, the subject is a human child of less than about 36 months (3 years) in age. In another embodiment, the subject is a human child of less than about 24 months (2 years) in age. Additional age ranges of the subjects of the invention are provided in the Detailed Description section of the patent application.

In some embodiments, the subjects treated according to the methods described herein, or treated using the compositions described herein, exhibit one or more clinical indicators or symptoms of autism or an ASD. In other embodiments, the subjects do not exhibit one or more clinical indicators or symptoms of autism or an ASD and the treatment methods are prophylactic treatment methods. In some embodiments, the subjects have been identified as being at risk of developing autism or an ASD, for example as the result of a family history of autism or an ASD or as the result of genetic testing, for example for a mutation believed to be associated with autism or an ASD. In some embodiments, the subject has a family history of autism. In some embodiments, the subject has one or more genetic risk factors associated with autism and/or ASDs. In some embodiments, the subject has a mutation in an anoctamin CaCC. In some embodiments, the subject has a mutation in an ANO1, ANO2, ANO3, ANO4, ANO5, ANO6, ANO7, ANO8, ANO9, or ANO10 anoctamin CaCC. In some embodiments, the subject has a mutation in a VOCC gene, such including, but not limited to the CACNA1A, CACNA1C, and CACNA2D4 genes. In some embodiments, the subject has a mutation in a receptor protein tyrosine phosphatase (PTPR). In some embodiments, the methods of the present invention comprise conducting genetic testing on a subject, or obtaining genetic testing results of a subject, in order to determine if a subject is at risk of developing autism or an ASD. In some such embodiments, such genetic testing may be performed, or such genetic testing results may be obtained, prior to initiating treatment of the subject using any of the methods and/or compositions provided herein, and/or in order to determine whether the subject is a candidate for treatment using any of the methods and/or compositions provided herein.

In some embodiments the present invention provides various compositions, including pharmaceutical compositions. In some embodiments such compositions can be used in conjunction with the methods of treatment provided herein. For example, in one embodiment, the present invention provides compositions, such as pharmaceutical compositions, comprising any one or more of the active agents described herein, either alone or in combination, for example for use in treating autism or an ASD. In some embodiments, the present invention provides compositions comprising a fenamate, or an analogue or derivative thereof, for example for use in treating autism or an ASD. In some embodiments, the present invention provides compositions comprising gabapentin, pregabalin, or atagabalin, or an analogue or derivative thereof, for example for use in treating autism or an ASD. In some embodiments, the present invention provides compositions comprising both a fenamate, or an analogue or derivative thereof, and a calcium channel modulator, such as gabapentin, pregabalin, or atagabalin, or an analogue or derivative thereof, for example for use in treating autism or an ASD. A non-limiting example of such a composition is one comprising MFA and gabapentin. Another non-limiting example of such a pharmaceutical composition is one comprising MFA, or an analogue or derivative thereof, and gabapentin, or an analogue or derivative thereof. Another non-limiting example of such a composition is one comprising an MFA prodrug and a gabapentin prodrug. Another non-limiting example of such a composition is one comprising a MFA prodrug and gabapentin. Another non-limiting example of such a composition is one comprising MFA and a gabapentin prodrug. In some embodiments the present invention provides compositions comprising any one of the active agents described herein (such as a fenamate), or an analogue or derivative thereof (such as a prodrug derivative) together with any other agent known to, believed to, or being tested for its ability to, alleviate one or more symptoms of autism or an ASD. In some such embodiments, the compositions described herein comprise an effective amount of the active agent(s).

In another aspect, the invention provides a composition comprising a fenamate, or an analogue or derivative thereof, either alone or in combination with one or more additional active agents, for use in the treatment of a neurodevelopmental disease or disorder, such as autism or an ASD. In another aspect, the invention provides a composition comprising mefenamic acid (MFA), or an analogue or derivative thereof, either alone or in combination with one or more additional active agents, for use in the treatment of a neurodevelopmental disorder, such as autism or an ASD.

In another aspect, the invention provides a composition comprising a fenamate, or an analogue or derivative thereof, either alone or in combination with one or more additional active agents, for use in improving one or more indicators of autism or an ASD in a subject. In another aspect, the invention provides a composition comprising MFA, or an analogue or derivative thereof, either alone or in combination with one or more additional active agents, for use in improving one or more indicators of autism or an ASD in a subject.

In addition to all of the classes of molecules and specific molecules described herein as potential active agents, derivatives and analogues of such molecules/agents can be used in the compositions and methods of the present invention. Derivatives of the molecules/agents described herein that can be used in accordance with the compositions and methods of the present invention include, but are not limited to, prodrug derivatives. In some embodiments such prodrug derivatives may comprise polyethylene glycol molecules that have been covalently attached to the drug molecule (i.e. pegylated derivatives). In some embodiments such prodrugs may comprise, for example, two (or more) active agent molecules connected together, either directly or by a linker (or linkers) that can be degraded inside the body, such as a disulfide linker, palmityl linker, stearyl linker, glycol linker, polyethylene glycol linker, or ester linker. In some embodiments such prodrugs may comprise two (or more) of the same active agent molecule, such as two MFA molecules connected together, either directly or by a linker such as a disulfide linker, palmityl linker, stearyl linker, glycol linker, polyethylene glycol linker, or ester linker. In some embodiments such prodrugs may comprise two (or more) different active agent molecules, such as an MFA molecule and a gabapentin molecule, connected together, either directly or by a linker such as a disulfide linker, palmityl linker, stearyl linker, glycol linker, polyethylene glycol linker, or ester linker. In some embodiments such prodrugs may comprise an active agent molecule and any another suitable molecule, moiety, or chemical group (whether an active agent or not) that can be cleaved or removed from the prodrug to release the active agent molecule.

In some embodiments the present invention provides certain MFA prodrug molecules, such as those shown in FIG. 7. For example in one embodiment the present invention provides a novel MFA prodrug having the structure illustrated in FIG. 7A, 7B, or 7C, or analogues or derivatives thereof. In some embodiments the present invention also provides compositions, such as pharmaceutical compositions, comprising the MFA prodrugs illustrated in FIG. 7, or analogues or derivative thereof. In one embodiment, the MFA prodrugs illustrated in FIG. 7, or analogues or derivatives thereof, may be used to treat autism or an ASD as described herein. In some embodiments, the MFA prodrugs illustrated in FIG. 7 (such as that shown in FIG. 7A), or analogues or derivatives thereof, maybe used in any method or situation in which MFA can be used—i.e. not limited to treatment of autism and ASDs.

BRIEF DESCRIPTION OF THE DRAWINGS

FIG. 1A and FIG. 1B: AGP I; FIG. 1C and FIG. 1D: AGP II. FIG. 1A and FIG. 1C contain ssGWAS results (lower curve) for comparison with μGWAS results (upper curve). Each data point (open dots) represents the most significant result among all diplotypes centered at the same SNP ranked by significance (low to high). Dashed curve: linear (QQ plot) or loess (QR plot) projection. Solid curve: loess estimation. Vertical lines connect the most significant s-values ($s=-\log_{10} p$) of a gene (dot) with its expected value (solid line). Dotted vertical lines indicate genes with unknown function and results with low reliability (either low μIC or reliance on a single SNP), respectively. Genes with unknown function are excluded from the gene lists (shown with genes ranked by significance, bottom to top). Genes annotated with three to one stars are those among the top 20, 50, and 100 genes by significance that are also included in FIG. 2C and FIG. 2D (AGP I) or FIG. 2E and FIG. 2F (AGP II). Full and open triangles mark genes with an identical match or family member in SFARI Gene, respectively (see Figure FIG. 2A and FIG. 2B for details). The dotted horizontal lines represent the projected whole genome (WG) apex (6.272 and 6.064) and exploratory 100 gene cutoffs (4.835 and 4.480, graph only). The horizontal solid line indicates the proposed study-specific significance level.

FIG. 2A and FIG. 2B: Genes included in SFARI Gene are highlighted with a thicker border. Genes previously implicated in GWAS are highlighted with a double border. See TABLE 3 for details on pathway related genes among the top 20, 50, and 100 and genes included in SFARI Gene (ASD). Small letters "n" and "x" as part of the gene name indicate gene groups with several members varying by a number or a character, respectively. Upon growth factor (GF) binding to cell-surface receptors (e.g., IGFR, MET, PDGFR, ERBBn), formation of receptor complexes initiates proliferation, cytoskeletal organization, and survival along Ras down-stream effectors. GFs are immediately deactivated by PTPRs. The downstream activities are modulated by agonists binding to G-protein-coupled receptors (GPCR) activating phospholipase C (PLC) to form membrane diacylglycerol (DAG) and inositol trisphosphate (IP3). While DAG activates Ras directly, IP3 stimulates the release of $Ca^{2+}$ from the endoplasmic reticulum (ER), starting a process of $Ca^{2+}$ dependent activation of Ras involving several feedback loops. The fall in the concentration of $Ca^{2+}$ in internal stores leads, via STIM1, to the opening of store-operated $Ca^{2+}$ channels (SOCC) in the plasma membrane. ITPKB phosphorylates IP3 to IP4, which opens VOCCs. CaCCs can either be directly activated by $Ca^{2+}$ elevation or through $Ca^{2+}$/calmodulin kinase II (CaM-KII)-mediated phosphorylation. Other plasma membrane ion channels involved are $Ca^{2+}$ channels operated by NMDA and kainate ligands, voltage-operated potassium channels (VOPC), and ligand-operated CF channels (GABA). Overall $Ca^{2+}$ levels are limited by plasma-membrane $Ca^{2+}$ ATPase (PMCA).

FIG. 7. Mutual prodrugs.

DETAILED DESCRIPTION OF THE INVENTION

Figure 1A:
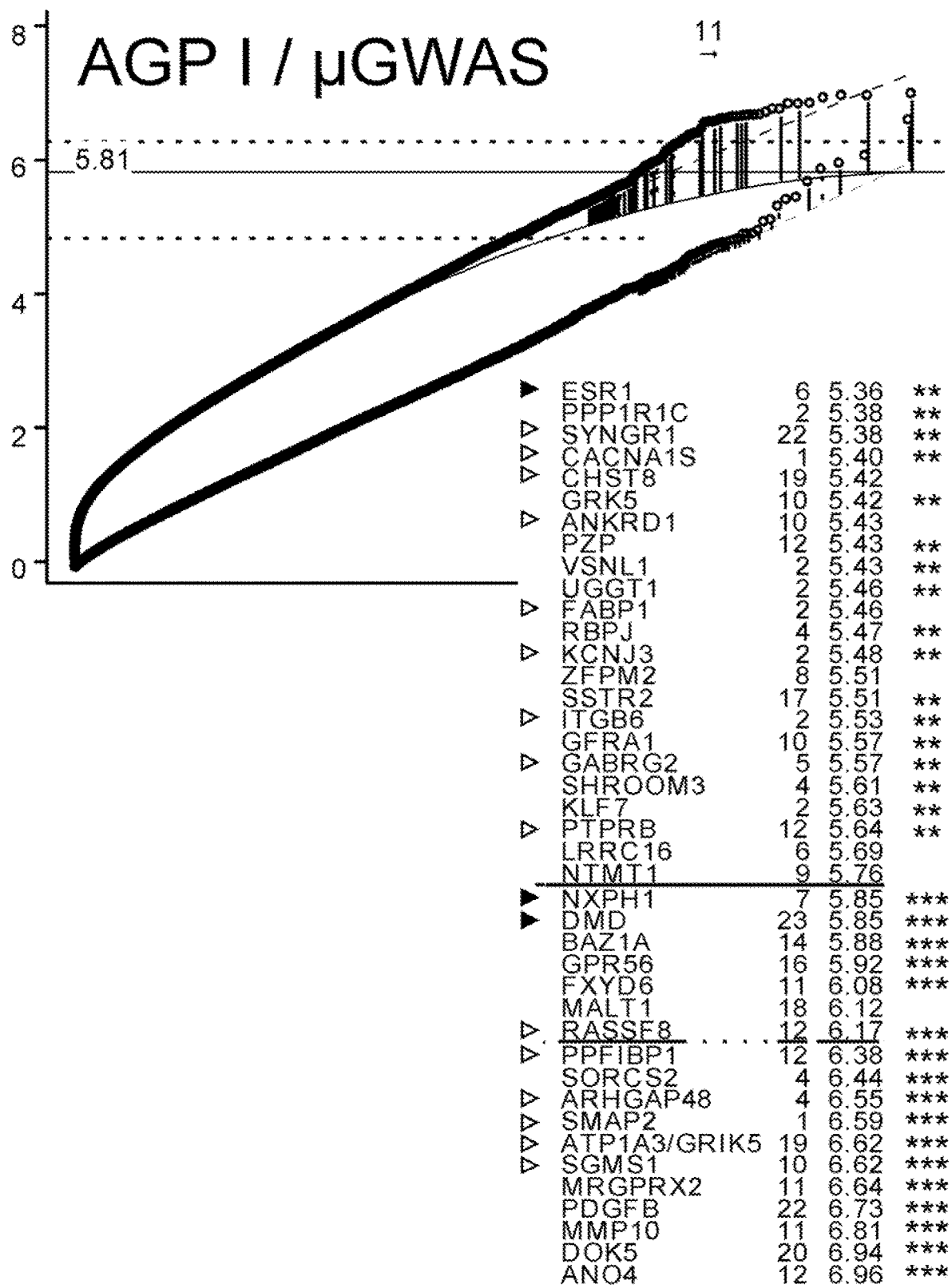
FIG. 1A-FIG. 1D: μGWAS QR (quantile-rank) vs. traditional ssGWAS QQ plots of analyses of data from the Autism Genome Project (AGP) with lists of most significant genes.
Figure 1B:
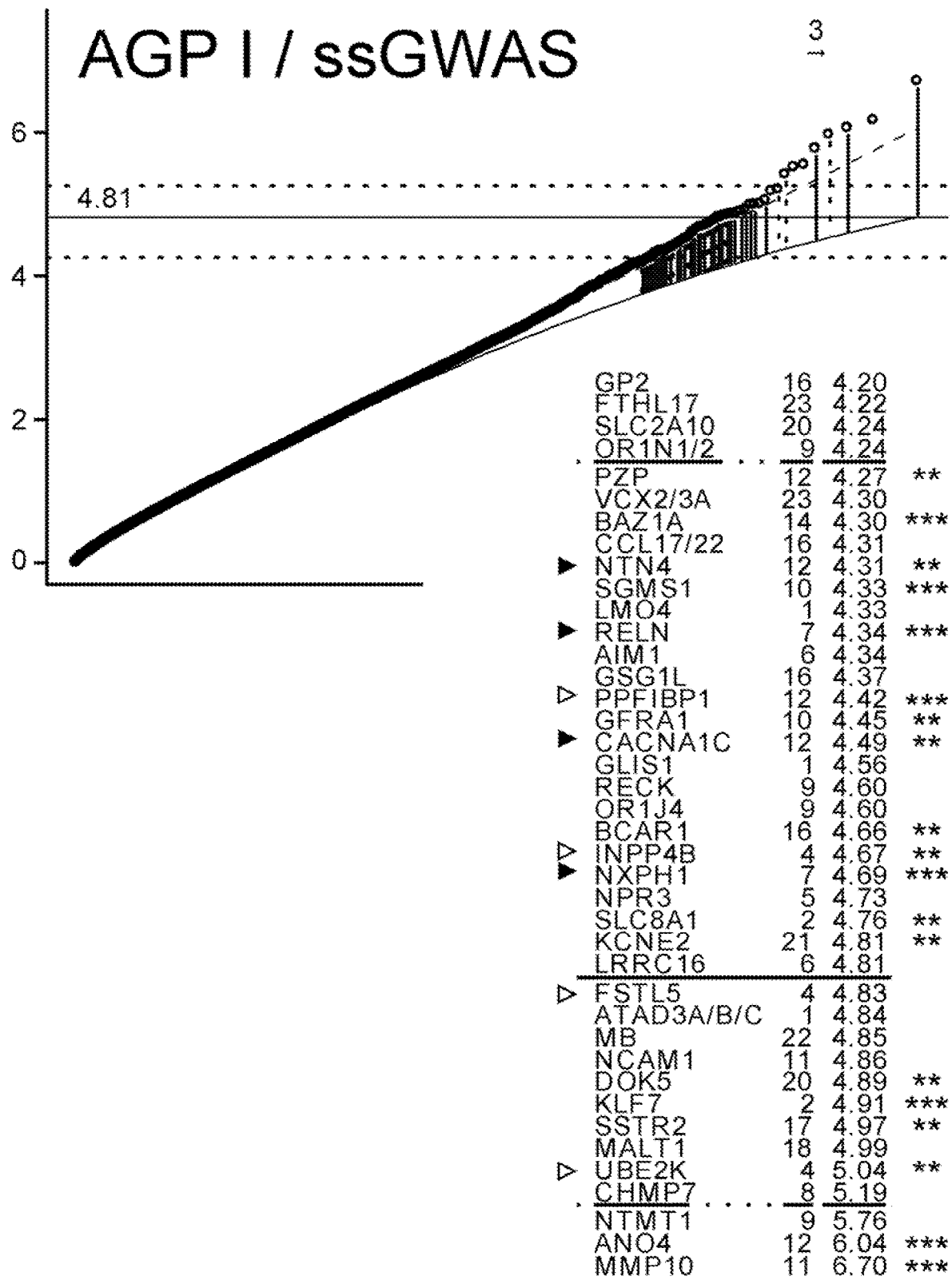
Figure 1C:
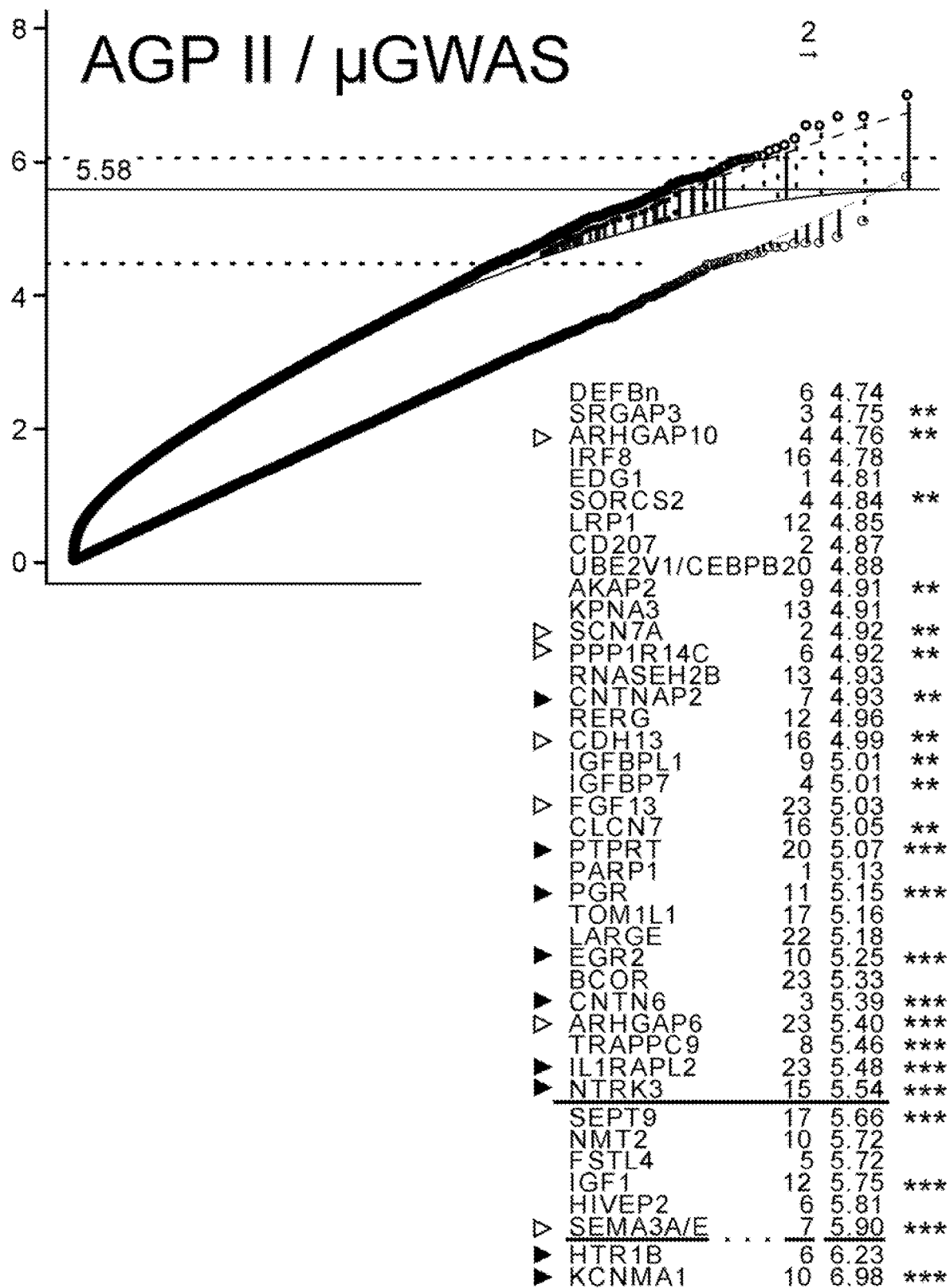
Figure 1D:
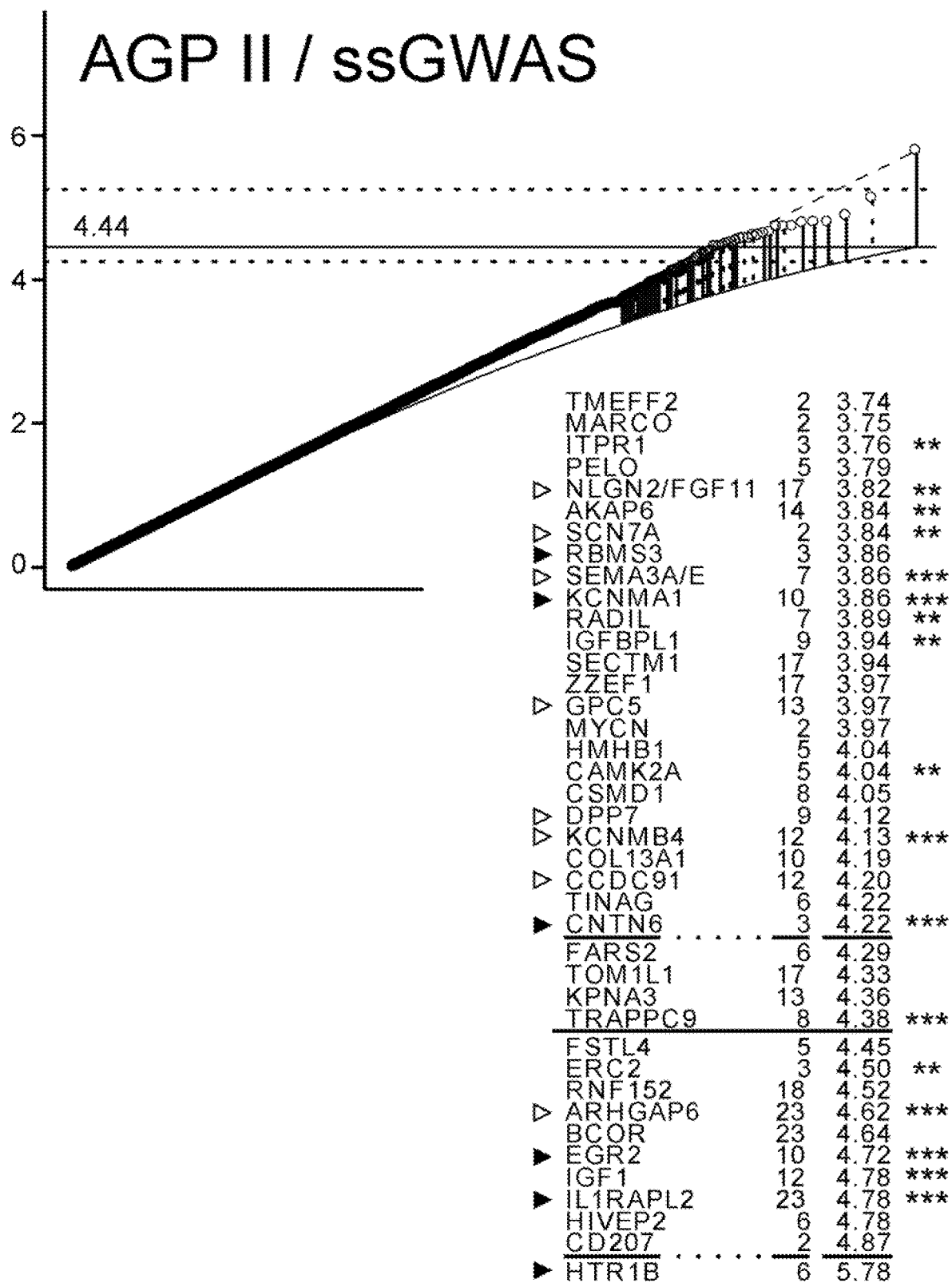

The present invention is based, in part, on the discovery of certain disease-relevant gene clusters following reanalysis of two independent collections (Stages) of autism genetic data (Autism Genome Project (AGP) I and II) using a novel computational biostatistics approach. As described in detail in the Examples, this approach addresses the following two points, which prior biostatistical analyses of the same data using conventional approaches failed to consider: (i) correlation between significance and minor allele frequency or "MAF" and (ii) non-randomization bias. It also addresses multiplicity adjustment for diplotype length, a problem arising from the use of a wide-locus approach. By addressing these points, the present analysis identifies two novel autism-specific gene clusters. One gene cluster comprises several receptor protein tyrosine phosphatases (PTPRs), whose roles include deactivation of growth factors shortly after their activation through growth factor binding. The second gene cluster comprises ion channels and includes Cl⁻ and K⁺ channels. Based on this discovery, the present invention provides, in part, a shift in the focus for potential autism treatments from highly penetrant, but rare variations affecting $Ca^{2+}$ signaling to a broader spectrum of frequent variations affecting signaling of other ions, including Cl⁻ and K⁺. Based on these findings, as presented in detail herein, in some embodiments the present invention provides compositions and methods for treating autism and/or an ASD using active agents that target ion channels and/or modulate their activity. Furthermore, in some embodiments, and based in part of the involvement of PTPRs, the present invention provides compositions and methods that may be useful for the treatment of autism and ASDs during periods of active neuronal growth, such as during early childhood.

Some of the main embodiments of the present invention are described in the above Summary of the Invention section of this application, as well as in the Examples, Figures, and Claims. This Detailed Description of the Invention section provides additional description relating to the compositions and methods of the present invention, and is intended to be read in conjunction with all other sections of the present patent application, including the Summary of the Invention, Examples, Figures, and Claims sections of the present application.

I. Abbreviations & Definitions

The abbreviation "AGP" refers to the Autism Genome Project.
The abbreviation "APAP" refers to acetaminophen/paracetamol.
The abbreviation "ASA" refers to acetylsalicylic acid.
The abbreviation "ASD" refers to Autism Spectrum Disorder.
The abbreviation "CaCC" refers to $Ca^{2+}$-activated Cl⁻ channel.
The abbreviation "CAE" refers to childhood absence epilepsy.
The abbreviation "CaMKII" refers to $Ca^{2+}$/calmodulin kinase II.
The abbreviation "CFA" refers to meclofenamic acid.
The abbreviation "CNV" refers to copy number variation(s).
The abbreviation "DAG" refers to diacylglycerol.
The abbreviation "DCF" refers to diclofenac.
The abbreviation "IP3" refers to inositol trisphosphate.
The abbreviation "EEG" refers to electroencephalography.
The abbreviation "ER" refers to endoplasmic reticulum.
The abbreviation "FFA" refers to flufenamic acid.
The abbreviation "GABA" refers to gamma-aminobutyric acid.
The abbreviation "GF" refers to growth factor.
The abbreviation "GI" refers to gastrointestinal.
The abbreviation "GPCR" refers to G-protein-coupled receptor(s).
The abbreviation "GWAS" refers to genome-wide association studies.
The abbreviation "HFA" refers to high-functioning autism.
The abbreviation "HLA" refers to human leukocyte antigen.
The abbreviation "lD" refers to linkage disequilibrium.
The abbreviation "JIA" refers to juvenile idiopathic arthritis.
The abbreviation "JRA" refers to juvenile arthritis.
The abbreviation "MAF" refers to minor allele frequency (ies).
The abbreviation "MEG" refers magnetoencephalography.
The abbreviation "MFA" refers to mefenamic acid.
The abbreviation "NFA" refers to niflumic acid.
The abbreviation "NMDA" refers to N-methyl-D-aspartate.
The abbreviation "NSAID" refers to non-steroidal anti-inflammatory drug.
The abbreviation "PDD-NOS" refers to pervasive developmental disorder—not otherwise specified.
The abbreviation "PLC" refers to phospholipase C.
The abbreviation "PMCA" refers to plasma-membrane $Ca^{2+}$ ATPase.
The abbreviation "PTPR" refers to receptor protein tyrosine phosphatase.
The abbreviation "QQ" refers to quantile-quantile.
The abbreviation "QR" refers to quantile-rank.
The abbreviation "SDA" refers to strict definition autism.
The abbreviation "SFARI" refers to Simons Foundation Autism Research Initiative.
The abbreviation "SNP" refers to single nucleotide polymorphism.
The abbreviation "SOCC" refers to store-operated calcium ion ($Ca^{2+}$) channels.
The abbreviation "ssGWAS" refers to single-SNP GWAS.
The abbreviation "TD" refers to typical development
The abbreviation "TFA" refers to tolfenamic acid.
The abbreviation "VOCC" refers to voltage-operated $Ca^{2+}$ channels.
The abbreviation "VOPC" refers to voltage-operated potassium channels.
The abbreviation "WG" refers to whole genome.
As used herein, the terms "about" and "approximately," when used in relation to numerical values, mean within + or −20% of the stated value.
As used herein, the terms "treat," "treating," and "treatment" encompass a variety of activities aimed at desirable changes in clinical outcomes. For example, the term "treat", as used herein, encompasses any activity aimed at achieving, or that does achieve, a detectable improvement in one or more clinical indicators or symptoms of a neurodevelopmental disease or disorder—such as autism or an ASD. For example, such terms encompass alleviating, abating, ameliorating, relieving, reducing, inhibiting, preventing, or slowing at least one clinical indicator or symptom, preventing additional clinical indicators or symptoms, reducing or slowing the progression of one or more clinical indicators or symptoms, causing regression of one or more clinical indicators or symptoms, relieving a condition caused by the disease or disorder, and the like. As used herein the terms "treat," "treating," and "treatment" encompass both preventive/prophylactic treatments and therapeutic treatments. In the case of prophylactic treatments, the methods and compositions provided herein can be used preventatively in subjects that do not yet exhibit any clear or detectable clinical indicators or symptoms of the disease or disorder but that are believed to be at risk of developing the disease or disorder, such as autism or an ASD, for example as a result of family history or as a result of genetic testing. In the case of therapeutic treatments, the methods and compositions provided herein can be used in subjects that already exhibit one or more clinical indicators or symptoms of the disease or disorder, such as autism or an ASD. In the case of autism and ASDs, various clinical indicators and symptoms are known to medical practitioners and those of skill in the art. Such symptoms include, but are not limited to, changes in eye tracking, skin conductance and/or EEG measurements in response to visual stimuli, difficulties engaging in and responding to social interaction, verbal and nonverbal communication problems, repetitive behaviors, intellectual disability, difficulties in motor coordination, attention issues, sleep disturbances, and physical health issues such as gastrointestinal disturbances.

The term "autism" is used herein in accordance with its usual usage in the art and includes, but is not limited to, SDA, HFA, and other ASDs. ASD and autism are both terms that encompass a group of complex disorders of brain development. These disorders include, but are not limited to, autistic disorder, Rett syndrome, childhood disintegrative disorder, pervasive developmental disorder not otherwise specified (PDD-NOS), and Asperger's syndrome.

The term "subject" as used herein encompasses mammals, including, but not limited to, humans, non-human primates, rodents (such as rats, mice and guinea pigs), and the like. In some embodiments of the invention, the subject is a human.

The terms "effective amount" or "therapeutically effective amount," as used herein, refer to an amount of an active agent as described herein that is sufficient to achieve, or contribute towards achieving, one or more desirable clinical outcomes, such as those described in the "treatment" description above. An appropriate "effective" amount in any individual case may be determined using standard techniques known in the art, such as a dose escalation study.

The term "pharmaceutical composition" as used herein refers to a composition comprising at least one active agent as described herein (such as, for example, a fenamate, a calcium-activated chloride channel modulator, a potassium channel modulator, a voltage-activated calcium channel modulator, etc.), or a combination of two or more active agents, and one or more other components suitable for use in pharmaceutical delivery such as carriers, stabilizers, diluents, dispersing agents, suspending agents, thickening agents, excipients, and the like.

The term "active agent" as used herein refers to a molecule that is intended to be used in the compositions and methods described herein and that is intended to be biologically active, for example for the purpose of treating autism or an ASD. The term "active agent" is intended to include molecules that either are, or can be converted to a form that is, biologically active. For example, the term "active agent" includes pro-drugs and/or molecules that are inactive or lack the intended biological activity but that can be converted to a form that is active or has the intended biological activity.

Additional definitions and abbreviations are provided elsewhere in this patent specification or are well known in the art.

II. Additional Description

Autism and ASDs are complex diseases involving many genes along common pathways. Based, in part, on mouse studies (Zou H, Yu Y, et al. (2011) *Genes Brain Behav* 10:615-24; Srivastava D P, Woolfrey K M, et al. (2012) *PLoS Biol* 10:e1001350) and enrichment of CNVs in a previous analysis of the AGP I data (Pinto D, Pagnamenta A T, et al. (2010) *Nature* 466:368-72), there is an emerging consensus building that dysregulation of the Ras pathway is involved. $Ca^{2+}$ signaling has an excitatory impact on the Ras pathway and abnormal $Ca^{2+}$ signaling has been implicated in ASD (Deutsch C K, Joseph R M (2003) *J Autism Dev Disord* 33:209-15; McCaffery P, Deutsch C K (2005) *Prog Neurobiol* 77:38-56; Lainhart J E, Bigler E D, et al. (2006) *Am J Med Genet A* 140:2257-74). Still, traditional GWAS have largely failed to elucidate the mechanisms by which Ras and $Ca^{2+}$ signaling interact and have failed to elucidate therapies based on the underlying mechanisms.

There is a wide spectrum of genes having mutations contributing to the risk of a child developing autism or an ASD. The identification of genetic mutations or clusters of genes associated with autism or an ASD (as described further in the Examples) can be used to identify therapeutic agents to treat autism or ASD or determine whether a subject with autism or ASD will be responsive to a particular type of treatment. For example, based on the findings presented herein, a subject with autism or an ASD, including a subject who exhibits a mutation in an anoctamin calcium-chloride channel (for example, a mutation in an ANO1, ANO2, ANO3, ANO4, ANO5, ANO6, ANO7, ANO8, ANO9, or ANO10 channel), may be expected to be responsive to treatment with a calcium-activated chloride channel modulator, for example, a fenamate or an analogue or derivative thereof. Similarly, based on the findings presented herein, a subject with autism or an ASD, including a subject who exhibits a mutation in a voltage-activated calcium channel (for example, a mutation in a voltage-gated calcium channel (CACNA1A . . . CACNA1S) gene), may be responsive to treatment with a voltage-activated calcium channel modulator, for example, gabapentin, pregabalin, atagabalin, or an analogue or derivative thereof.

Early signs of regression toward autism or an ASD have been observed in infants as young as three months old. Indications that a subject is at risk of developing autism or an ASD include behavioral anomalies, alterations in responses to visual stimuli such as familiar and unfamiliar faces, as measured by eye tracking (Chawarska K, Macari S, et al. (2013) *Biol Psychiatry* 74:195-203), EEG (Bosl W, Tierney A, et al. (2011) *BMC Medicine* 9:18; Elsabbagh M, Mercure E, et al. (2012) *Curr Biol* 22:338-42), and skin conductance (Kylliainen A, Hietanen J K (2006) *J Autism Dev Disord* 36:517-25). The onset of symptoms or indicators of autism or ASDs, and the corresponding changes in eye tracking, EEG response, skin conductance (or any combination thereof), occur gradually and thus provide a window during which therapeutic intervention can be initiated. Thus, in some embodiments the present invention provides methods for therapeutic intervention during the period of gradual regression characterized by changes in eye tracking, EEG response, skin conductance, or any combination thereof. However, the methods of treatment described herein are not intended to be limited to use during such time period. On the contrary, the methods of the present invention can be commenced prior to such time period, for example in subjects that are newborns or infants younger than three months in age (particularly where family history or genetic testing indicates that the subject is at risk for developing autism or an ASD), and may be employed, or continued during, later stages of the life of a subject, particularly if a subject is still exhibiting indicators or symptoms of autism or an ASD. The methods of treating autism or an ASD provided by the invention include, but are not limited to, methods for preventing or delaying the onset of autism or an ASD, preventing or delaying the progression of clinical indicators or symptoms of autism or an ASD, and methods for ameliorating clinical indicators or symptoms of autism or an ASD.

The results presented herein suggest that autism and ASDs may be characterized by neuronal hyperexcitation. In some aspects the present invention provides methods of treatment of autism and ASDs that comprise administering to a subject one or more active agents that target ion channels to elicit changes in intracellular ion levels thereby causing a dampening or decrease of neuronal hyperexcitation. Such active agents may specifically target a particular class or type of ion channel or may act non-specifically on several different classes or types of ion channels to elicit a broad reduction of excitation. Furthermore, such active agents could be, for example, compounds or drugs that are already being used safely in humans for other indications and could be repurposed for use in the treatment of autism or ASDs.

A) Active Agents

As further described in the Examples and other sections of the present application, active agents that can be used in the compositions and methods of the present invention include those that modulate the activity of ion channels, such as Cl$^-$, K$^+$, and/or Ca$^{2+}$ channels, including channels that are gated or activated by a mechanism that controls the flow of ions through the channel, for example, calcium-activated, voltage-gated, or ligand-gated channels.

In some embodiments, active agents that can be used in the compositions and methods of the present invention, either alone or in combination with other active agents, include CaCC modulators. CaCC modulators are agents that cause a change in the flow or current of Cl$^-$ ions through a CaCC thereby causing a change in intracellular Cl$^-$. Such modulators include, for example, agents that activate a CaCC, disinhibit a CaCC, increase the activity of a CaCC, or prolong the duration of the open state of a CaCC, and other agents that act as CaCC agonists. Such modulators also include, for example, agents which inhibit a CaCC, inactivate a CaCC, decrease the activity of a CaCC, or prolong the duration of the closed state of a CaCC, and other agents which act as CaCC antagonists. CaCC modulators may act directly on the CaCC to modulate channel activity (for example, by physically binding to or otherwise interacting with the channel) or may act indirectly to modulate channel activity (for example, by effecting a molecule, pathway, or other mechanism which regulates activity of a CaCC). Many CaCC modulators are known in the art, and any such suitable CaCC modulator may be used in conjunction with the methods of the present invention.

In some embodiments, active agents that can be used in the compositions and methods of the present invention, either alone or in combination with other active agents, include potassium channel modulators. K$^+$ channel modulators are agents that cause a change in the flow or current of K$^+$ ions through a K$^+$ channel thereby causing a change in intracellular K$^+$ levels. Such modulators include, for example, agents which activate a K$^+$ channel, disinhibit a K$^+$ channel, increase the activity of a K$^+$ channel, or prolong the duration of the open state of a K$^+$ channel, and other agents that act as K$^+$ channel agonists. Such modulators also include, for example, agents which inhibit a K$^+$ channel, inactivate a K$^+$ channel, decrease the activity of a K$^+$ channel, or prolong the duration of the closed state of a K$^+$ channel, and other agents which act as K$^+$ channel antagonists. K$^+$ channel modulators may act directly on the K$^+$ channel to modulate channel activity (for example, by physically binding to or otherwise interacting with the channel) or may act indirectly to modulate channel activity (for example, by effecting a molecule, pathway, or other mechanism which regulates activity of a K$^+$ channel). Many K$^+$ channel modulators are known in the art, and any such suitable K$^+$ channel modulator may be used in conjunction with the methods of the present invention.

In some embodiments, active agents that can be used in the compositions and methods of the present invention, either alone or in combination with other active agents, include Ca$^{2+}$ channel modulators. Ca$^{2+}$ channel modulators are agents that cause a change in the flow or current of Ca$^{2+}$ ions through a Ca$^{2+}$ channel thereby causing a change in intracellular Ca$^{2+}$ levels. Such modulators include, for example, agents which activate a Ca$^{2+}$ channel, disinhibit a Ca$^{2+}$ channel, increase the activity of a Ca$^{2+}$ channel, or prolong the duration of the open state of a Ca$^{2+}$ channel, and other agents which act as Ca$^{2+}$ channel agonists. Such modulators also include, for example, agents which inhibit a Ca$^{2+}$ channel, inactivate a Ca$^{2+}$ channel, decrease the activity of a Ca$^{2+}$ channel, or prolong the duration of the closed state of a Ca$^{2+}$ channel, and other agents which are Ca$^{2+}$ channel antagonists. Ca$^{2+}$ channel modulators may act directly on the Ca$^{2+}$ channel to modulate channel activity (for example, by physically binding to or otherwise interacting with the channel) or may act indirectly to modulate channel activity (for example, by effecting a molecule, pathway, or other mechanism which regulates activity of a Ca$^{2+}$ channel). Many Ca$^{2+}$ channel modulators are known in the art, and any such suitable Ca$^{2+}$ channel modulator may be used in conjunction with the methods of the present invention. For example, gabapentin, preganalin, atagabalin, and analogues or derivatives thereof, are examples of VOCC modulators that can be used. Gabapentin is currently being used safely and effectively in human subjects, including children. Gabapentin, and/or analogues or derivatives thereof, could be repurposed for use in the compositions and methods of the present invention, for example for treatment of autism or ASDs according to the present invention. Gabapentin is indicated for several medical conditions including pediatric epilepsy (Wittkowski K M, Sonakya V, et al. (2013) *Pharmacogenomics* 14:391-401), and has been tested in children as young as one month old (Ouellet D, Bockbrader H N, et al. (2001) *Epilepsy Res* 47:229-41). In the U.S., gabapentin is currently used to treat seizures in adults and children over 3 years old. Gabapentin is available as an oral solution, tablets or capsules.

In some embodiments, active agents that can be used in the compositions and methods of the present invention, either alone or in combination with other active agents, include modulators of anoctamin calcium-activated chloride channels, for example, the ANO1, ANO2, ANO3, ANO4, ANO5, ANO6, ANO7, ANO8, ANO9, or ANO10 anoctamin calcium-activated chloride channels. A non-limiting example of a modulator of an anoctamin calcium-activated chloride channel is niflumic acid (a fenamate) which targets anoctamins to inhibit the channels. Niflumic acid is used widely (outside of the U.S.) in the treatment of joint and muscular pain. Niflumic acid, and analogues and derivatives thereof, are examples of drugs that could be repurposed for use in the compositions and methods described herein, for example those for the treatment of autism or ASDs.

Figure 5:
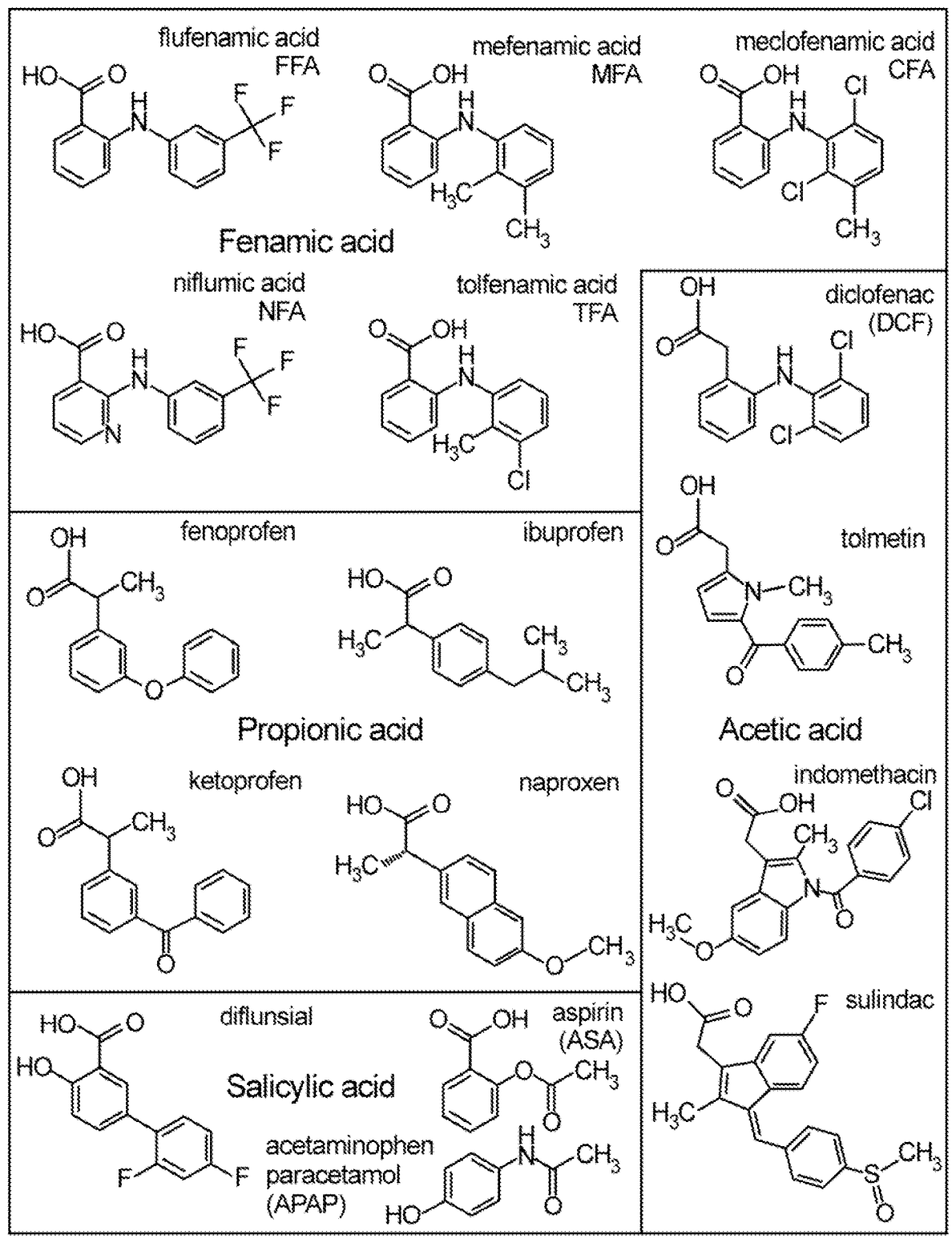
FIG. 5: NSAIDs with carboxyl (COOH) moieties by base acid. APAP is included for comparison.
Figure 6:
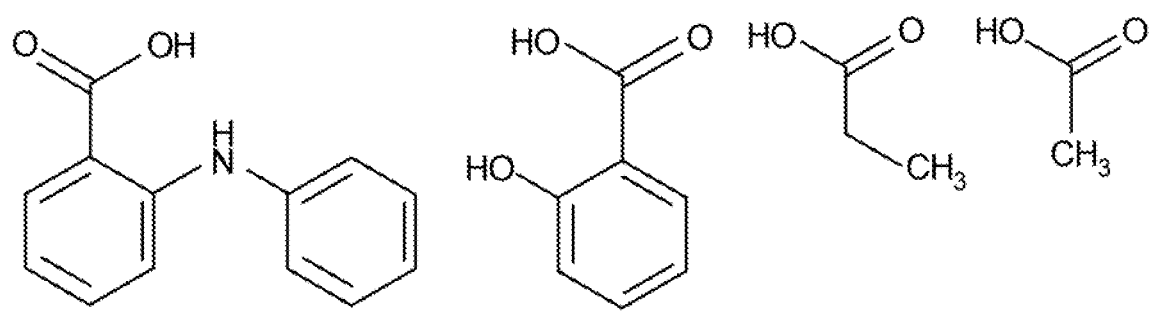
FIG. 6: Base acids of NSAIDs with carboxyl (COOH) moieties. From left, fenamic acid ($C_{13}H_{11}NO_2$, 213.23 g/mol), salicylic acid ($C_7H_6O_3$, 138.12 g/mol), propionic acid ($C_3H_6O_2$, 74.08 g/mol), acetic acid ($C_2H_4O_2$, 60.05 g/mol).

In some embodiments, active agents that can be used in the compositions and methods of the present invention, either alone or in combination with other active agents, include fenamates. Fenamates are a class of compounds that non-specifically target chloride and potassium channels, including anoctamin chloride channels and MaxK potassium channels. Potassium channels have been implicated as familial risk factors in autism and ASDs. In some embodiments fenamates, or analogues or derivatives thereof, are used in the compositions and methods of the present invention, for example for treating autism or an ASD. Fenamates that can be used in the compositions and methods of the present invention include, but are not limited to, MFA, TFA, DCDPC, FFA, CFA, NFA, 5645648, anthracene 9 carboxylic acid, indanyloxyacetic acid, and ethacrynic acid, and analogues and derivatives thereof. The chemical structures of some exemplary fenamates that can be used in accordance with the compositions and methods of the present invention (as well as structures of some related NSAIDs) are provided in FIG. 5. Additional information regarding such fenamate molecules (as well as some related NSAIDs) is provided in Table 1, below.

TABLE 1

Fenamates and related NSAIDs

| INN | IUPAC Name | Synonyms | Formula | Trade Name(s) |
|---|---|---|---|---|
| Fenamic acid | 2-(phenylamino)benzoic acid | n-phenylanthanilic acid | $C_{13}H_{11}NO_2$ | |
| | 2-aminobenzoic acid | anthranilic acid | $C_7H_7NO_2$ | |
| | pyridine-3-carboxylic acid | nicotinic acid | $C_6NH_5O_2$ | |
| | 2-Hydroxybenzoic acid | salicylic acid | $C_7H_6O_3$ | |
| flufenamic acid (FFA): | 2-([3-(trifluoromethyl) phenyl]amino)benzoic acid | N-(3-trifluoromethyl phenyl)anthranilic acid | $C_{14}H_{10}F_3NO_2$ | Mobilat |
| mefenamic acid (MFA) | 2-[(2,3-dimethyl phenyl)amino]benzoic acid | N-(2,3-dimethyl phenyl)anthranilic acid | $C_{15}H_{15}NO_2$ | Ponstel, Ponstan |
| meclofenamic acid (CFA) | 2-[(2,6-dichloro-3-methyl phenyl)amino]benzoic acid | N-(2,6-dichloro-3-methyl phenyl)anthranilic acid | $C_{14}H_{11}Cl_2NO_2$ | Meclomen |
| niflumic acid (NFA) | 2-([3-(trifluoromethyl)phenyl]amino) pyridine-3-carboxylic acid | 2-[3-(trifluoromethyl) anilino] nicotinic acid | $C_{13}H_9F_3N_2O_2$ | Nifluril, Niflugel |
| tolfenamic acid (TFA) | 2-[(3-chloro-2-methyl phenyl)amino]benzoic acid | N-(3-chloro-2-methyl phenyl)anthranilic acid | $C_{14}H_{12}ClNO_2$ | Clotam |
| diclofenac (DCF) | 2-(2-[(2,6-dichloro phenyl)amino] phenyl)acetic acid | | $C_{14}H_{11}Cl_2NO_2$ | Voltaren |
| tolmetin | 2[1-methyl-5-(4-methylbenzoyl)-1H-pyrrol-2-yl]acetic acid | 2[1-methyl-5-[oxo(p-tolyl) methyl]-2-pyrrolyl]acetic acid | $C_{15}H_{15}NO_3$ | |
| indometacin (indomethacin) | 2-[1-(4-chlorobenzoyl)-5-methoxy-2-methyl-1H-indol-3-yl]acetic acid | | $C_{19}H_{16}ClNO_4$ | Indocid, Indocin |
| sulindac | 2-[(1Z)-5-fluoro-1-[(4-methanesulfinylphenyl)methylidene]-2-methyl-1H-inden-3-yl]acetic acid | Z-5-fluoro-2-methyl-1[p-(methlsulfinyl)benzylidene] indene-3-acetic acid | $C_{20}H_{17}FO_3S$ | |
| fenoprofen | 2-(3-phenoxyphenyl) propanoic acid | (2S)-2-amino-3-phenyl-1-propanol | $C_{15}H_{14}O_3$ | Nalfon, Fenopron |
| ibuprofen | 2-[4-(2-methylpropyl)phenyl] propanoic acid | 2-(4-isobutylphenyl) propanoic acid | $C_{13}H_{18}O_2$ | Advil, Motrin |
| ketoprofen | 2-(3-benzoylphenyl) propanoic acid | | $C_{16}H_{14}O_3$ | |
| naproxen | (2S)-2-(6-methoxynaphthalen-2-yl) propanoic acid | (2S)-2-(6-methoxy-2-naphthyl) propanoic acid | $C_{14}H_{14}O_3$ | Aleve |
| diflunisal | 5-(2,4-difluorophenyl)-2-hydroxybenzoic acid | 5-(2,4-difluorophenyl) salicylic acid | $C_{13}H_8F_2O_3$ | |
| aspirin (ASA) | 2-(acetyloxy)benzoic acid | acetylsalicylic acid | $C_9H_8O_4$ | Aspirin |
| acetaminophen (APAP) | N-(4-hydroxyphenyl)acetamide | Paracetamol | $C_8H_9NO_2$ | Tylenol |

Derivatives of fenamates that can be used in accordance with the present invention include, but are not limited to, prodrugs of fenamates, several of which are known in the art. Such prodrugs may comprise, for example, two (or more) fenamate molecules connected directly or by a linker (or linkers) that can be degraded inside the body, such as a disulfide linker (see FIG. 7A), palmityl linker, stearyl linker, glycol linker, PEG linker (see FIG. 7 B) or ester linker. In some embodiments such prodrugs may comprise two (or more) of the same fenamate molecule (see FIGS. 7A and 7B). In some embodiments such prodrugs may comprise two (or more) different fenamate molecules. In some embodiments such prodrugs may comprise a fenamate molecule and a non-fenamate, such as a molecule of another non-fenamate active agent as described herein (see FIG. 7C). For example, a prodrug may comprise both a fenamate molecule (mefenamic) acid and gabapentin (see FIG. 7C). MFA is an example of a fenamate that is currently being used safely and effectively in human subjects, including children, and that could be repurposed for use in the compositions and methods of the present invention, for example for the treatment of autism or ASDs. In some countries of the European Union (EU), mefenamic acid is approved for use in children from 6 months of age for the treatment of pain and fever, including chronic use in juvenile arthritis. Mefenamic acid is also available in specific pediatric formulations (oral suspension) in the EU and suitable dosing regimens in infants and children, as well as adults, are established.

In addition to all of the classes of molecules and specific molecules described herein as potential active agents, derivatives and analogues of such molecules/agents can be used in the compositions and methods of the present invention. Derivatives of the molecules/agents described herein that can be used in accordance with the present invention include, but are not limited to, prodrug derivatives. In some embodiments such prodrug derivatives may comprise polyethylene glycol molecules that have been covalently attached to the drug molecule (i.e. pegylated derivatives). In some embodiments such prodrugs may comprise, for example, two (or more) active agent molecules connected together, either directly or by a linker (or linkers) that can be degraded inside the body, such as a disulfide linker, palmityl linker, stearyl linker, glycol linker, PEG linker or ester linker, or any other suitable linker known in the art. In some embodiments such prodrugs may comprise two (or more) of the same active agent molecule, such as two or more molecules of a fenamate, such as MFA (see the "mirror" MFA prodrugs illustrated in FIGS. 7A and 7B). In some embodiments such prodrugs may comprise two (or more) different active agent molecules, such as a molecule or a fenamate (e.g. MFA) and a molecule of a calcium channel modulator (e.g. gabapentin) (See FIG. 7C). In some embodiments such prodrugs may comprise an active agent molecule and any another suitable molecule, moiety, or chemical group (whether an active agent or not) that can be cleaved or removed from the prodrug to release the active agent molecule.

Figure 7A:
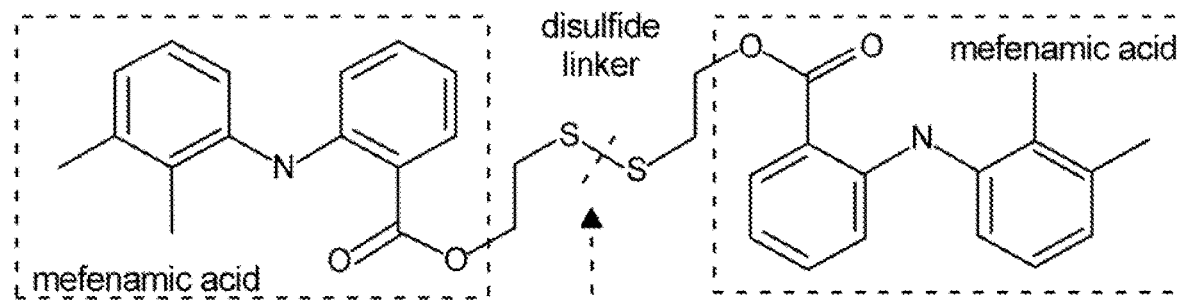
FIG. 7A—Mutual mirror prodrug comprising two MFA molecules connected by a disulfide linker. The prodrug is stable in gastric fluid (pH≈1.2), but dissolves/degrades to release two molecules of MFA (and some inactive components) in serum (pH≈7.4).
Figure 7B:
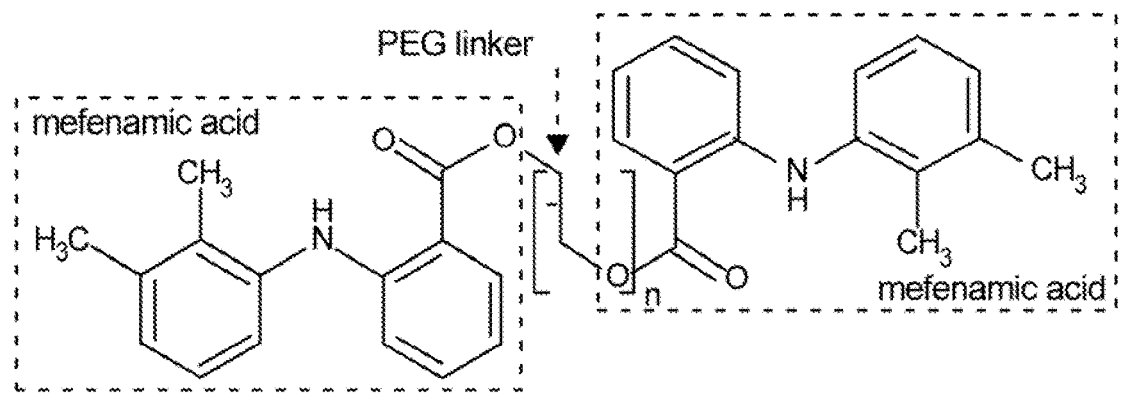
FIG. 7B—Mutual mirror prodrug comprising two MFA molecules connected by a PEG linker. The prodrug is stable in gastric fluid (pH≈1.2), but dissolves/degrades to release two molecules of MFA (and some inactive components) in serum (pH≈7.4).
Figure 7C:
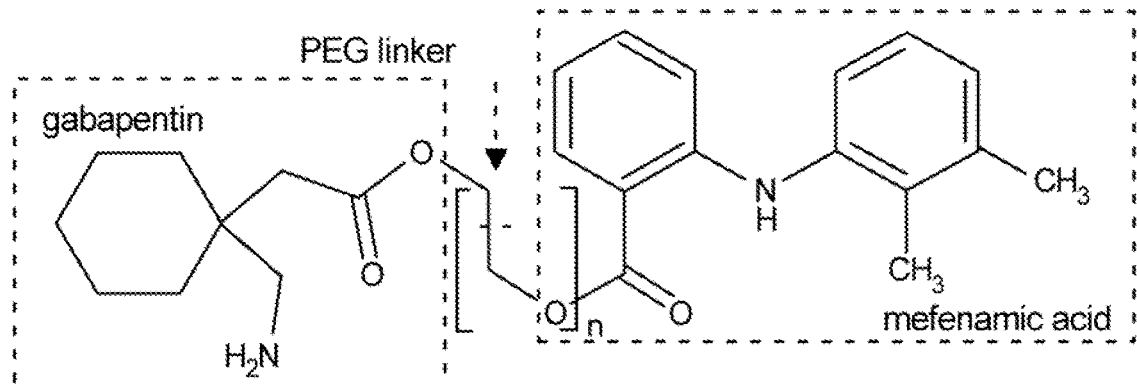
FIG. 7C—Mutual prodrug comprising one MFA molecule and one gabapentin molecule connected by a PEG linker. The prodrug is stable in gastric fluid (pH≈1.2), but dissolves/degrades to release a molecule of MFA and a molecule of gabapentin (and some inactive components) in serum (pH≈7.4).

In some embodiments the present invention provides certain novel mefenamic acid prodrug molecules, including a variety of MFA "mirror" prodrug molecules comprising two MFA molecules joined either directly or via a linker. For example in one embodiment the present invention provides a novel MFA mirror prodrug having two MFA molecules connected by a disulfide linker, as illustrated in FIG. 7A, or an analogue or derivative thereof. The present invention also contemplates a MFA mirror prodrug having two MFA molecules connected by PEG linker, as illustrated in FIG. 7B. Similarly, the present invention also provides MFA mirror prodrug molecules comprising two MFA molecules joined by a palmityl linker, stearyl linker, glycol linker, ester linker, or any other linker known in the art. The present invention also contemplates a non-mirror MFA prodrug having one MFA molecule connected to a gabapentin molecule by a PEG linker, as illustrated in FIG. 7C, or connected by a disulfide linker, palmityl linker, stearyl linker, glycol linker, ester linker, or any other linker known in the art.

The chemical structures of the specific active agent molecules referred to by name herein are well known in the art, or are provided elsewhere in the present patent application. Similarly, methods of making such active agent molecules, and/or commercial sources from which such active agent molecules can be obtained, are well known in the art or are provided elsewhere in the present patent application.

B) Compositions and Administration

In some embodiments the present invention provides compositions comprising any one or more of the active agents described herein, either alone or in combination, for example for use in treating autism or an ASD. For example, in some embodiments, the present invention provides compositions comprising a fenamate, or an analogue or derivative thereof, for example for use in treating autism or an ASD. In some embodiments, the present invention provides compositions comprising gabapentin, pregabalin, or atagabalin, or an analogue or derivative thereof, for example for use in treating autism or an ASD. In some embodiments, the present invention provides compositions comprising both a fenamate, or an analogue or derivative thereof, and gabapentin, pregabalin, or atagabalin, or an analogue or derivative thereof, for example for use in treating autism or an ASD. A non-limiting example of such a pharmaceutical composition is one comprising mefenamic acid and gabapentin. Another non-limiting example of such a pharmaceutical composition is one comprising mefenamic acid, or an analogue or derivative thereof, and gabapentin, or an analogue or derivative thereof. In some embodiments the present invention provides compositions comprising any one of the active agents described herein (such as a fenamate) together with any other agent being tested for its ability to, alleviate one or more symptoms of autism or an ASD, or known to, believed to, or being tested for its ability to alleviate or mitigate any one or more side-effects of the active agent (e.g. GI irritation in the case of fenamates such as MFA).

In some embodiments the compositions of the present invention are pharmaceutical compositions comprising one or more active agents, as described herein, together with one or more conventionally employed components suitable for use in pharmaceutical delivery such as carriers, stabilizers, diluents, dispersing agents, suspending agents, thickening agents, excipients, and the like, may be placed into the form of pharmaceutical formulations. Non-limiting examples of such formulations include solutions, creams, gels, gel emulsions, jellies, pastes, lotions, salves, sprays, ointments, powders, solid admixtures, aerosols, emulsions (e.g., water in oil or oil in water), gel aqueous solutions, aqueous solutions, suspensions, liniments, tinctures, and patches suitable for topical administration. The pharmaceutical compositions and formulations of the invention may, where appropriate, be conveniently presented in discrete unit dosage forms and may be prepared by any of the methods well known in the art of pharmacy. Such methods include the step of bringing into association an active agent with liquid carriers, solid matrices, semi-solid carriers, finely divided solid carriers or combinations thereof, and then, if necessary, shaping the product into the desired delivery system. Unit dosage forms of a pharmaceutical composition or formulation preferably contain a predetermined quantity of active agent and other ingredients calculated to produce a desired therapeutic effect, such as an effective amount of a therapeutically effective amount. Typical unit dosage forms include, for example, prefilled, premeasured ampules or syringes of liquid compositions, or pills, tablets, capsules or the like for solid compositions.

Pharmaceutical compositions of the invention may be administered by a variety of routes including oral, buccal, sublingual, rectal, transdermal, subcutaneous, intravenous, intramuscular, intrathecal, intraperitoneal and intranasal. Depending on whether intended route of delivery is oral or parenteral, the active agents can be formulated as compositions that are, for example, either injectable, topical or oral compositions. Liquid forms of compositions may include a suitable aqueous or nonaqueous vehicle with buffers, suspending and dispensing agents, colorants, flavors and other suitable ingredients known in the art. Solid forms of compositions may include, for example, binders, excipients, lubricants, coloring agents, flavoring agents and other suitable ingredients known in the art. The active agents and pharmaceutical compositions of the invention may also be administered in sustained release forms or from sustained release drug delivery systems known in the art.

C) Dosages

The dose of an active agent of the invention may be calculated based on studies in humans or other mammals carried out to determine efficacy and/or effective amounts of the active agent (see section E, Clinical Outcomes, below). The dose amount and frequency or timing of administration may be determined by methods known in the art and may depend on factors such as pharmaceutical form of the active agent, route of administration, whether only one active agent is used or multiple active agents (for example, the dosage of a first active agent required may be lower when such agent is used in combination with a second active agent), and patient characteristics including age, body weight or the presence of any medical conditions affecting drug metabolism.

In one embodiment of the invention, the dose of active agent is at least 0.1 mg, at least 0.5 mg, at least 1 mg, at least 5 mg, at least 10 mg, at least 20 mg, at least 30 mg, at least 40 mg, at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 550 mg, at least 600 mg, at least 650 mg, at least 700 mg, at least 750 mg, at least 800 mg, at least 850 mg, at least 900 mg, at least 950 mg or at least 1000 mg. In some such embodiments the above dosages are mg/day or mg/kg/day. In another embodiment, the dose of active agent is in the range of 1 to 1000 mg, 1 to 750 mg, 1 to 500 mg, 1 to 250 mg, 1 to 100 mg, 1 to 50 mg, 1 to 25 mg, 25 to 1000 mg, 25 to 500 mg, 25 to 100 mg, 25 to 50 mg, 50 to 1000 mg, 50 to 500 mg, 50 to 100 mg. In some embodiments the above dosages are mg/day or mg/kg/day.

In one embodiment of the invention, the dose of active agent is at least 0.1 mg/kg, at least 0.5 mg/kg, at least 1 mg/kg, at least 5 mg/kg, at least 10 mg/kg, at least 20 mg/kg, at least 30 mg/kg, at least 40 mg/kg, at least 50 mg/kg, at least 75 mg/kg, at least 100 mg/kg, at least 125 mg/kg, at least 150 mg/kg, at least 175 mg/kg, at least 200 mg/kg, at least 225 mg/kg, at least 250 mg/kg, at least 275 mg/kg, at least 300 mg/kg, at least 325 mg/kg, at least 350 mg/kg, at least 375 mg/kg, at least 400 mg/kg, at least 425 mg/kg, at least 450 mg/kg, at least 475 mg/kg, at least 500 mg/kg, at least 550 mg/kg, at least 600 mg/kg, at least 650 mg/kg, at least 700 mg/kg, at least 750 mg/kg, at least 800 mg/kg, at least 850 mg/kg, at least 900 mg/kg, at least 950 mg/kg or at least 1000 mg/kg. In some such embodiments the above dosages are mg/kg/day. In another embodiment, the dose of active agent is in the range of 1 to 1000 mg/kg, 1 to 750 mg/kg, 1 to 500 mg/kg, 1 to 250 mg/kg, 1 to 100 mg/kg, 1 to 50 mg/kg, 1 to 25 mg/kg, 25 to 1000 mg/kg, 25 to 500 mg/kg, 25 to 100 mg/kg, 25 to 50 mg/kg, 50 to 1000 mg/kg, 50 to 500 mg/kg, or 50 to 100 mg/kg. In some embodiments the above dosages are mg/kg/day.

In one embodiment, a single dose may be administered. In another embodiment, multiple doses may be administered over a period of time, for example, at specified intervals, such as, four times per day, twice per day, once a day, weekly, monthly, and the like.

Mefenamic acid and gabapentin are presently used in children and have established dosing regimens. In some embodiments such established dosing regimens may be used in conjunction with the treatment methods of the present invention. For example, currently, infants and children over 6 months old are given mefenamic acid at a dose of 25 mg/kg/day, which may be in several divided doses, for example 3 divided doses a day of 50 mg for children 6 months to under 2 years, 100 mg dose for children 2 years to under 5 years, 150 mg dose for children 5 years to under 9 years, and 200 mg dose for children 9 years to 12 years, for the treatment of pain and/or fever (see Public Assessment Report for paediatric studies submitted in accordance with Article 45 of Regulation (EC) No 1901/2006, as amended; Mefenamic Acid; UK/W/037/pdWS/001 (17 Sep. 2012), the contents of which are hereby incorporated by reference). Such doses of MFA can be used in accordance with the methods of the present invention for treatment of autism or ASDs, or can be used as starting points or guides in the performance of studies, such as dose-response and/or dose-escalation studies, aimed at determining effective amounts of MFA, or other fenamates, or analogues or derivatives thereof, to be used in accordance with the methods of the present invention for treatment of autism or ASDs.

Similarly, dosing regimens for gabapentin for the treatment of epileptic seizures have been established in children and adults. For example, in pediatric patients age 3-12 years, the starting dose ranges from 10-15 mg/kg/day in three divided doses, and the effective dose is subsequently reached by upward titration over a period of approximately 3 days. The effective dose is determined according to the age of the child, as follows: 25-35 mg/kg/day for children over 5 years of age and 40 mg/kg/day for children ages 3-4 years. For the treatment of epileptic seizures in patients over 12 years of age, the starting dose of gabapentin is 300 mg, three times a day, and the effective dose is 900 to 1800 mg/day in divided doses (three times a day) using 300 or 400 mg capsules, or 600 to 800 mg tablets. Such doses of gapapentin can be used in accordance with the methods of the present invention for treatment of autism or ASDs, or can be used as starting points or guides in the performance of studies, such as dose-response and/or dose-escalation studies, aimed at determining effective amounts of gabapentin, or analogues or derivatives thereof, to be used in accordance with the methods of the present invention for treatment of autism or ASDs.

In embodiments where two (or more) active agents are to be used in a method of treatment, whether those active agents are present in separate compositions, the same composition, or even the same molecule (as in the case of some of the prodrugs described herein), a lower dosage of each active agent may be used than would be used if the active agents were used alone. For example, in embodiments where a fenamate, such as MFA or an analogue or derivative thereof, is to be used in combination with another active agent, such gabapentin, or an analogue or derivative thereof, the dose used for each may be reduced as compared to the sample dosages set forth above. For example, in some embodiments, where two active agents are to be used, the dose of each active agent used may be half of that used for the single agents.

D) Subjects

The methods and compositions provided by the invention may be used to treat a neurodevelopmental disease or disorder, such as autism and/or an ASD, in any subject in need of such treatment. In one embodiment, the subject is a human. It should be noted that, while in some embodiments the subjects to be treated are young children of around 3 months to 3 years in age, in other embodiments the methods of treatment described herein are not intended to be limited to such subjects. Rather, in some embodiments the subjects can be of any age, ranging from newborns to older adults. In some embodiments it may be desirable to treat very young subjects, for example newborns and/or young infants, particularly where family history or genetic testing indicates that the subject is at risk for developing autism or an ASD). Similarly, in some embodiments it may be desirable to treat much older subjects, particularly where such subjects are still exhibiting indicators or symptoms of autism or an ASD.

The methods and compositions of the invention may be employed as prophylactic treatments or therapeutic treatments. For prophylactic treatments, the methods and compositions provided herein can be used preventatively in subjects that do not yet exhibit any clear, definitive, or detectable clinical indicators or symptoms of the disease or disorder but that are believed to be at risk of developing the disease or disorder, such as autism or an ASD. A subject receiving prophylactic treatment for autism or an ASD, for example, may not exhibit any clinical indicators or symptoms of autism or an ASD. In the case of therapeutic treatments, the methods and compositions provided herein can be used in subjects that already exhibit one or more clinical indicators or symptoms of the disease or disorder, such as autism or an ASD. A subject receiving therapeutic treatment for autism or an ASD, for example, may have been clinically diagnosed with autism or an ASD or may otherwise exhibit one or more clinical indicators or symptoms of autism or an ASD.

In one embodiment of the invention, a subject may have been identified as being at risk of developing autism or an ASD. In one embodiment, the subject has a family history of autism. In one embodiment, the subject has one or more genetic risk factors associated with autism and/or ASDs, for example, a genetic mutation in a gene encoding a chloride channel, potassium channel, and/or a calcium channel.

In some embodiments, a subject to be treated using the methods and/or compositions of the present invention is a newborn human, or a human child of at least 1 day in age, 1 week in age, 1 month in age, 2 months in age, 3 months in age, 4 months in age, 5 months in age, 6 months in age, 7 months in age, 8 months in age, 9 months in age, 10 months in age, 11 months in age, 12 months in age, 13 months in age, 14 months in age, 15 months in age, 16 months in age, 17 months in age, 18 months in age, 19 months in age, 20 months in age, 21 months in age, 22 months in age, 23 months in age, 24 months in age, or 36 months in age. In one embodiment, the subject is a human child of less than 36 months in age, 30 months in age, 24 months in age, 18 months in age, 17 months in age, 16 months in age, 15 months in age, 14 months in age, 13 months in age, 12 months in age, 11 months in age, 10 months in age, 9 months in age, 8 months in age, 7 months in age, 6 months in age, 5 months in age, 4 months in age, or 3 months in age. In one embodiment, the subject is a human child of between 3 months and 36 months in age, 3 months and 24 months in age, 3 months and 18 months in age, 3 months and 12 months in age, 6 months and 36 months in age, 6 months and 24 months in age, 6 months and 18 months in age, 6 months and 12 months in age, 9 months and 36 months in age, 9 months and 24 months in age, 9 months and 18 months in age, 9 months and 12 months in age, 12 months and 36 months in age, 12 months and 24 months in age, or 12 months and 18 months in age. In one embodiment, the subject is a human child of 3 months in age, 4 months in age, 5 months in age, 6 months in age, 7 months in age, 8 months in age, 9 months in age, 10 months in age, 11 months in age, 12 months in age, 13 months in age, 14 months in age, 15 months in age, 16 months in age, 17 months in age, 18 months in age, 19 months in age, 20 months in age, 21 months in age, 22 months in age, 23 months in age, 24 months in age, 25 months in age, 26 months in age, 27 months in age, 28 months in age, 29 months in age, 30 months in age, 31 months in age, 32 months in age, 33 months in age, 34 months in age, 35 months in age, or 36 months in age.

E) Clinical Outcomes

In some embodiments the methods of treatment provided herein (which comprise, for example, administering to a subject an effective amount of a composition according to the present invention) result in, or are aimed at achieving, a detectable improvement in one or more clinical indicators or symptoms of autism or an ASD, including, but not limited to, changes in eye tracking, skin conductance and/or EEG measurements in response to visual stimuli, difficulties engaging in and responding to social interaction, verbal and nonverbal communication problems, repetitive behaviors, intellectual disability, difficulties in motor coordination, attention issues, sleep disturbances, and physical health issues such as gastrointestinal disturbances.

In some embodiments the methods of the present invention may be initiated in very young human subjects, for example from birth up to around 36 months of age. Onset of early signs of regression towards autism or ASDs occurs gradually, and the methods of the present invention can be employed when early symptoms are detected. Some evidence suggests that neuronal growth stops at around two years of age, therefore, in some embodiments, the methods of treatment provided herein are initiated in infants and children prior to or around 2 years of age, during the active phase of neuronal growth and development in the brain.

Most autism and ASD behavioral symptoms emerge during the second year of life, before a clinical diagnosis can be made. In young subjects where behavioral symptoms are not evident or detectable, other measureable indicators are needed to assess early signs of regression toward autism or ASDs. Examples of such methods include, behavioral evaluation, eye tracking, skin conductance/galvanic skin response, and EEG, all of which can measure underlying brain function in young subjects who do not display definitive behavioral symptoms of autism or ASDs. These methods can be used to measure changes in brain activity in response to stimuli, for example, visual stimuli such as familiar vs. unfamiliar faces; direct vs. averted eye gaze; or still face vs. speaking.

Changes in eye tracking can be indicative of the onset of symptoms associated with autism or ASDs, such as, increased avoidance or anxiety in the child or a loss of curiosity or interest. Disturbances in eye tracking have been measured in 6 month old infants who later developed an ASD (Chawarska K, Macari S, et al. (2013) *Biol Psychiatry* 74:195-203).

A skin conductance analysis, such as galvanic skin response, measures the electrical conductance of the skin, which varies with the moisture level of the skin. Sweat gland activity increases upon physiological arousal of the sympathetic nervous system and can indicate the emotional state of a subject in response to visual stimuli or other stimuli. This method has been carried out in children with autism to determine the effect of eye contact/straight gaze on physiological arousal (Kylliainen A, Hietanen J K (2006) *J Autism Dev Disord* 36:517-25).

Electroencephalography (EEG) can be used to measure brain activity in response to the presentation of stimuli and can detect alterations in brain activity which may indicate subtle brain function abnormalities before behavioral symptoms are apparent. Decreased complexity of an EEG signal indicates abnormal brain connectivity and has been used as a biomarker to determine ASD risk (Bosl W, Tierney A, et al. (2011) *BMC Medicine* 9:18). Magnetoencephalography (MEG) (Yoshimura Y, Kikuchi M, et al. (2013) *PLoS One* 8:e80126) may also be used to measure brain activity.

The above methods are known in the art and can be implemented into dose-response trials to measure efficacy and determine effective amounts of active agents provided by the invention to treat autism or ASDs. An illustrative example is provided of a clinical study to determine effective dosage of an active agent provided by the invention (for example, mefenamic acid) or a combination of active agents as provided by the invention (for example, the combination of mefenamic acid and gabapentin). The active agent or combination of such agents can be compared to placebo starting at the time where first symptoms of regression are observed, such as avoidance of eye-contact, lack of language development expected to be around the age of 12 months, or loss of early language. The primary outcome can be the blinded assessment of changes in eye tracking, galvanic skin response (skin conductance), and EEG response following exposure to visual stimuli (for example, pictures of familiar vs. unfamiliar faces) after two weeks of pharmacological intervention in randomized sequence (cross-over trial). Measurable improvements in eye tracking, skin conductance response, and/or EEG response in trial subjects treated with various doses of an active agent or pharmaceutical composition provided by the invention can be used to determine the effective amount and dosage regimen for the active agent or pharmaceutical composition. In one embodiment of the invention, an improvement may comprise any detectable or measureable increase in a measurement of eye tracking response, skin conductance response, and/or electroencephalography (EEG) response. In one embodiment of the invention, an improvement may comprise an increase of at least 1%, 5%, 10%, 15%, 20% or 25% in a measurement of eye tracking response, skin conductance response, and/or EEG response.

The compositions and methods described herein are illustrative only and are not intended to be limiting. Those of skill in the art will appreciate that various combinations or modifications of the specific compositions and methods described above can be made, and all such combinations and modifications of the compositions and methods described herein may be used in carrying out the present invention. Furthermore, certain embodiments of the present invention are further described in the following non-limiting Examples, and also in the following Claims.

EXAMPLES

Example 1

A Novel Biostatistics Approach Reveals New Therapeutic Strategies for the Treatment of Autism and ASDs The findings presented in Example 1 are further described in Wittkowski, K M. et al., A Novel Computational Biostatistics Approach Implies Impaired Dephosphorylation of Growth Factor Receptors as Associated with Severity of Autism, *Translational Psychiatry* (2014) 4, e354 which is hereby incorporated by reference in its entirety.

This Example describes use of a novel computational biostatistics approach in a genome-wide association study (GWAS) performed using one of the largest studies of ASD in the US, which included 2705 children with ASD from the Autism Genome Project (AGP). Data from two independent populations (Stages) of the AGP (AGO I and AGP II, available from NIH's dbGaP) was analyzed using u-statistics for genetically structured wide-locus data and additional data from unrelated controls to explore epistasis. To account for systematic, but disease-unrelated differences in (non-randomized) genome-wide association studies (GWAS) and for conducting multiple tests in overlapping genetic regions, a novel study-specific criterion for 'genome-wide significance' was employed. The results presented herein confirm the hypothesis that axonal guidance and calcium signaling are involved in autism. Furthermore, additional novel ASD-specific variations identified in this study suggest that protracted growth factor signaling is associated with more severe forms of ASD. In addition, another cluster of related genes identified in the present study suggests chloride and potassium ion channels as additional ASD-specific drug targets. The involvement of growth factors suggests the time of accelerated neuronal growth and pruning at 9-24 months of age, as well as other ages where neuronal growth and/or pruning is occurring, as a period during which treatment with ion channel modulators could be effective in treating or preventing autism—including preventing progression to more severe forms of autism.

Material and Methods

Study subjects/Genotyping. The study was approved as appropriate. No human participants were involved in the research. The samples were genotyped on Human1Mv1_C and Human1M-Duov3_B Illumina chips. The genomic data was downloaded from dbGaP (dataset pht000267.v2.p2) and details of the study population are described elsewhere (Anney R, Klei L, et al. (2010) *Hum Mol Genet* 19:4072-82; Anney R, Klei L, et al. (2012) *Hum Mol Genet* 21:4781-92).

Study design. Risk factors specific to ASD were targeted by comparing case subpopulations meeting the definition of strict definition autism (SDA) to milder cases with ASD (excluding SDA), described herein by the term 'high-functioning autism' (HFA). To reduce variance, only subjects of European ancestry were included from those genotyped on the more frequently used platform in either Stage. In AGP II, female cases were excluded, because of confounding between chip platform and disease severity. The total number of subjects included (m: male/f: female) was 547/98 (SDA) and 358/68 (HFA) in AGP I and 375 (SDA) and 201 (HFA) in AGP II.

Wide-locus approach. To overcome several of the shortcomings seen in previous applications of single-SNP GWAS (ssGWAS) applied to common diseases, several strategies were combined at different stages of the analysis process. Wide-loci of up-to six neighboring SNPs were aimed at as a primary outcome and the same non-parametric GWAS approach was applied based on u-statistics for structured multivariate data (Hoeffding W (1948) *Ann Math Stat* 19:293-325) with genotypic structures (μGWAS) (Wittkowski K M, Sonakya V, et al. (2013) *Pharmacogenomics* 14:391-401) as in a previous CAE study (Wittkowski K M, Sonakya V, et al. (2013) *Pharmacogenomics* 14:391-401). For the AGP I data, the analysis was stratified by sex (Wittkowski K M (1988) *J Am Statist Assoc* 83:1163-70, 87:258), sex-specific results were selected, if either sex, after Bonferroni correction for two sexes (Bonferroni C E (1936) *Publicazioni del Istituto Superiore di Scienze Economiche e Commerciali di Firenze* 8:3-62), was more significant than the stratified analysis. To avoid spurious findings, loci outside of linkage-disequilibrium (LD) blocks containing genes with known function or adjacent to their 5'-end were excluded. Loci highly influenced by a single SNP only were also excluded, unless this SNP was implicated in both Stages or had been implicated in other studies.

MAF-significance correlation. With any finite sample size, the significance of a u- or rank test is limited. Hence, more significant results can only be obtained for SNPs with sufficiently high MAF. ssGWAS simulations were performed with 2,500,000 permuted phenotypes, comparing two groups of equal size for various MAFs. The $1-10^5$ quantile of the permutation distribution drops from the expected $s=-\log_{10} p=5.26$ cut-off, which is routinely met for MAF>0.33, to 4.9 (n=1000 subjects), 4.7 (n=500), and 4.5 (n=300) for a MAF of 0.05. For the 7.5 level, the bias is projected to be even larger. Due to this MAF-significance correlation, the expected diagonal in a ssGWAS QQ plot under the null hypothesis that "no SNP is associated with the trait" (Pearson T A, Manolio T A (2008) *JAMA* 299:1335-44) turns into an expected curve dropping below the diagonal towards the end.

Estimating the expected s-value distribution from $>10^8$ permutations to obtain stable estimates of the $1-10^{-7.5}$ quantile is neither practical, nor sufficient to avoid a biased selection of SNPs for limited tests. Due to the MAF-significance correlation, any SNP 'significant' when comparing observed phenotypes, is also more likely to be 'significant' with random phenotype permutations.

Non-randomization bias. The reason for the above curvature often not being recognized is that GWAS subjects are deterministically categorized based on their outcome (e.g., SDA vs. HFA), rather than randomly assigned to interventions (as in clinical trials). Any deterministically categorized populations, however, are expected to differ systematically in aspects related to neither the condition of interest nor common ancestry factors (which could potentially be accounted for through stratification). When the downward trend from using a limited test and the upward bias from deterministic selection are similar, the s-values ($s=\log_{10}(p)$) may still appear to follow the diagonal, except for loci suggesting 'true association' (Pearson T A, Manolio T A (2008) *JAMA* 299:1335-44).

Multiplicity adjustments for diplotype length. For multivariate tests of overlapping diplotypes, the estimated quantile-rank (QR) curve needs to be elevated above the diagonal throughout to account for multiple tests conducted around the same SNP. Because most of these tests are highly dependent, the elevation of the estimated QR curve compared to the estimated QQ curve (FIG. 1A-FIG. 1D) is limited, but the distance is likely to vary across diseases and populations.

Projected QR curves. The diagonal of the traditional QQ-plot does not depend on any data, including the most 'significant' data. The s-values are expected to fit the diagonal for the most part (except for the most significant results) (Pearson T A, Manolio T A (2008) *JAMA* 299:1335-44, FIG. 1A), as the vast majority of SNPs are expected not to be associated with the disease. In direct analogy, the QR curve for a multivariate test should be 'smooth', with upward deviations indicating 'true association', which could be disease-related or not. Based on the above rationale and the simulation results mentioned above, the highest point of the projected QR curve (apex) for each chromosome can be estimated from a smooth projection of the s-values after truncating as many of the highest values as needed for the projection to have a monotone increase and, conservatively for a limited test, a non-positive second derivative. Fitting against the data also reduces the effect of population stratification (Pearson T A, Manolio T A (2008) *JAMA* 299:1335-44, FIG. 1B). (For computational convenience, locally weighted polynomial regression (Cleveland W S, Devlin S J (1988) *J Am Statist Assoc* 83:596-610) was selected, as implemented in S+ (TIBCO Software Inc.).

Estimated WG QR apex. While chromosomes may differ with respect to their content of related and unrelated risk factors (see, e.g., the HLA region in autoimmune diseases), random errors are expected to have the same distribution across all chromosomes. Hence, the expected WG apex can be estimated as the (winsorized) median projected apex among chromosomes with the smallest deviation of s-values from the projection.

Estimated QR curves. The estimated curve for each chromosome is then calculated as the loess projection (Cleveland W S, Devlin S J (1988) *J Am Statist Assoc* 83:596-610) of this chromosome's s-values with as many of the highest values replaced with the estimated WG apex until the curve's apex is at or below that level. Applied to the WG projection, this procedure yields the estimated WG curve. Simulation results demonstrate the low variance of the estimates from phenotype permutations and the similarity of their median apex with the winsorized median apex estimated from the observed s-values.

Study-specific GWS. For studies aiming to confirm individual SNPs as associated with a phenotype, the 'confirmatory' paradigm (Tukey J W (1980) *American Statistician* 34:23-5) requires adjustment for multiplicity. When applied to GWAS, these adjustments are typically based on a 'customary' fixed 0.05 level, irrespective of study size or relative risk of type I over type II errors (see (Fisher R A (1956), p. 358) and (Gigerenzer G (2004) *Psychol Sci* 15:286-7) for a discussion), and the assumption of 1,000,000 independent SNPs, irrespective of chip density (Pearson T A, Manolio T A (2008) *JAMA* 299:1335-44). Moving from individual SNPs to overlapping diplotypes increases the dependency of any formal multiplicity adjustment on assumptions with questionable biological validity.

As in most GWAS, however, the studies described in this Example do not aim to confirm hypotheses regarding specific SNPs. Instead, the studies described here aim at picking likely candidates from >40,000 (pseudo-) genes, whose relative importance and epistatic interactions are unknown. Since graphical procedures are particularly useful for such 'exploratory' studies (Tukey J W (1977)), QR plots were chosen to guide with interpretation. Exact cut-offs for deviation of s-values from the estimated curve are unknown. When "the knowledge [is] at best approximate[,] an approximate answer to the right question, which is of—ten vague, [is far better] than an exact answer to the wrong question, which can always be made precise" (Tukey J W (1962) *The Annals of Mathematical Statistics* 33:1-67, p. 13-14). Hence, a heuristic approach is presented that relies on fewer unrealistic assumptions than typical attempts to quantify a particular error rate.

The expected WG curve needs to be estimated, the s-values have a complex dependency structure, and the appropriate level of significance ($\alpha$) for the given sample size is unknown. Hence, a heuristic decision rule is proposed based on weak assumptions only. In the long run one would expect most s-values above the apex to be significant at any α>0 (consistency) and regions with the strongest association to have the highest odds at being included (unbiasedness). For a particular α, one could lower the cut-off, but to account for variance in estimating the apex, one would need to raise it. As a compromise, the estimated WG apex is proposed as a cut-off for study-specific GWS.

Quantile-rank plots. As is customary with selection procedures, p-values were used mainly for the purpose of ranking loci. As no particular hypotheses regarding specific loci were to be confirmed, the traditional approach of exploring characteristics of the 'QQ plot' as decision criteria was modified and formalized. For multivariate tests of overlapping diplotypes, the straight line expected in the traditional 'QQ plot' under the univariate WG permutation hypothesis turns into a curve because many tests are performed per SNP. Even though the number of tests performed increases substantially, the increase in s-values ($-\log_{10} p$) shown in the QR curve compared to the QQ line (FIGS. 1A and 1C) is limited, because most tests are highly dependent.

Whole-genome permutation bias. To estimate the expected distribution of s-values, one could average the results of repeated runs with random phenotype permutations. As each µGWAS analysis may require >100,000 hours on a grid/cloud with GPU enabled nodes, however, simulations requiring >108 replications to estimates the $1-10^{-7.5}$ quantile may not be feasible. The estimate from WG permutations (including computationally efficient approximations) is affected by biases due to subjects being categorized based on their outcome (e.g., SDA vs. HFA), rather than randomly assigned to interventions (as in clinical trials), so that the groups are expected to differ systematically in aspects related to neither the condition of interest nor common ancestry factors. With binary outcomes, significant results can also not be caused by a few 'outliers' only, so that significance is correlated with high MAF (ssGWAS) or low skewness of the scores (µGWAS). Hence, regions with significant allelotype differences between observed phenotypes have also a larger chance to be significant among random phenotype permutations.

Selective chromosome permutation. The proposed use of a selected chromosome permutation approach reduces this bias. While chromosomes may differ with respect to their content of disease related and unrelated risk factors, random errors are expected to have the same distribution across all chromosomes. Hence, the above biases are reduced by excluding chromosomes containing regions of high significance when determining the permutation distribution. In particular, the endpoint of the expected distribution for each chromosome can be estimated from the loess projection to the p-values after truncation to ensure a monotone increase and a non-positive second derivative. Similarly, the endpoint of the expected distribution is estimated from the median of the limited set of, e.g., ten, chromosomes with the lowest maximum deviation of the distribution of s-values from the loess projection.

Formal QR cut-off for deviation. The estimate of the expected distribution for each chromosome is then calculated as the loess fit of the individual chromosomes' data with a sufficient number of results at the high end replaced with the expected endpoint until the curve is curtailed to that level, unless the initial loess fit already remains below this target level. The same procedure, when applied to the WG data, yields the estimation of the WG distribution. Simulation results demonstrate the low variance of the estimates based on random permutations of the phenotypes and that their median is closely resembled by the estimate of the distribution obtained from the observed data.

Results

Quantile-rank plots. One aim of this Example was to validate the ability of µGWAS to identify clusters of genes related to the same biological function in two independent populations. For an exploratory aim, a noticeable deviation from the expected distribution under the whole-genome (WG) permutation is commonly used as a decision criterion for selecting candidate genes. Only three AGP I genes (TABLE 2a), but none of the AGP II genes fulfill this heuristic criterion in ssGWAS, compared to eleven and two genes (TABLE 2a/b, excluding NTMT1), respectively (FIGS. 1A and 1C) in µGWAS, even though in both ssGWAS (FIGS. 1B and 1D) and, in particular, µGWAS (FIGS. 1A and 1C), results of both Stages are highly enriched with genes collected in the SFARI Gene data base (TABLE 2).

Whole genome permutation cut-offs. Traditional GWS cut-offs tend to have low sensitivity for enriched genes. In an analysis of AGRE/NIMH data (Weiss L A, Arking D E (2009) *Nature* 461:802-8), for instance, "excess of independent regions associated at $P<10^5$" had been observed even though "no SNP met criteria for genome-wide [permutation] significance [of] $P<2.5\times10^{-7}$". None of the results presented in this Example exceeds this cut-off, either, even though the ssGWAS results (FIG. 1B and FIG. 1D) and in particular, µGWAS results (FIG. 1A and FIG. 1C), of both Stages are highly enriched with genes collected in the SFARI Gene data base (FIG. 1, triangles). With the more aggressive exclusion of SNPs based on µ-scores for quality-of-data, the WG projection apices of approximately 6.0 and 7.0 for ssGWAS and µGWAS, respectively (FIG. 1), are exceeded once, by MMP10 in ssGWAS of AGP I. A noticeable deviation from the expected distribution is commonly used as a decision criterion for selecting candidate genes (Pearson T A, Manolio T A (2008) *JAMA* 299:1335-44). Based on the projected WG curve, only three AGP I genes (TABLE 2a), but none of the AGP II genes fulfill this criterion in ssGWAS, compared to eleven and two genes (TABLE 2a/b, excluding NTMT1), respectively (FIG. 1A and FIG. 1C) in µGWAS (Wittkowski K M, Sonakya V, et al. (2013) *Pharmacogenomics* 14:391-401).

TABLE 2

Genes identified in study grouped by function

| $s_I$ | $s_{II}$ | $s_F$ | Symbol | Synonym | Entrez | Gene Name (some shortened to fit) | Function (selected from Entrez/Uni-ProtKB/Swiss-Prot/TOCRIS) |
|---|---|---|---|---|---|---|---|
| a) Genes above the projected apex in ssGWAS (µGWAS p-values shown) | | | | | | | |
| 6.96 | 6.21 | | ANO4 | ♪ TMEM16D | 121601 | Anoctamin 4 | $Ca^{2+}$-activated $Cl^-$ channel (CaCC) |
| | | 6.19† | ANO2 | ♪ TMEM16B | 57101 | Anoctamin 2 | (see ANO4) |

TABLE 2-continued

Genes identified in study grouped by function

| $s_I$ | $s_{II}$ | $s_F$ | Symbol | Synonym | Entrez | Gene Name (some shortened to fit) | Function (selected from Entrez/Uni-ProtKB/Swiss-Prot/TOCRIS) |
|---|---|---|---|---|---|---|---|
| 6.94 | 3.76 | 9.29 | DOK5 | | 55816 | Docking protein 5 | Interacts with phosphorylated receptor tyrosine kinases |
| 5.76 | | | NTMT1 | METTL11A | 28989 | N-methyl-transferase 1 | Methylates protein targets such as SET and RB | b) Genes above the estimated apex in μGWAS

| 6.81 | | | MMP10 | Stromelysin 2 | 4319 | Matrix metallo-peptidase 10 | Degrades proteoglycans and fibronectin |
| 6.73 | | | PDGFB | | 5155 | Platelet-derived GF β | Initiating signaling through the MAPK, PI3K and PKCγ pathways |
| 6.64 | | | MRGPRX2 | | 117194 | MAS-related GPR, mbr X2 | $G_q$PR mediating cortistatin-stimulated increases in intracellular $Ca^{2+}$ |
| 6.63 | | | SGMS1 | TMEM23 | 259230 | Sphingomyelin synthase 1 | large, zinc finger-containing transcription factor |
| 6.62 | | | GRIK5 | | 2901 | Glutamate receptor, ionotropic, kainate | Excitatory neurotransmitter in the CNS |
| 6.59 | | | SMAP2 | | 64744 | Small ArfGAP2 | Stromal GTPase activating protein (GAP) that acts on ARF1. |
| 6.55 | | | FAM13A | ARHGAP48 | 10144 | Fam with sequence similarity 13, mbr A | Rho GTPase activating protein |
| 6.44 | 4.84 | 9.85 | SORCS2 | | 57537 | Sortilin-related receptor 2 | Containing VPS10 domain |
| 6.38 | 4.20 | 9.17 | PPFIBPI | e) | 8496 | Liprin Beta 1 | PTPRF interacting protein, binding protein 1 |
| 6.98 | KCNMA1 | Kcal.1 | 3778 | | | Maxi-K $Ca^{2+}$-activated channel | Large conductance channel that dampens excitatory events |
| 6.23 | HTR1B | 5-HT1B | 3351 | | | Serotonin receptor 1B | G protein-coupled receptor involved in neuropsychiatric disorders | c) Genes above the projected apex in μGWAS in both Stages (in addition to SORCS2)

| 5.27 | 4.99 | 8.86 | CDH13 | H-cadherin | 1012 | Cadherin 13 | Downregulates axon growth during neural differentiation |
| 5.02 | 5.15 | 8.78 | PGR | NR3C3 | 5241 | Progesteron receptor | Nuclear/membrane hormone receptor |
| 5.42 | 4.64 | 8.68 | GRK5 | | 2869 | GPR kinase 5 | phosphorylates the activated forms of GPRs |
| 5.43 | 4.51 | 8.56 | PZP | | 5858 | Pregnancy-zone protein | Inhibits all four classes of proteinases |
| 4.89 | 5.07 | 8.57 | PTPRT | e) | 11122 | PTP, receptor type, T | May be involved in signal transduction and cellular adhesion in the CNS |

TABLE 2-continued

Genes identified in study grouped by function

| $s_I$ | $s_{II}$ | $s_F$ | Symbol | Synonym | Entrez | Gene Name (some shortened to fit) | Function (selected from Entrez/UniProtKB/Swiss-Prot/TOCRIS) |
|---|---|---|---|---|---|---|---|
| | d) Additional Genes jointly (Fisher) above the joined projected apex in µGWAS (in addition to KCNMA1) | | | | | | |
| 4.81 | 5.81 | 9.22 | HIVEP2 | Schnurri-2 | 3097 | MHC binding protein 2 | |
| 4.74 | 5.66 | 9.01 | SEPT9 | | 10801 | Septin 9 | Filament-forming cytoskeletal GTPase |
| 5.85 | 4.52 | 8.97 | DMD | | 1756 | Dystrophin | Ligand for dystroglycan |
| 5.61 | 4.44 | 8.66 | SHROOM3 | APXL3 | 57619 | F-actin-binding protein | Controls cell shape changes during neural tube closure |
| | e) Genes related to PTPRs above the projected apex in µGWAS in at least one Stage (in addition to PPFIBP1 and PTPRT)) | | | | | | |
| 5.64 | 3.47 | 7.77 | PTPRB | | 9665 | PTP, receptor type, B | Interacts with neuronal receptor, contactin and tenascin C |
| 4.05 | 4.53 | 7.26 | PTPRD | | 5789 | PTP, receptor type, D | Interaction with IL1RAPL1 for synapse formation |
| | 5.47 | | IL1RAPL2 | | 26280 | IL-1 receptor accessory protein-like 2 | Closely related to IL1RAPL1 |
| | 5.39 | | CNTN6 | NB-3 | 27255 | Contactin 6 | Mediate cell surface interactions during NS development. |
| | 4.93 | | CNTNAP2 | AUTS15 | 26047 | contactin associated protein-like 2 | Mediates neuron-glia interactions during NS development |
| | 4.58 | | CNTN4 | BIG-2 | 152330 | Contactin 4 | May play a role in the formation of axon connections |
| | 4.68 | | ERC2 | | 26059 | ELKS/RAB6-interacting/ CAST fam mbr 2 | May recruit liprin-alpha proteins to the nerve terminals active zone |
| | f) Genes related to Cl⁻ signaling above the projected apex in µGWAS in at least one Stage (in addition to ANO4) | | | | | | |
| | 5.05 | | CLCN7 | PPP1R63 | 1186 | Chloride channel, voltage-sensitive 7 | $H^+/Cl^-$ Exchange Transporter 7 |
| | 4.65 | | CAMK2A | | 815 | CaM dependent kinase II alpha | Mediates many of the second messenger effects of $Ca^{2+}$ |
| | 4.67 | | LRRC7 | Densin-180 | 57554 | leucine rich repeat containing 7 | Necessary for DISC1 and GRM5 localization to PSD complexes |

Table 2, above provides an overview of genes in GW analyses meeting significance criteria and relationships to functional clusters described herein. (GF: growth factor, GPR: G protein-coupled receptor, mbr: member, fam: family, PTP: protein tyrosine phosphatase, Cam: Calcium/Calmodulin, †: from comparison of HFA cases vs. all parental controls, bold gene names and superscripts [e)/f)]: indicate genes related to section e) and f), respectively) Selective chromosome permutation approach and cut-off. The proposed selective chromosome permutation approach (see Methods) accounts for the WG permutation bias. In both AGP Stages, approximately 100 genes deviate from the expectation as an heuristic criterion for expected enrichment (Schork A J, Thompson W K, et al. (2013) *PLoS Genet* 9:e1003449). The set of genes deviating sufficiently from the expected distribution can be difficult to determine objectively. This Example proposes the estimated WG QR apex as a more formal study-specific criterion, which here increases the number of significant regions from none (when compared against a fixed GWS of 7.5) to 18 and 8 for AGP I and II, respectively (FIG. 1, solid horizontal lines).

In all µGWAS included, i.e., FIG. 1 (four analyses), as well as in numerous others, <20 genes or gene regions (e.g., HLA) exceeded study-specific GWS. The high enrichment with pathway genes even below the WG apex in μGWAS of AGP II (FIG. 1C) attests to the proposed approach being conservative. Further support comes from the number of selected genes being smaller with randomized vs. observed phenotypes (3-7 vs. 14), consistent with the above MAF-significance correlation, and also smaller with comparable populations of smaller size, as expected in selection procedures (Bechhofer R E (1954) *Ann Math Stat* 25:16-39; Lehmann E L (1961) *Ann Math Stat* 32:990-1012). The lower level of 5.58 in AGP II vs. 5.81 in AGP I reflects the typical adjustment for power in a selection procedure.

The previous CAE study and the additional comparison of HFA cases vs. parental controls had study-specific HSC cut-off of 7.20 (21 functional regions, including CNTNAP2, DLGAP1, and NALCN as $19^{th}$ to $21^{st}$), and 4.91. 25 regions, including ARHGAP24, SLC25A21, and PTENP1 as $25^{th}$, $22^{nd}$, and $20^{th}$).

Specificity of the proposed approach in the current study. A common problem with many 'pathway analysis' approaches is that a sufficient number of inconsistent findings may be present in the published literature for at least one 'significant' pathway to fit (almost) any set of genes generated by GW genotyping or expression analyses. Hence, a major advantage of the current study is that the primary hypothesis about Ras/$Ca^{2+}$ signaling being involved had been stated a-priori based on previous CAE results, increasing confidence in the current ASD results ("prioritized subset" (Li C, Li M, et al. (2008) *Hum Hered* 65:129-41)) and allowing the specificity of the proposed selective chromosome permutation strategy/cut-off for study specific GWS to be discussed.

Of the top 100 genes selected in AGP I and II, 57 and 47 genes, respectively, could be related to Ras/$Ca^{2+}$ signaling (FIG. 1), matching a targeted false discovery rate of 50% (Schork A J, Thompson W K, et al. (2013) *PLoS Genet* 9:e1003449). The increasing enrichment toward the top 50 and top 20 genes, reaching 100% for the top twelve regions in AGP I, attests to the high specificity of the results. Additional support comes from the replication of the results in two independent populations (see below).

In an unrelated autoimmune disease, psoriasis, however, the majority of genes identified were located in the HLA region or interleukins. The lack of overlap between these unrelated diseases further attests to the specificity of the present approach.

To guide with interpretation, the subset of genes among the top 100 of either Stage that were previously reported as related to Ras/$Ca^{2+}$ signaling and the matching genes among the top 100 genes from either of the two Stages of the current Example are arranged in FIG. 2 around a putative 'consolidated pathway' derived from several 'canonical pathways'. While many variations of such a consolidated pathway could be constructed, there is sufficient consensus among canonical pathways for functionally related genes likely to be depicted in close proximity in any of these consolidated pathways.

Figure 2A:
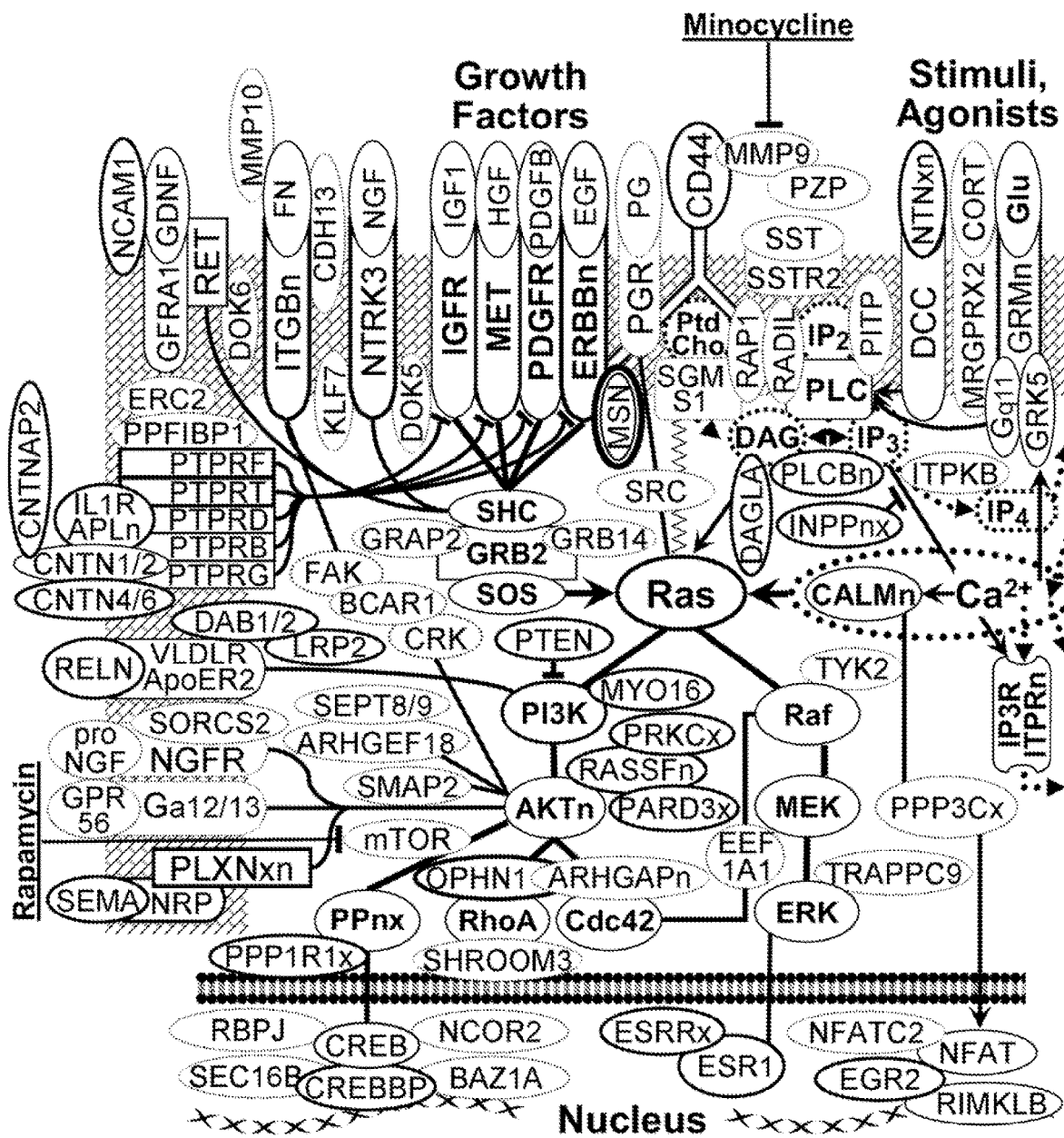
FIG. 2A-FIG. 2H: Ras/$Ca^{2+}$ signaling in ASD and childhood absene epilepsy (CAE).
Figure 2B:
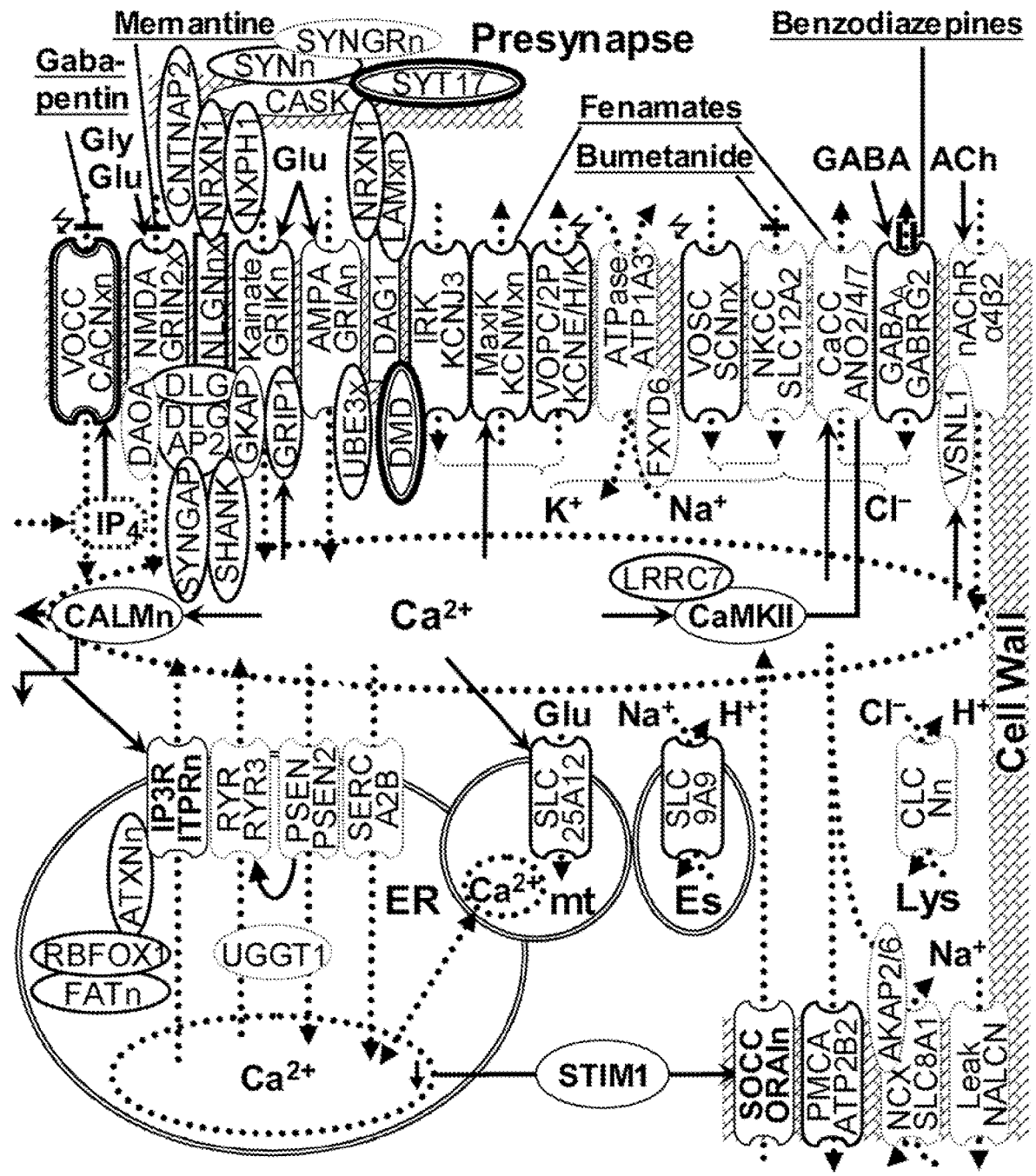
Figure 2C:
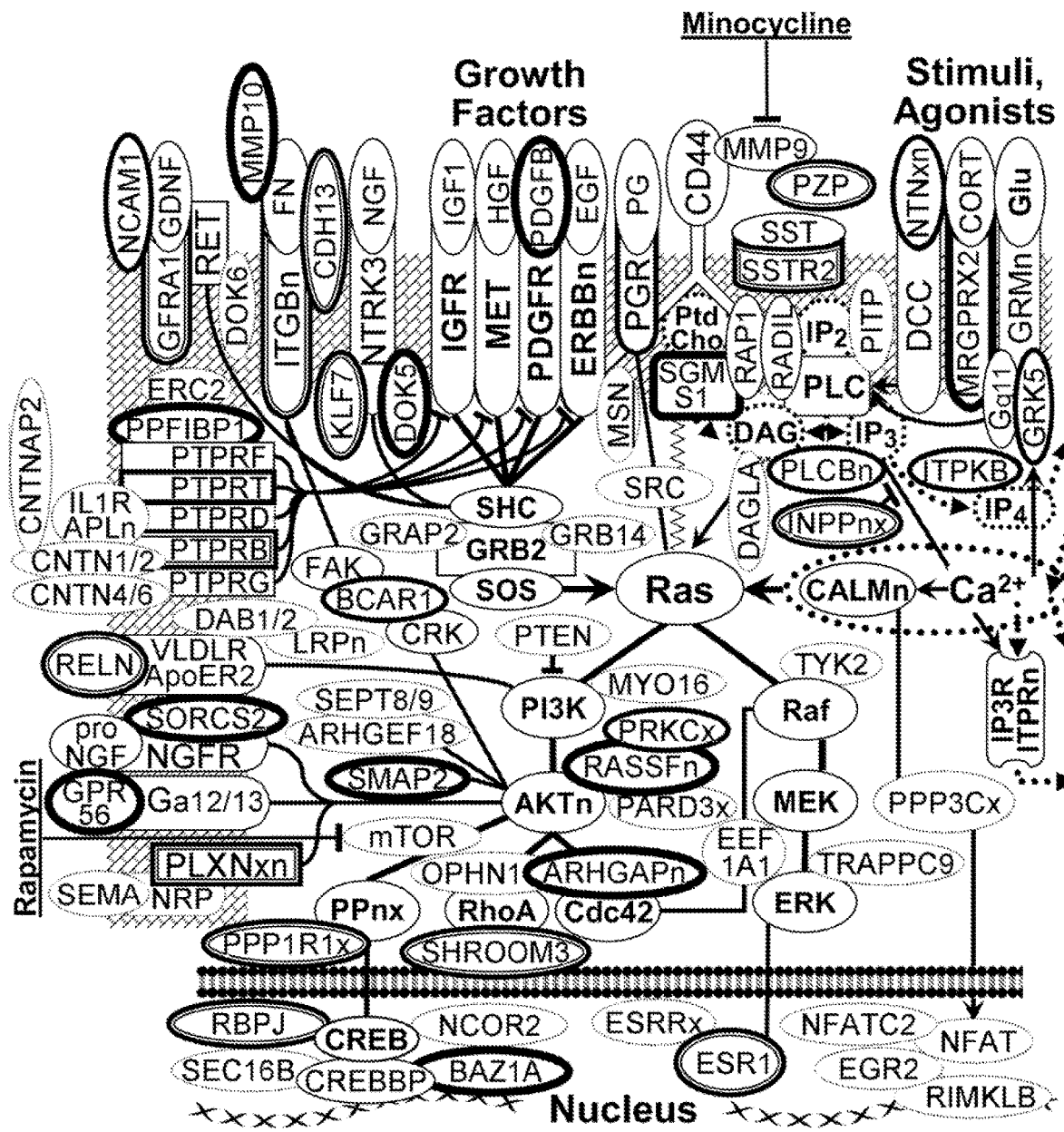
Figure 2D:
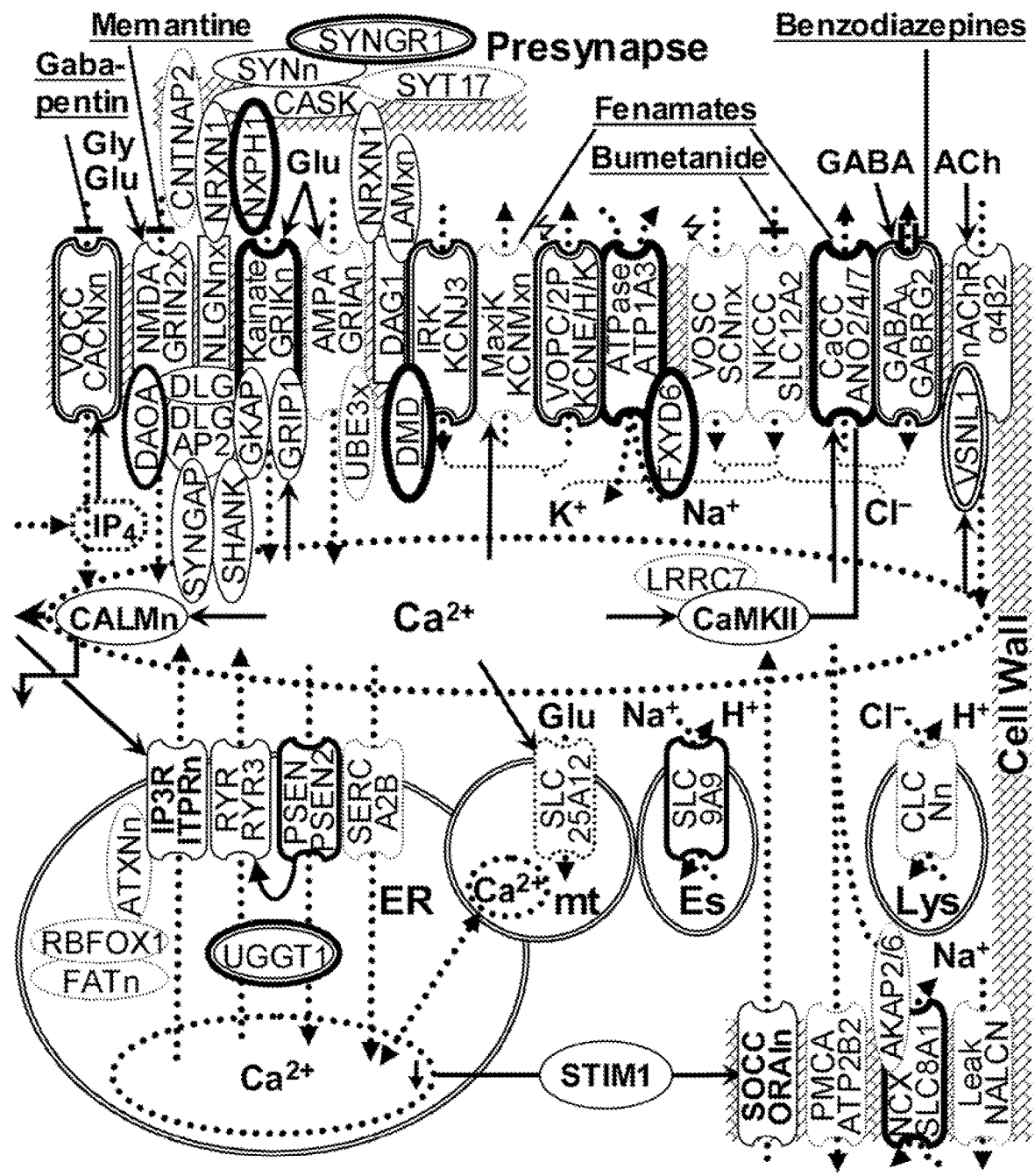

Replication across independent populations. With complex diseases, independent studies are not expected to show more than the functional equivalence seen in the close overlap between Stages (AGP I (FIG. 2C and FIG. 2D); AGP II (FIG. 2E and FIG. 2F)). When hundreds of genes contribute (Yu T W, Chahrour M H, et al. (2013) *Neuron* 77:259-73), few, if any, would be expected to be among the most significant in any two independent studies, even in the absence of selection and ascertainment bias. The two AGP populations, however, were collected consecutively in different sets of locations. Female cases could only be included in AGP I, due to imbalances in disease severity and chip platform usage. The results of the exploratory pathway analysis suggest that AGP I and II patients vary more with respect to behavior ("schizophrenia") and developmental risk factors ("neuritogenesis"), respectively.

Still, seven genes among the top 100 in both Stages (TABLE 2c) can be directly related to the hypothesized pathway (ranks and Fisher's (Fisher R A (1948) *The American Statistician* 2:30) combined s-values $s_F$ in parentheses): SORCS2 ($10^{th}/36^{th}$, 9.85) binds NGFR and mediates apoptosis (Teng K K, Felice S, et al. (2010) *Developmental Neurobiology* 70:350-9) as well as responses to proneurotrophins (Lane R F, St George-Hyslop P, et al. (2012) *J Neurosci* 32:14080-6). CDH13 ($45^{th}/25^{th}$, 8.86) is an atypical cadherin involved in cell signaling, rather than adhesion. It co-localizes with $\alpha_v\beta_3$ integrin (Berx G, van Roy F (2009) *Cold Spring Harb Perspect Biol* 1:a003129), downregulates neural cell growth (Takeuchi T, Misaki A, et al. (2000) *J Neurochem* 74:1489-97), and was disrupted by a microdeletion in an ASD case (Sanders Stephan J, Ercan-Sencicek A G, et al. (2011) *Neuron* 70:863-85). The membrane progesterone receptor (Thomas P, Pang Y (2012) *Neuroendocrinology* 96:162-71) PGR ($66^{th}/18^{th}$, 8.78) drives ERK/MAPK signaling (Boonyaratanakornkit V, Scott M P, et al. (2001) *Mol Cell* 8:269-80) and contributes to neuron excitability through steroids (Losel R, Wehling M (2003) *Nat Rev Mol Cell Biol* 4:46-56) in the brain (Brinton R D, Thompson R F, et al. (2008) *Front Neuroendocrinol* 29:313-39). GRK5 ($36^{th}/59^{th}$, 8.68) controls neuronal morphogenesis (Chen Y, Wang F, et al. (2011) *J Cell Biol* 194:905-20) by phosphorylating G-protein coupled receptors (GPCRs) and initiates β-arrestin-mediated downregulation in a $Ca^{2+}$/calmodulin-dependent fashion. PZP ($34^{th}/93^{rd}$, 8.56) interacts with the target of minocycline, MMP9 (Arbelaez L F, Bergmann U, et al. (1997) *Arch Biochem Biophys* 347:62-8), which cleaves (Chetty C, Vanamala S K, et al. (2012) *Cell Signal* 24:549-59) the extracellular component of CD44 (Peng S T, Su C H, et al. (2007) *Int J Oncol* 31:1119-26), whose expression has been implicated in ASD (Hu V W, Frank B C, et al. (2006) *BMC Genomics* 7:118) and whose intracellular component interacts with Ras (Kumar R A, Sudi J, et al. (2010) *J Med Genet* 47:81-90) via both ERBB2 and PLC (Cichy J, Pure E (2003) *J Cell Biol* 161:839-43; Zoller M (2011) *Nat Rev Cancer* 11:254-67). PTPRT ($90^{th}/20^{th}$, 8.57) is discussed below.

Among the top genes with $s_F>8.5$ (TABLE 2d) are several more ASD related genes. KCNMA1 ($795^{th}/1^{st}$, 9.38) and DOK5 ($2^{nd}/497^{th}$, 9.29), also listed among the individual genes, are a Maxi-K channel in which rare mutations have been identified (Laumonnier F, Roger S, et al. (2006) *Am J Psychiatry* 163:1622-9) and a gene, which mediates neurite outgrowth, respectively. HIVEP2 ($110^{th}/4^{th}$, 9.22) is also known as Schnurri-2 and Shn-$2^{(-/-)}$ mice exhibited hypersensitivity to stress accompanied by anxiety-like behavior (Takagi T, Jin W, et al. (2006) *Brain Res* 1108:88-97). Mutations in SEPT9 ($123^{rd}/8^{th}$, 9.01) cause hereditary neuralgic amyotrophy (Kuhlenbaumer G, Hannibal M C, et al. (2005) *Nat Genet* 37:1044-6). DMD ($17^{rd}/88^{th}$, 8.97) is a member of a glycoprotein complex, which accumulates at a variety of neuronal synapses. Dystrophin is associated with Duchenne and Becker muscular dystrophies (DMD), where it is implicated in signaling events and synaptic transmission. DMD is comorbid to ASD (Wu J Y, Kuban K C, et al. (2005) *J Child Neurol* 20:790-5). Two studies found a genetic association of DMD with ASD (Wang K, Zhang H, et al. (2009) *Nature* 459:528-33; Chung R H, Ma D, et al. (2011) *Mol Autism* 3:2), and one deletion in DMD was found in a CNV analysis of the AGP I data (Pinto D, Pagnamenta A T, et al. (2010) *Nature* 466:368-72). The ortholog of SHROOM3 ($23^{th}/109^{th}$, 8.66) in mice is required for proper neurolation (Hildebrand J D, Soriano P (1999) *Cell* 99:485-97). The combined results of PPFIBP1 ($11^{th}/197^{th}$, 9.17), which is also included in the univariate results above, is discussed with PTPRs below.

Figure 2E:
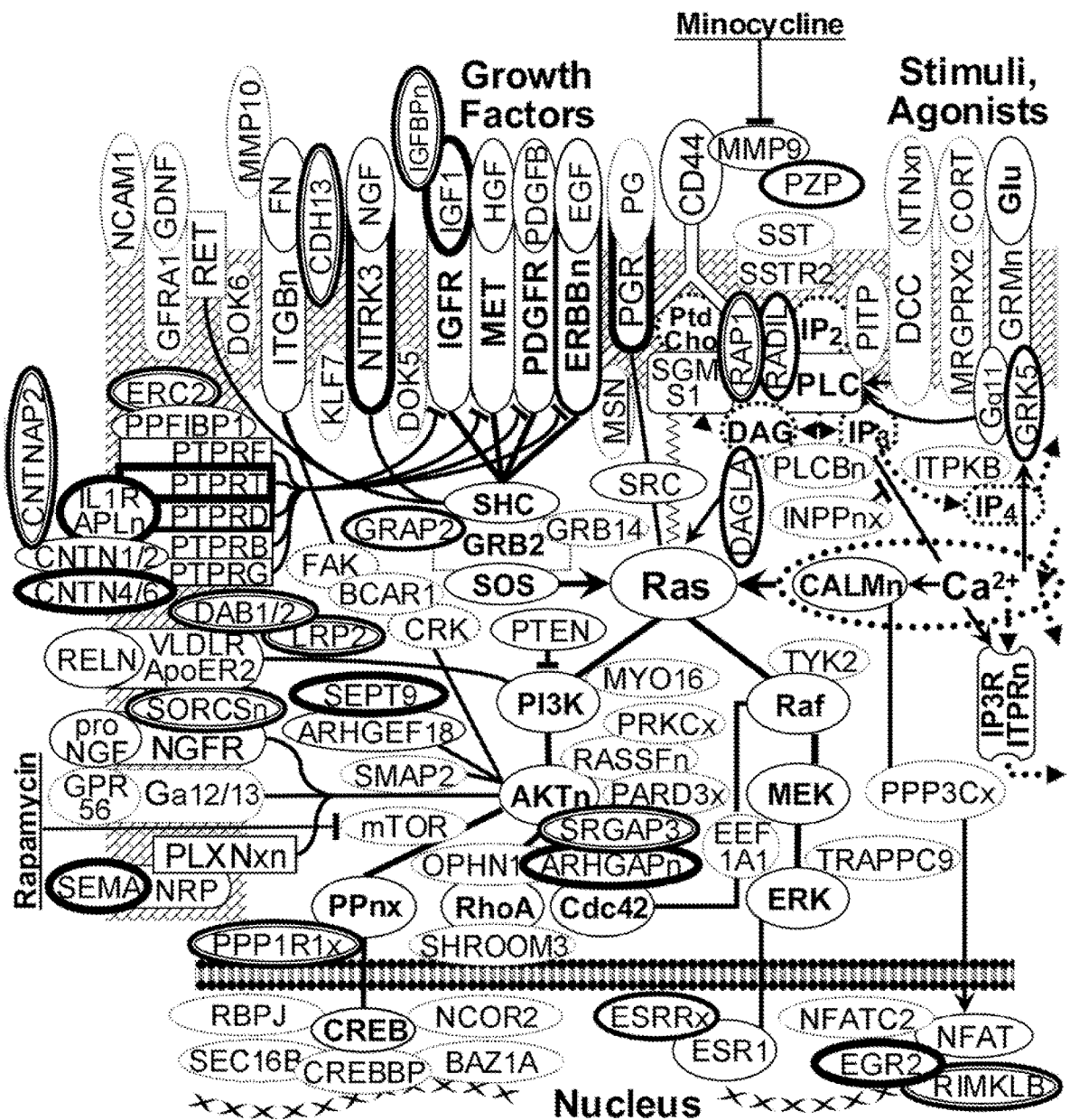
Figure 2F:
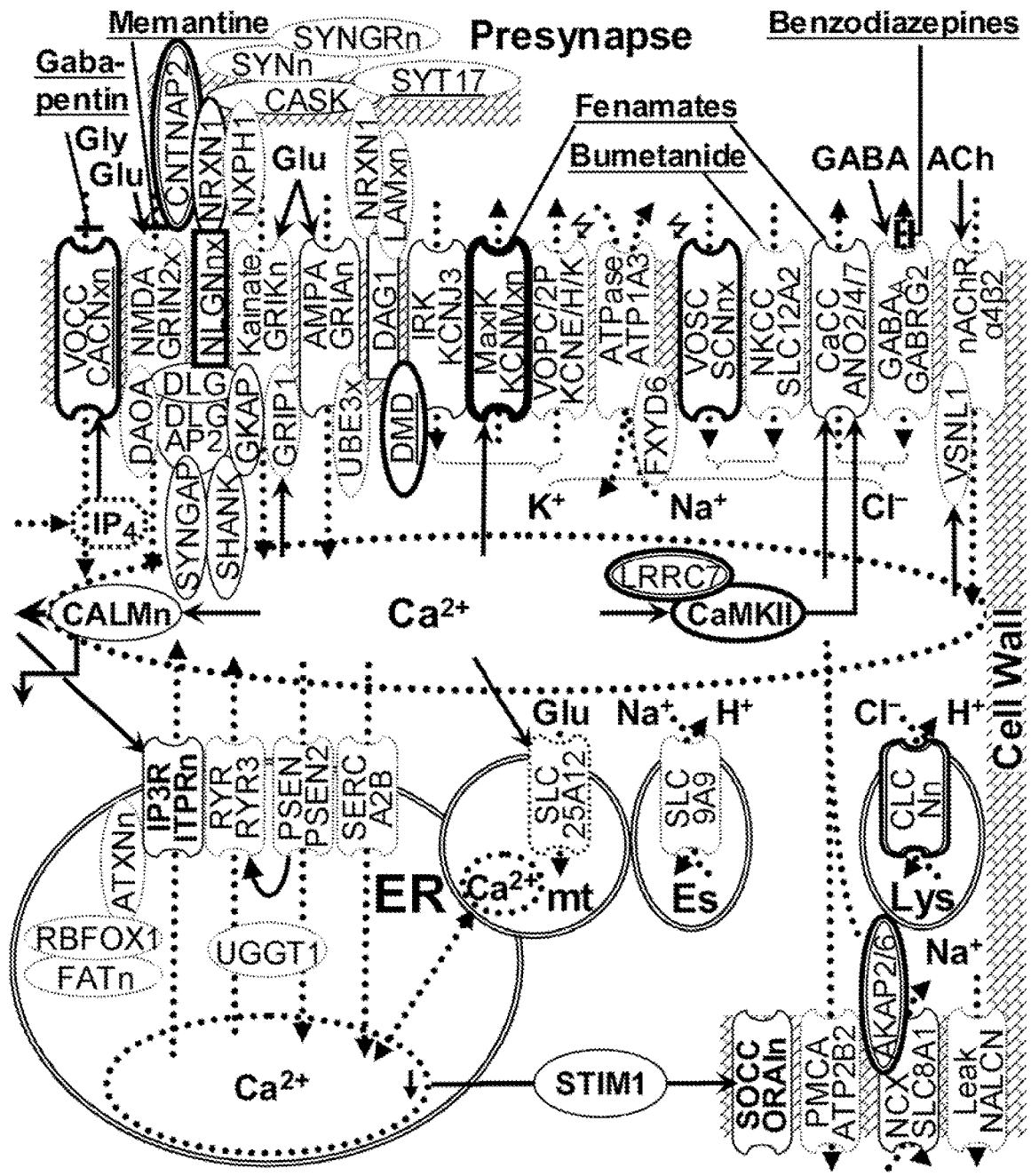

Functional clusters of genes. Several clusters of genes implicated in both of the independent Stages (AGP I (FIG. 2C and FIG. 2D); AGP II (FIG. 2E-FIG. 2F)) consistently overlap with published CAE results (FIG. 2G and FIG. 2H), confirming the involvement of ion channels (FIG. 2D and FIG. 2F, top) and signaling downstream of Ras (FIG. 2C and FIG. 2E, bottom). Notably the present study identifies two additional gene clusters as being associated with ASD. Both Stages implicate several genes involved in deactivation of growth factor (GF) receptors (FIG. 2D and FIG. 2E, top) as ASD-specific risk factors and chloride (Cl⁻) signaling, either through $Ca^{2+}$ activated Cl⁻ channels (CaCC, FIG. 2D, top right) or through genes regulating them (LRRC7, CAMKII) and the lysosomal Cl⁻/H⁺ exchange transporter CLCN7 (FIG. 2F, right).

Figure 2G:
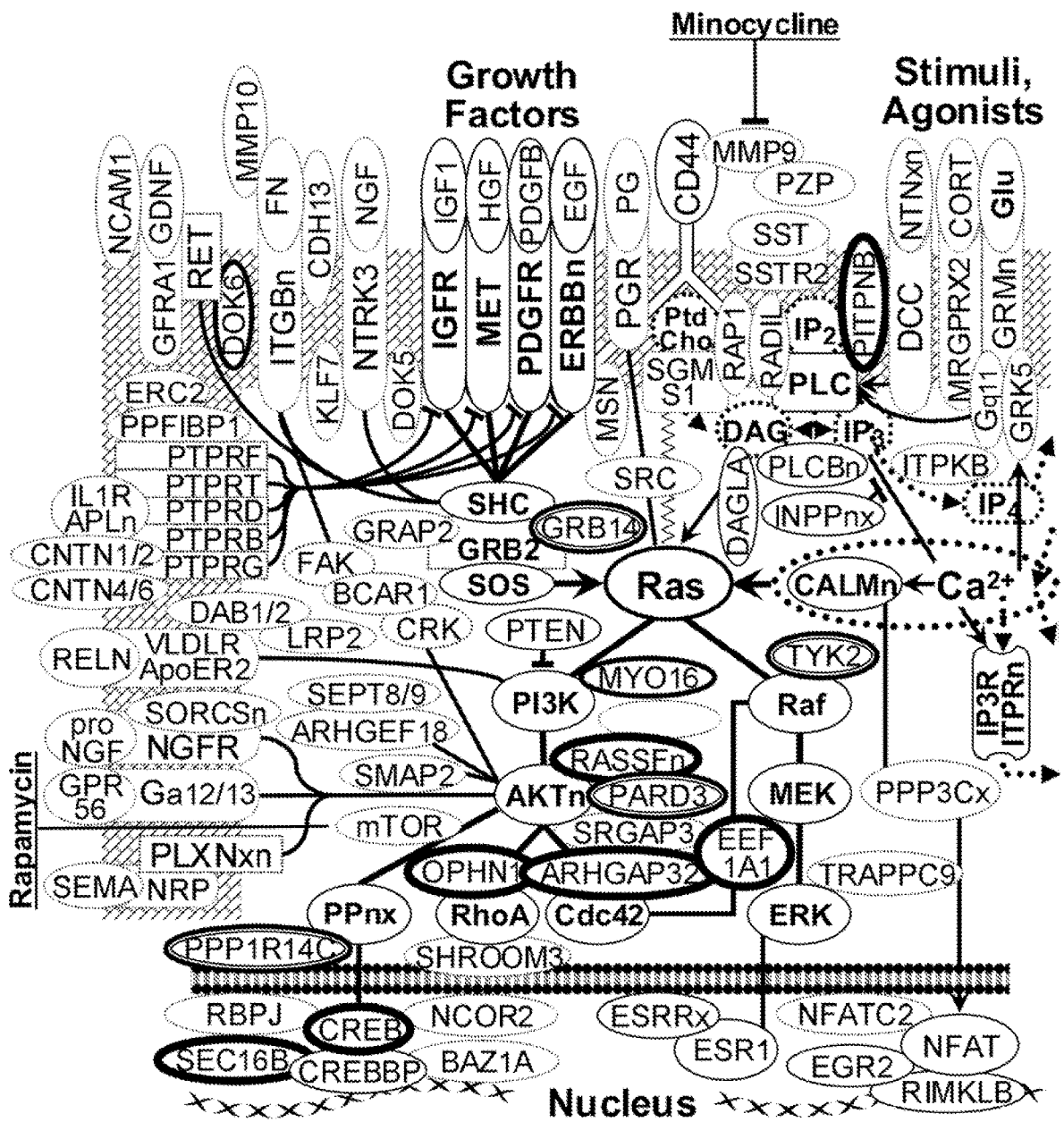
Figure 2H:
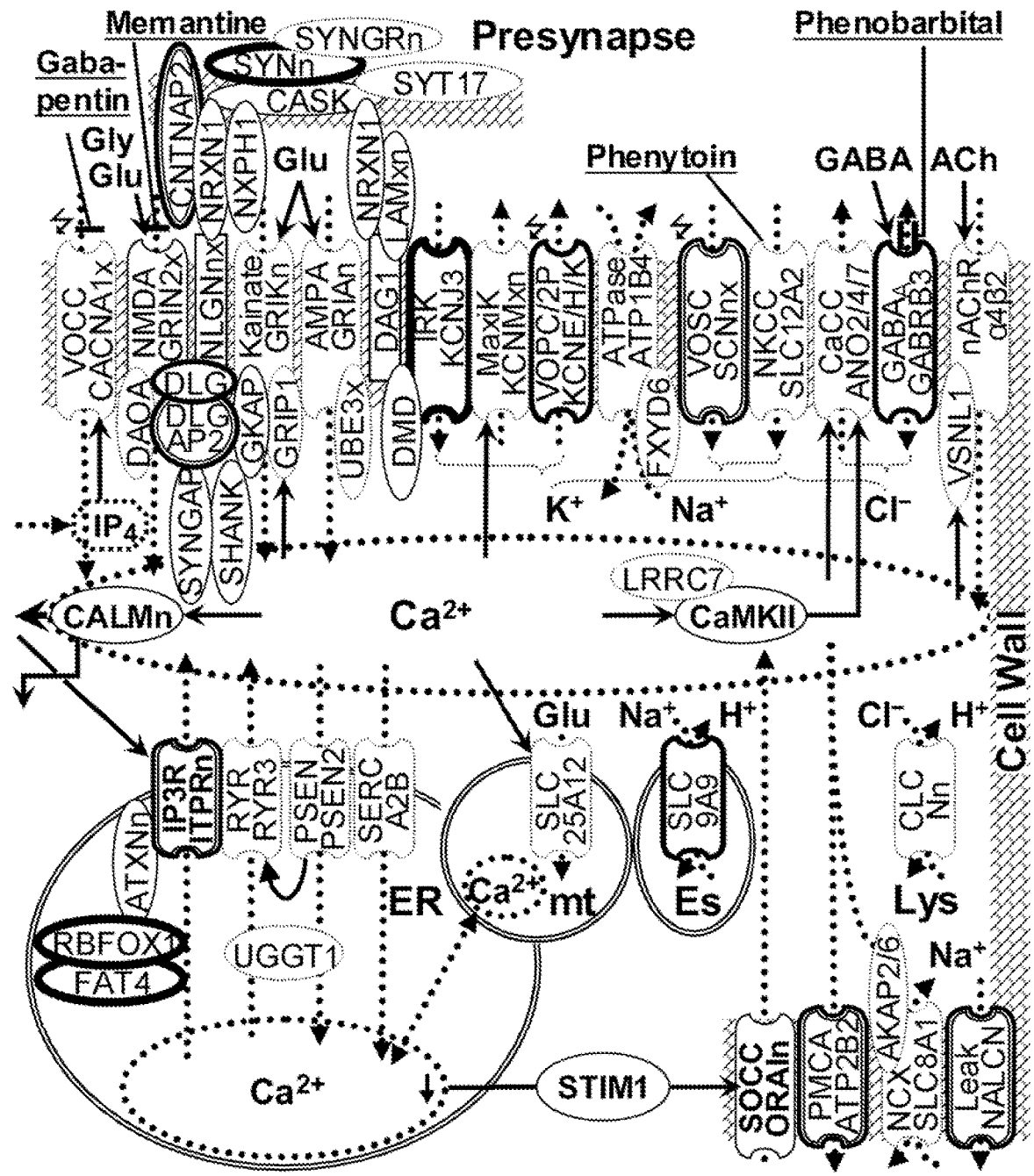

Broad evidence for involvement of PTPRs. One of the most striking observations presented herein is the involvement of at least five PTPRs in ASD, but not in CAE (FIG. 2C and FIG. 2E vs. FIG. 2G). PTPRs (TABLE 2e) regulate growth factor signaling through reversible protein tyrosine dephosphorylation (Tonks N K (2006) *Nat Rev Mol Cell Biol* 7:833-46). PTPRT ($90^{th}/20^{th}$, 8.57) was implicated in ASD by a deletion (Christian S L, Brune C W, et al. (2008) *Biol Psychiatry* 63:1111-7; Table S2 AU018704) and a somatic mutation (Wei X, Walia V, et al. (2011) *Nat Genet* 43:442-6). It is the PTPR most frequently mutated in colon cancer, where all five missense mutations identified reduced phosphatase activity (Wang Z, Shen D, et al. (2004) *Science* 304:1164-6). PTPRD ($519^{th}/84^{th}$, 7.26), for which rare CNVs were previously reported (Pinto D, Pagnamenta A T, et al. (2010) *Nature* 466:368-72) and its ligand (Valnegri P, Montrasio C, et al. (2011) *Hum Mol Genet* 20:4797-809) IL1RAPL2 ($10^{th}$ in AGP II), which is associated with X-linked non-syndromic mental retardation, are also implicated. De novo disruptions in PPFIA1 and the neighboring SHANK2 were recently reported in a person with autistic behavior (Schluth-Bolard C, Labalme A, et al. (2013) *J Med Genet* 50:144-50) and, here, PTPRF is implicated through the association of its interacting binding protein 1 PPFIBP1 ($11^{th}/197^{th}$, 9.14) and ERC2 ($49^{th}$ in AGP II). PTPRG is known to bind both CNTN6 ($13^{th}$ in AGP II) and CNTN4 ($837^{th}/178^{th}$, 7.06) (Bouyain S, Watkins D J (2010) *Proceedings of the National Academy of Sciences* 107:2443-8), both of which play an important role in postnatal brain development (Zuko A, Bouyain S, et al. (2011) *Adv Protein Chem Struct Biol* 84:143-80). PTPRB ($21^{st}/880^{th}$, 7.77) binds CNTN1, which is involved in axonal expression and neurite extension (Shimoda Y, Watanabe K (2009) *Cell Adh Migr* 3:64-70).

TABLE 3

Top 100 genes identified in AGP I and AGP II

| Seq | Gene I | s | SFARI | $s_F$ | Seq II | Gene II | s | SFARI | $s_F$ | Seq I |
|---|---|---|---|---|---|---|---|---|---|---|
| 1 | ANO4 | *** | 6.964 | | | KCNMA1 | *** | 6.979 KCNMA1 | 9.38 | 795 |
| 2 | DOK5 | *** | 6.940 | 9.29 | 497 | HTR1B | | 6.227 HTR1B | 0.00 | |
| 3 | MMP10 | *** | 6.812 | | | SEMA3A/E | ** | 5.901 SEMA5A | 8.72 | 388 |
| 4 | pDGFB | *** | 6.733 | | | HIVEP2 | | 5.811 | 9.22 | 110 |
| 5 | MRGPRX2 | *** | 6.636 | | | IGF1 | ** | 5.747 | 0.00 | |
| 6 | SGMS1 | *** | 6.625 SGSM3 | | | FSTL4 | | 5.719 | 0.00 | |
| 7 | ATP1A3/GRIK5 | *** | 6.621 GRTK2 | | | NMT2 | | 5.717 | 0.00 | |
| 8 | SMAP2 | *** | 6.587 RIMS3 | | | SEPT9 | ** | 5.665 | 9.01 | 123 |
| 9 | ARHGAP48 | *** | 6.546 ARHGAPN | | | NTRK3 | ** | 5.536 NTRK3 | 0.00 | |
| 10 | SORCS2 | *** | 6.443 | 9.85 | 36 | IL1RAPL2 | *** | 5.477 IL1RAPL2 | 0.00 | |
| 11 | pPFIBP1 | *** | 6.376 PTPRx | 9.17 | 197 | TRAPPC9 | ** | 5.464 | 8.04 | 633 |
| 12 | RASSF8 | *** | 6.168 RASSF5 | | | ARHGAP6 | ** | 5.400 ARHGAPn | 0.00 | |
| 13 | MALT1 | | 6.118 | 8.24 | 841 | CNTN6 | *** | 5.391 CNTN6 | 0.00 | |
| 14 | FXYD6 | *** | 6.084 | | | BCOR | | 5.327 | 0.00 | |
| 15 | GPR56 | *** | 5.924 | 8.20 | 620 | EGR2 | ** | 5.247 EGR2 | 0.00 | |
| 16 | BAZ1A | *** | 5.87 | | | LARGE | | 5.183 | 7.97 | 440 |
| 17 | DMD | *** | 5.852 DMD | 8.97 | 88 | TOM1L1 | | 5.158 | 8.36 | 186 |
| 18 | NXPH1 | *** | 5.846 SG | | | PGR | ** | 5.149 | 8.78 | 66 |
| 19 | NTMT1 | | 5.765 | | | PARP1 | | 5.129 | 0.00 | |
| 20 | LRRC16A | | 5.689 | | | PTPRT | ** | 5.066 PTPRT | 8.57 | 90 |
| 21 | pTPRB | ** | 5.644 PTPRx | 7.77 | 880 | CLCN7 | ** | 5.048 | 7.77 | 503 |
| 22 | KLF7 | ** | 5.634 | | | FGF13 | | 5.034 FGFBP3 | 0.00 | |
| 23 | SHROOM3 | ** | 5.607 | 8.66 | 109 | IGFBP7 | ** | 5.009 | 0.00 | |
| 24 | GABRG2 | ** | 5.574 GABRxn | | | IGFBPL1 | ** | 5.007 | 0.00 | |
| 25 | GFRA1 | ** | 5.568 | | | CDH13 | ** | 4.989 CDHn | 8.86 | 45 |
| 26 | ITGB6 | ** | 5.530 | | | RERG | | 4.963 | 0.00 | |
| 27 | SSTR2 | ** | 5.511 | | | RNASEH2B | | 4.933 | 7.54 | 626 |
| 28 | ZFPM2 | | 5.509 | | | CNTNAP2 | ** | 4.933 CNTNAP2 | 0.00 | |
| 29 | KCNJ3 | ** | 5.485 KCNJ105 | | | PPP1R14C | ** | 4.917 PPP1Rnx | 0.00 | |
| 30 | RBPJ | ** | 5.473 | | | SCN7A | ** | 4.915 SCNnA | 0.00 | |
| 31 | FABP1 | | 5.464 FABP74 | | | KPNA3 | | 4.909 | 0.00 | |
| 32 | UGGT1 | ** | 5.455 | | | AKAP2 | ** | 4.908 | 7.31 | 956 |
| 33 | VSNL1 | | 5.433 | | | UBE2V1/CEBPB | | 4.880 | 0.00 | |
| 34 | PZP | ** | 5.432 | 8.56 | 93 | CD207 | | 4.873 | 0.00 | |
| 35 | ANKRD1 | | 5.427 ANKRD11 | | | LRP1 | ** | 4.851 | 0.00 | |
| 36 | GRK5 | ** | 5.424 | 8.68 | 59 | SORCS2 | ** | 4.836 | 9.85 | 10 |
| 37 | CHST8 | | 5.415 CHST11 | | | EDG1 | | 4.813 | 0.00 | |
| 38 | CACNA1S | ** | 5.403 CACNA1x | | | IRF8 | | 4.775 | 0.00 | |
| 39 | SYNGR1 | ** | 5.385 | 7.53 | 871 | ARHGAP10 | ** | 4.762 ARHGAPnx | 7.37 | 636 |
| 40 | PPP1R1C | ** | 5.377 PPP1Rnx | | | SRGAP3 | ** | 4.752 | 0.00 | |

TABLE 3-continued

Top 100 genes identified in AGP I and AGP II

| Seq | Gene I | s | SFARI | $s_F$ | Seq II | Gene II | s | SFARI | $s_F$ | Seq I |
|---|---|---|---|---|---|---|---|---|---|---|
| 41 | ESR1 | ** | 5.359 ESR1 | | | DEFB110 | | 4.745 | 0.00 | |
| 42 | BCAR1 | ** | 5.348 | | | PDE2A | | 4.733 PDEnx | 0.00 | |
| 43 | NPR3 | | 5.346 | | | GPC5 | | 4.712 GPCn | 0.00 | |
| 44 | RELN | ** | 5.334 RELN | | | PLB1 | | 4.707 | 0.00 | |
| 45 | CDH13 | ** | 5.266 | 8.86 | 25 | DAB1 | ** | 4.704 DAB1 | 7.56 | 399 |
| 46 | KCNE2 | ** | 5.252 | | | FMN1 | | 4.700 | 0.00 | |
| 47 | INPP4B | ** | 5.252 INPP1 | | | SORCS1 | ** | 4.686 | 0.00 | |
| 48 | DAOA | ** | 5.221 | | | RAP1A | ** | 4.681 | 0.00 | |
| 49 | OR1N1/2 | | 5.184 | | | ERC2 | ** | 4.680 | 0.00 | |
| 50 | HOXA1 | | 5.162 HOXA1 | | | PSG9 | | 4.674 | 0.00 | |
| 51 | SOX5 | | 5.158 | | | EPHA2 | | 4.673 | 0.00 | |
| 52 | NTN4 | * | 5.145 | 7.39 | 698 | LRRC7 | | 4.673* | 0.00 | |
| 53 | ITPKB/PSEN2 | * | 5.113 | | | ABTB2 | | 4.664 | 0.00 | |
| 54 | GYPC | | 5.077 | | | LIF/OSM | | 4.659 | 0.00 | |
| 55 | VCX2/3A | | 5.077 | 7.33 | 691 | CAMK2A | | 4.651* | 0.00 | |
| 56 | UBE2K | | 5.074 | | | ESRRG | | 4.651* | 0.00 | |
| 57 | EEF1E1 | | 5.072 | | | LPHN2 | | 4.641 | 7.46 | 433 |
| 58 | DSC1/2/3 | | 5.063 | 7.52 | 452 | BICD1 | | 4.640 | 0.00 | |
| 59 | LHX6 | | 5.061 | | | GRK5 | | 4.639* | 8.68 | 36 |
| 60 | GALNT10 | | 5.061 | | | PTHLH | | 4.623 | 0.00 | |
| 61 | LMO4 | | 5.059 | 7.36 | 634 | CENTD1 | | 4.618 | 0.00 | |
| 62 | PLXNC1 | * | 5.041 | 7.30 | 690 | GJB6 | | 4.616 | 0.00 | |
| 63 | CGNL1 | | 5.037 | 7.70 | 305 | TMEFF2 | | 4.615 | 0.00 | |
| 64 | SLC8A1 | * | 5.036 | | | ARHGAP44 | | 4.613* | 0.00 | |
| 65 | ABCC4 | | 5.027 | | | CTNNA3 | | 4.608 | 0.00 | |
| 66 | PGR | * | 5.023 | 8.78 | 18 | AKAP6 | | 4.603* | 0.00 | |
| 67 | KCNK9 | * | 5.022 | | | NPAS3 | | 4.602 | 7.23 | 631 |
| 68 | ABCC13 | | 5.018 | | | AMHR2 | | 4.599 | 0.00 | |
| 69 | ARHGAP42 | * | 5.006 | 7.75 | 249 | RIMKLB/A2ML1 | | 4.592* | 0.00 | |
| 70 | IL10RA | | 4.992 | | | FHIT | | 4.592 | 7.77 | 210 |
| 71 | ANO7 | * | 4.992 | | | ERBB4 | | 4.592* | 7.15 | 727 |
| 72 | SLC9A9 | * | 4.980 | | | NLGN2/FGF11 | | 4.589* | 0.00 | |
| 73 | ELMO1 | | 4.970 | 7.69 | 262 | CACNA1A | | 4.586* | 0.00 | |
| 74 | GSG1L | | 4.956 | | | NPTX1 | | 4.586 | 0.00 | |
| 75 | KCNH8 | * | 4.954 | | | SLIT3 | | 4.586 | 0.00 | |
| 76 | pRKCI | * | 4.949 | | | COL24A1 | | 4.582 | 0.00 | |
| 77 | CRYZ | | 4.923 | | | ZNF496 | | 4.578 | 0.00 | |
| 78 | ARFGAP3 | * | 4.922 | | | CNTN4 | | 4.575* | 7.06 | 837 |
| 79 | MACROD2 | | 4.913 | 7.85 | 155 | RPS6KA3 | | 4.575 | 0.00 | |
| 80 | BNC2 | | 4.913 | 7.13 | 766 | MARCO | | 4.572 | 0.00 | |
| 81 | ELP3 | | 4.913 | | | EIF4G3 | | 4.571* | 0.00 | |
| 82 | ODZ4 | | 4.910 | | | WDR65 | | 4.553 | 0.00 | |
| 83 | ENC1/HEXB | | 4.907 | 7.77 | 190 | BMPER | | 4.546 | 7.13 | 694 |
| 84 | VPS13B | | 4.903 | | | PTPRD | | 4.530* | 7.26 | 519 |
| 85 | UBXN7 | | 4.902 | | | RNF152 | | 4.524 | 0.00 | |
| 86 | CLPB | | 4.893 | | | NRSN1 | | 4.523 | 0.00 | |
| 87 | MFI2 | | 4.892 | | | CSMD1 | | 4.521 | 7.67 | 218 |
| 88 | ECM2 | | 4.890 | | | DMD | | 4.517* | 8.97 | 17 |
| 89 | PLCB2 | * | 4.889 | | | NOVA1 | | 4.517 | 0.00 | |
| 90 | PTPRT | | 4.887 | 8.57 | 20 | AGR2/3 | | 4.516 | 0.00 | |
| 91 | CACNA1C | * | 4.870 | | | TINAG | | 4.516 | 0.00 | |
| 92 | CIAPIN1/COQ9 | | 4.860 | | | DAGLA | | 4.513* | 0.00 | |
| 93 | PCSK5 | | 4.858 | | | PZP | | 4.510* | 8.56 | 34 |
| 94 | NCAM1 | * | 4.856 | 7.04 | 844 | RADIL | | 4.507* | 0.00 | |
| 95 | MB | | 4.853 | | | CHD7 | | 4.501 | 7.81 | 161 |
| 96 | PHACTR3 | | 4.851 | | | ANKRD15 | | 4.497 | 0.00 | |
| 97 | LRPPRC | | 4.849 | | | DAB2 | | 4.491* | 0.00 | |
| 98 | SYNPO2 | | 4.848 | | | GRAP2 | | 4.487* | 0.00 | |
| 99 | ATAD3A/B/C | | 4.847 | | | TMEM47 | | 4.486 | 0.00 | |
| 100 | KCNK5 | * | 4.839 | | | ARSJ | | 4.479* | 6.88 | 999 |

Figure 3A:
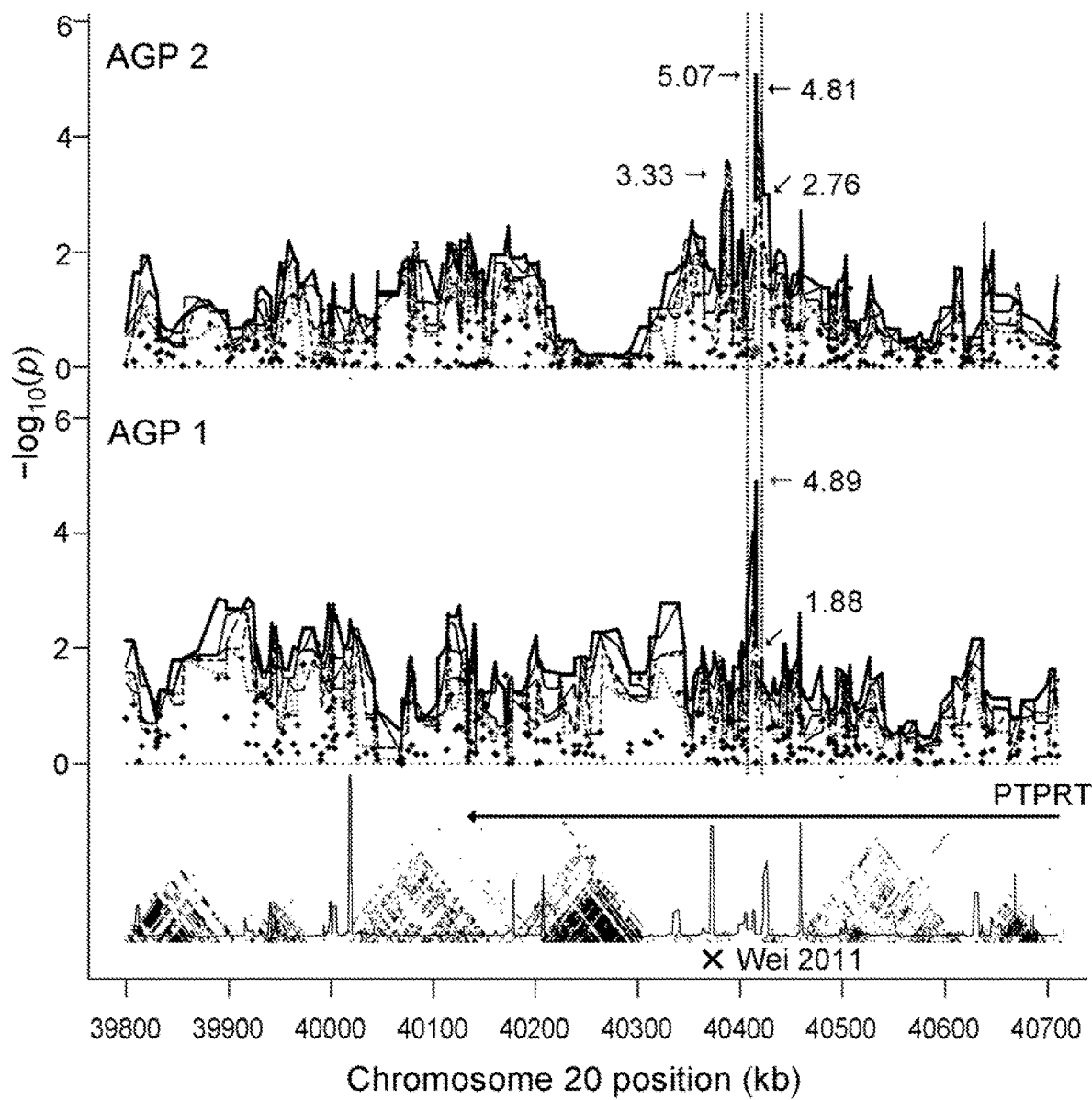
FIG. 3A-FIG. 3D: Extended regional Manhattan plot of μGWAS results for PTPRT (FIG. 3A and FIG. 3B), PPFIBP1 (FIG. 3C), and PTPRB (FIG. 3D) by AGP stage. X-axis is base pairs within chromosome. Black dots indicate significance in ssGWAS, lines indicate significance in diplotypes of width 2 (dotted)-6 (solid). Below the panels are gene annotations, LD blocks, and recombination rate from Hap-Map ((2007) Nature 449:851-61). s-Values shown indicate the results for the most significant region (horizontal arrows) and the univariate results for the SNPs within the most significant region (diagonal arrows). The SNPs in the most significant region within PTPRT are: rs6102794, rs6072693, rs6072694, rs6102795, rs6016759, and rs6102798. The "x" and box at the bottom indicate a previously reported somatic mutation at rs146825584 (Wei X, Walia V, et al. (2011) *Nat Genet* 43:442-6) and a deletion at 41,036,259-41,300,521 (Christian S L, Brune C W, et al. (2008) *Biol Psychiatry* 63:1111-7), respectively. The SNPs in the most significant region within PTPRB are: rs3782377, rs2567137, rs2567133, rs2278342, rs2116209, rs2278341.
Figure 3B:
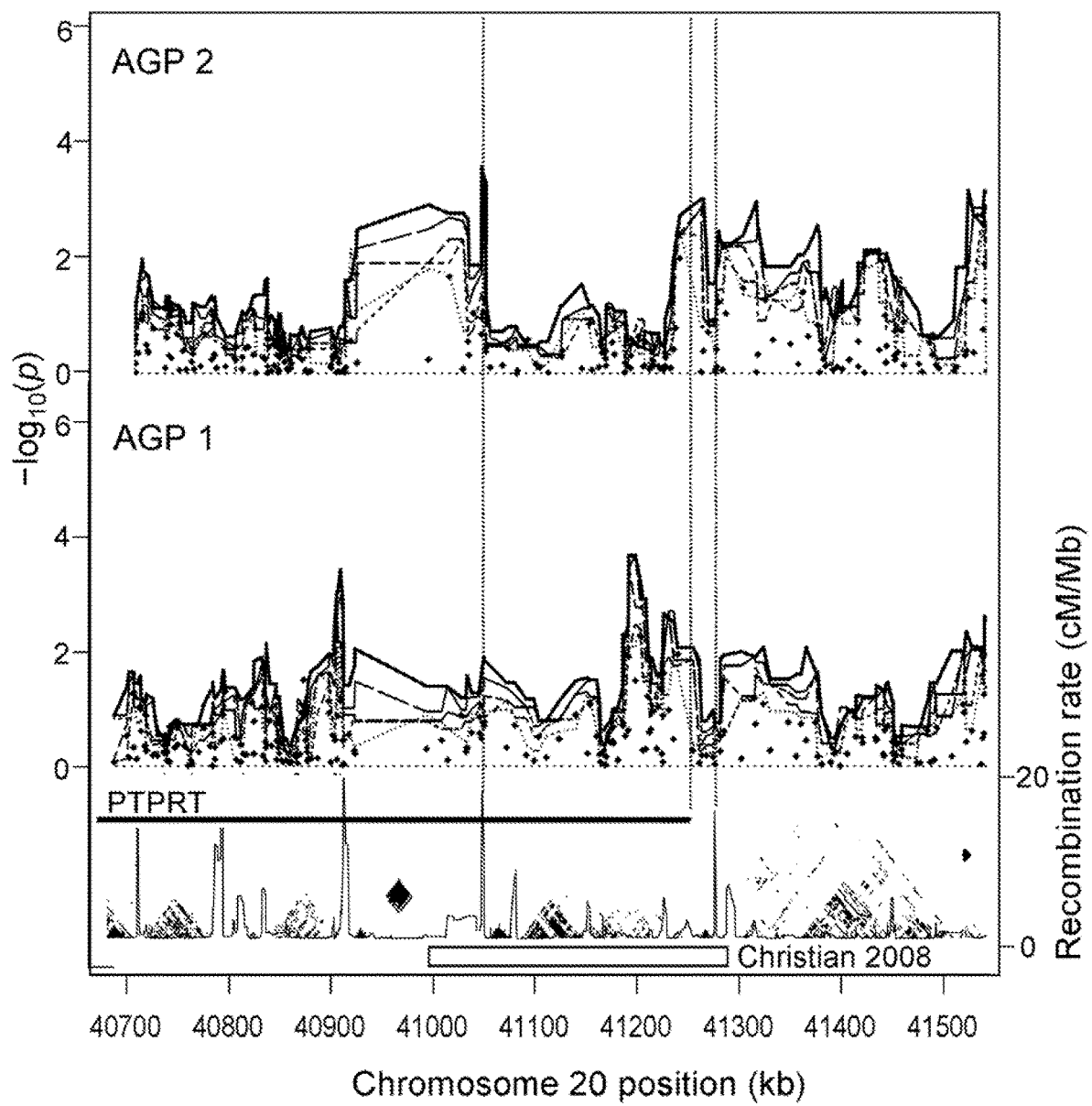
Figure 3C:
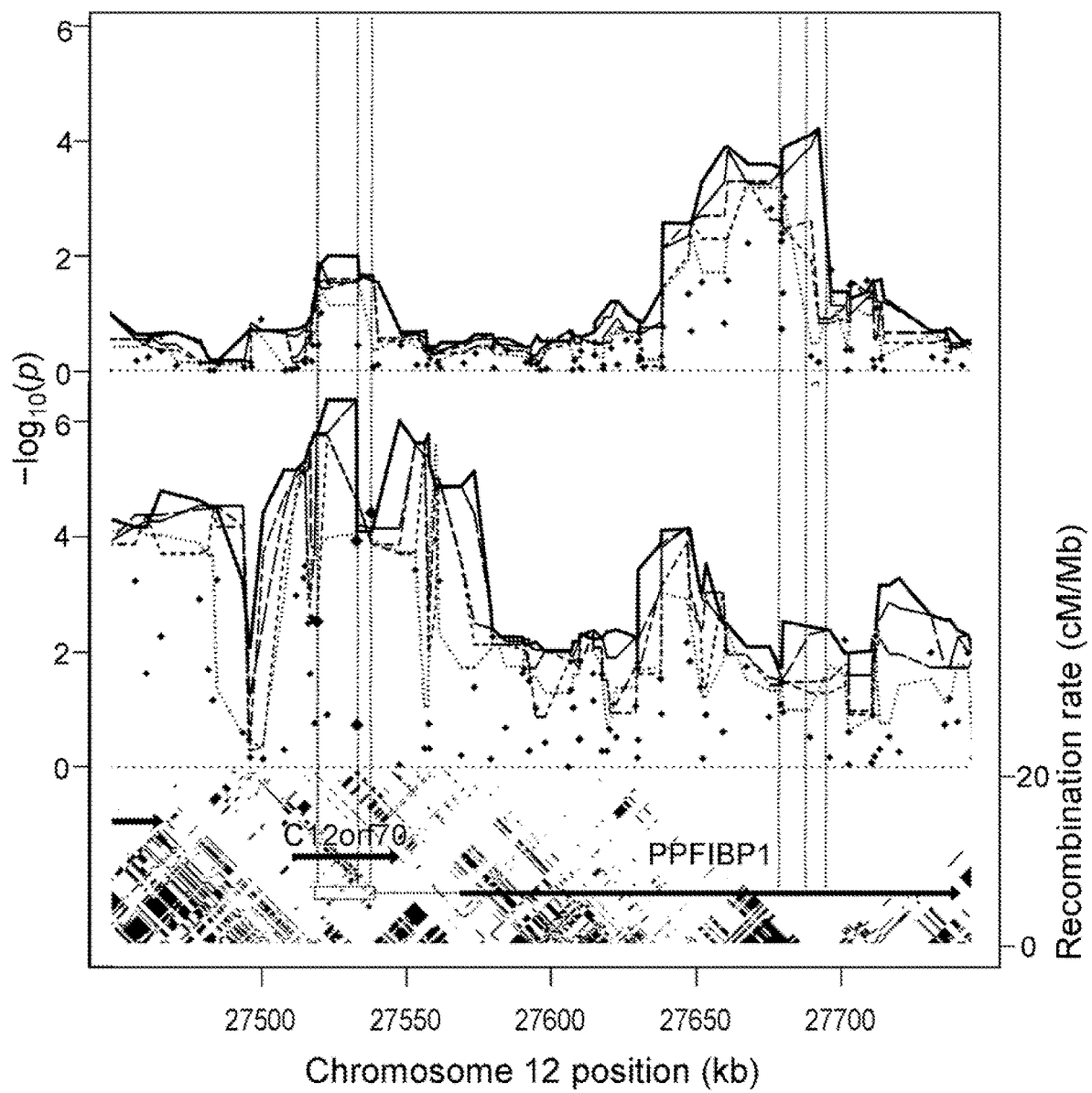
Figure 3D:
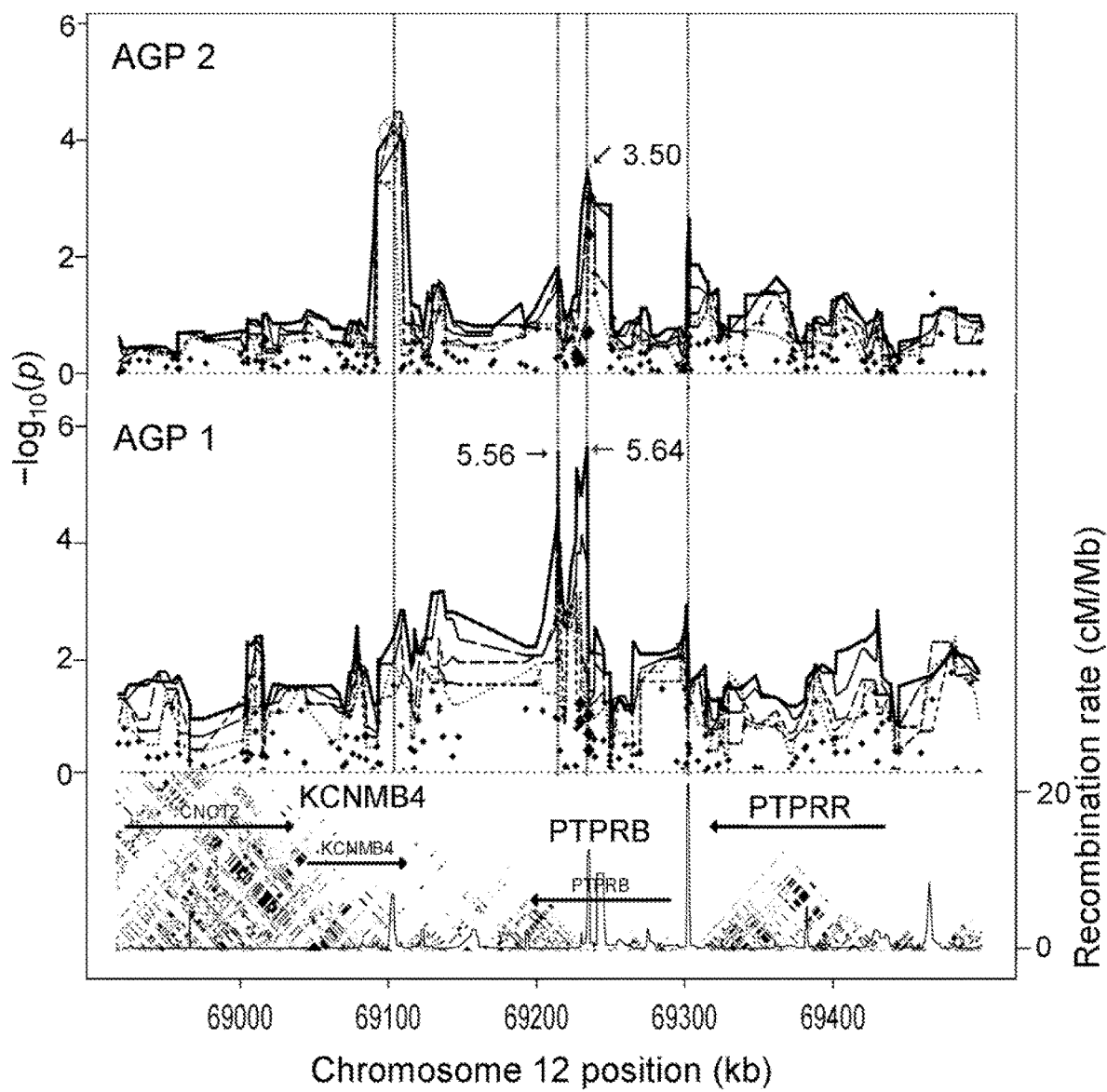
Figure 4:
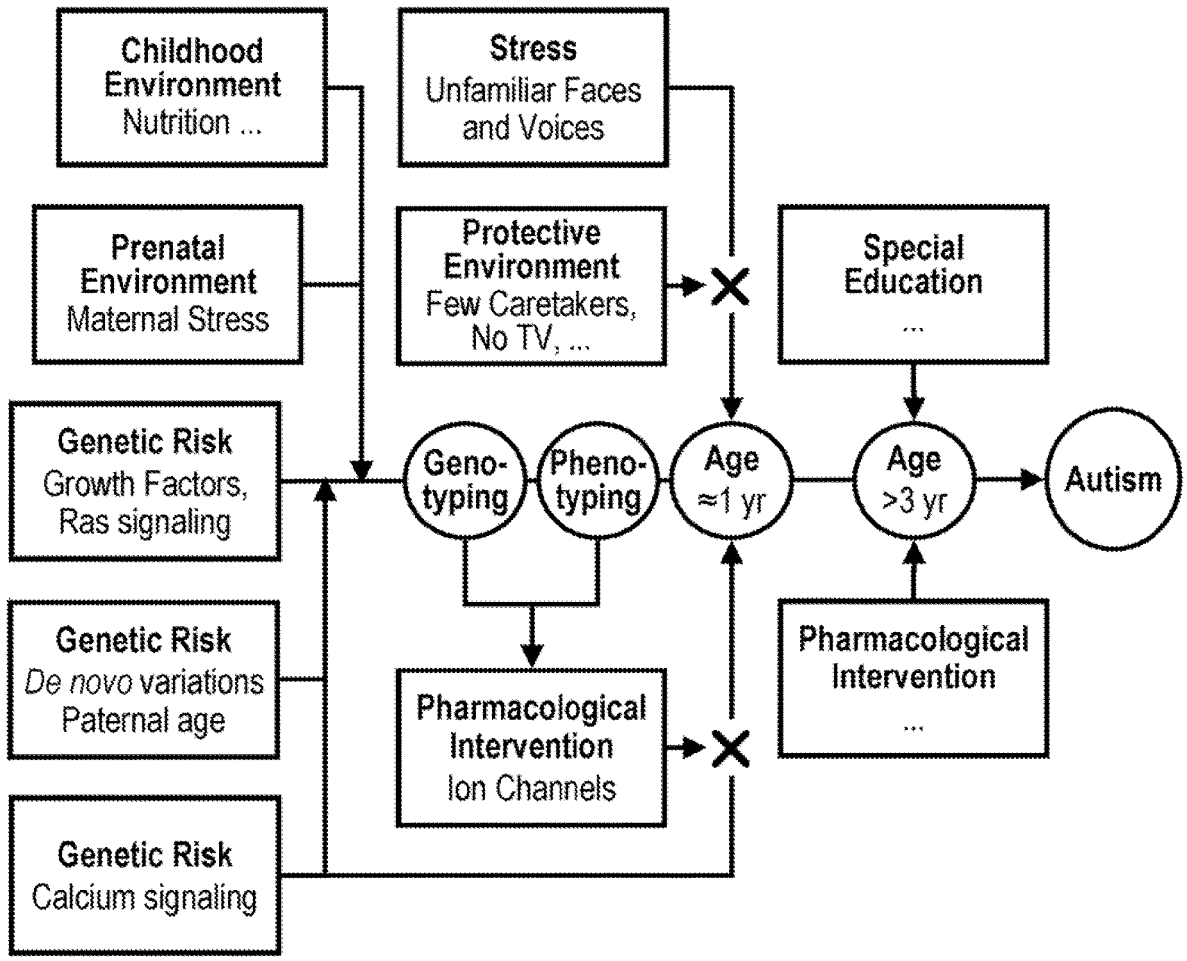
FIG. 4: Hypothesized interventions to prevent regression in children with ASD. During the critical period of developing cortical structures for social interactions the risk of stress-induced regression might be reduced through a combination of strategies including a protective environment where exposure to unfamiliar faces is limited and pharmacological interventions to reduce hyperexcitability related to $Ca^{2+}$ signaling by targeting ion channels determined through genetic testing of genes known to be involved in $Ca^{2+}$ signaling among children with a risk phenotype.

Table 3, above shows the top 100 regions by μGWAS in AGP I (left) and AGP II (right) and most closely related genes in SFARI Gene. The top 41 genes are included in FIG. 1. Genes highlighted as *, , and *, are included in FIGS. 2C and 2D and FIGS. 2E and 2F, for AGP I and AGP II, respectively. Columns Seq II and Seq I, respectively indicate the rank order of the same gene in the other Stage. $s_F$: Fisher($s_{AGP\ I}$, $s_{AGP\ II}$). Replication of individual PTPR wide loci across the independent Stages. Notably, the region of high significance in two of the PTPRs, PTPRT (FIGS. 3A and 3B) and PTPRB ($21^{st}/880^{th}$, 9.11) (FIG. 3D) comprises the same SNPs in both independent Stages. Moreover, the PTPRT region is located in the same LD block as a known somatic mutation (rs146825584) (Wei X, Walia V, et al. (2011) *Nat Genet* 43:442-6).

Evidence for PTPR risk being epistatic. To further explore the risk conveyed by PTPRs, male subjects were scored combined with 1047 male controls from a melanoma study genotyped on the same chip platform stratified by Stages (Wittkowski K M (1988) *J Am Statist Assoc* 83:1163-70, 87:258). The polarized diplotypes with the best discrimination by Stage in are highly consistent, indicating that the populations agree not only in the location of the risk factors, but also in the high risk alleles.

For PTPRT and PTPRB in both Stages and for PTPRD and PPFIBP1 in AGP I, the SDA and HFA cases scored higher and lower than the controls, respectively, so that no difference could have been detected by comparing all cases against controls. This result is consistent with the hypothesis that PTPR variations, in general, merely affect body size (and, thus, are not selected against), but in the presence of other genetic risk factors contribute significantly to deciding the fate of an ASD case towards either HFA or SDA.

Potassium and chloride ion channels as novel drug targets. Aside from PTPRs (FIG. 2D and FIG. 2E, left) as a risk factor for protracted GF signaling, these results suggest a second functional cluster of genes, involved in Cl⁻ transport and signaling, as specific to ASD (TABLE 2f). In AGP I, the CaCCs ANO4 and ANO7 scored $1^{st}$ and $70^{th}$, respectively (FIG. 2D). In AGP II, the lysosome membrane H⁺/Cl⁻ exchange transporter CLCN7 scored $21^{st}$, followed by CAMK2A, which regulates anoctamins (Verkman A S, Galietta L J V (2009) *Nat Rev Drug Discov* 8:153-71) ($55^{th}$), and LRRC7 (densin-180), which regulates CAMK2A (Robison A J, Bass M A, et al. (2005) *J Biol Chem* 280:35329-36) (FIG. 2F). The role of the anoctamins in pathophysiology is not well understood, except that CaCC activity in some neurons is predicted to be excitatory (Herault J, Petit E, et al. (1995) *Am J Med Genet* 60:276-81), in general, and to have a role in neuropathic pain or nerve regeneration. CaCCs have also been suggested as a direct link with "neurite (re)outgrowth" (Boudes M, Scamps F (2012) *Front Mol Neurosci* 5:35).

ANO2 and ANO6 are associated with panic disorder and major depressive disorder, respectively. ANO3, ANO4, ANO8, and ANO10, but not ANO1, are also expressed in neuronal tissue (Kunzelmann K, Tian Y, et al. (2011) *Pflügers Archiv European Journal of Physiology* 462:195-208). As "druggable channels", anoctamins "may be ideal pharmacological targets to control physiological function or to correct defects in diseases" (Berg J, Yang H, et al. (2012) *Journal of Cell Science* 125:1367-71). Few drugs, however, are known to target individual anoctamins or even exclusively CaCCs. Cl⁻ channel blockers such as fenamates, for example, may decrease neuronal excitability by activating $Ca^{2+}$-dependent outward rectifying K⁺ channels.

Finally, the HFA and SDA cases were compared individually against all parental controls (stratified by sex) in the larger AGP I population. Overall, the level of significance is lower and the enrichment is less pronounced, especially for the SDA cases, as expected when cases and some controls are related. For the HFA cases, however, a second anoctamin, the panic and depression associated ANO2, located on the other arm of chromosome 12, competes with ANO4 (FIG. 1A and FIG. 1B), for the most significant gene among the result. Hence, drugs targeting anoctamins, or other chloride and/or potassium channels, might have broader benefits for the treatment of ASD than in preventing progression to more severe forms of autism.

Discussion

When applied to the AGP data, the consistent results from the hypothesis-driven prioritized subset analysis of two independent populations presented herein strongly confirm the Ras/$Ca^{2+}$ hypothesis, and provide, evidence-based insights into the etiology of ASD, a novel treatment paradigm, and additional approved drugs that might be repurposed for ASD. For example, the results presented herein provide, for the first time, evidence of an association of chloride and potassium channels with ASD. In addition, the results presented herein suggest that protracted growth factor signaling may be associated with ASD, such that early clinical intervention, for example using treatment with ion channel modulators, might be effective in early childhood while neuronal growth and pruning is occurring.

The results presented herein suggest that a shift in focus may be required from intervention in school aged children to intervention starting at much earlier stages while the neural circuitry is being shaped and refined, for example in response to social stimuli. Drugs that target ion channels may decrease hyperexcitation to a level where a child does not feel the need to withdraw from social interaction. Identifying children at high risk of progression through genetic testing, for example for mutations in PTPRs and related genes or other autism or ASD-associated genes, could help identify subjects for whom early clinical intervention may be warranted. For example, testing at marker diplotypes in ion channels or related genes could serve to personalize the choice of the medication most effective in reducing excessive excitation of the Ras pathway during the critical period. For example, gabapentin, approved by the FDA for the treatment of partial seizures in children from three years of age (Parke-Davis (2013) Medication Guide Neurontin. New York, N.Y., Pfizer: 32-7) and tested in population-pharmacokinetic studies including subjects starting from age one month (Ouellet D, Bockbrader H N, et al. (2001) *Epilepsy Res* 47:229-41), might be repurposed for children with autism or ASDs, such as those with mutations in VOCCs. Similarly, drugs targeting the CaCCs identified herein, such as fenamates, which have so far been considered in pain, in general, and (menstrual) migraines (Pringsheim T, Davenport W J, et al. (2008) *Neurology* 70:1555-63) in particular, as well as in epilepsies for decreasing excitatory synaptic activity and reducing neuronal excitability (Fernandez M, Lao-Peregrin C, et al. (2010) *Epilepsia* 51:384-90; Yau H J, Baranauskas G, et al. (2010) *J Physiol* 588:3869-82), might also be repurposed for treatment of autism or ASDs, for example in subjects with mutations involving Cl⁻ signaling. MFA has been used in preterm children (Ito K, Niida Y, et al. (1994) *Acta Paediatr Jpn* 36:387-91) and, in the UK, is recommended for use in infants starting at six months of age (Heads of Medicines Agencies UK (2012)). Fenamates target a variety of potassium and chloride channels (Greenwood I A, Leblanc N (2007) *Trends Pharmacol Sci* 28:1-5) and, thus, may have less systemic side effects (including hypokalaemia (Ng T M, Konopka E, et al. (2013) *J Cardiovasc Pharmacol Ther* 18:345-53)) than the drugs that inhibit Cl⁻ influx via the Na⁺—K⁺-2Cl⁻ co-transporter NKCC1, which have been shown to improve symptoms of ASD in some cases (Lemonnier E, Degrez C, et al. (2012) *Transl Psychiatry* 2:e202).

The results presented in this Example attest to a broad spectrum of genetic risk factors contributing to ASD. For example, the results presented herein suggest that various factors other than variations in PTPRs might sensitize the Ras pathway to hyperexcitation by interfering with growth factor downregulation. Hence the proposed interventions might prevent a substantial proportion of children with various risk factors for ASD from developing along the more severe spectrum of this heterogenic disease. The overlap in genetic risk factors between ASD and CAE suggests another potential benefit of the proposed early intervention. As neonatal seizures per se may cause long-term neurological problems (Nardou R, Ferrari D C, et al. (2013) *Semin Fetal Neonatal Med* 18:175-84), preventing the postulated intolerable experiences may positively affect a wider range of ASD symptoms.

Example 2

Treatment and Prevention of ASD in Young Children

The data presented in Example 1 identified two autism-specific gene clusters along the Ras/Ca$^2$ pathway. One cluster comprises several receptor protein tyrosine phosphatases (PTPRs), whose role is to deactivate growth factors shortly after their activation through growth factor binding. The second cluster, including ANOs (anoctamins) and CLCs (voltage-sensitive chloride channels) shifts the focus from only Ca$^{2+}$ signaling to a broader spectrum of ions, including CF and K.

Excessive neuronal growth through impaired control of growth signaling may explain the larger brain and body sizes seen in children with severe forms of autism (Pathan A R, Karwa M, et al. (2010) *Inflammopharmacol* 18:157-68), and, importantly, may leave neurons overly sensitive to stimulation via the second messenger Ca$^{2+}$. The suggested role of PTPR variations in protracted growth factor (GF) signaling suggests that pharmaceutical interventions targeting excitatory signaling should be started in very early childhood when rapid neural development is occurring, for example from 6-12 months of age, the same time where language regression is seen in some children at the beginning of the 'stranger anxiety' period, or even earlier.

A shift in focus may be required from starting intervention in school aged children to starting intervention at much earlier ages during which time children shape and refine their neural circuitry in response to social stimuli (Siller S S, Broadie K (2012) *Neural Plast* 2012: 124548). According to the present invention, drugs targeting ion channels may decrease hyperexcitation to a level where a child does not feel the need to withdraw from social interaction. For example, according to the present invention, gabapentin, approved by the FDA for the treatment of partial seizures in children from 3 years of age (Parke-Davis (2013) Medication Guide Neurontin. New York, N.Y., Pfizer: 32-7) and tested in population-pharmacokinetic studies included subjects starting from one month of age (Ouellet D, Bockbrader H N, et al. (2001) *Epilepsy Res* 47:229-41), can be repurposed for children at risk of developing autism or an ASD, or exhibiting one or more indicators or symptoms of autism or an ASD. For example, such children may have mutations in VOCCs. Similarly, since the results described in Example 1 herein suggest that mutations involving K$^+$ and Cl$^-$ signaling may be associated with ASD, fenamates, which have so far been used or considered for treatment of pain, including (menstrual) migraines (Pringsheim T, Davenport W J, et al. (2008) *Neurology* 70:1555-63), as well as epilepsies for decreasing excitatory synaptic activity and reducing neuronal excitability (Fernandez M, Lao-Peregrin C, et al. (2010) *Epilepsia* 51:384-90; Yau H J, Baranauskas G, et al. (2010) *J Physiol* 588:3869-82), can also be repurposed for treatment or prevention of autism or ASD. The fenamate mefenamic acid (MFA) has been used in preterm children (Ito K, Niida Y, et al. (1994) *Acta Paediatr Jpn* 36:387-91) and, in the UK, is recommended for use in infants starting at six months of age (Heads of Medicines Agencies UK (2012)).

MFA and/or gabapentin (either alone or in combination) or a placebo can be administered to children at high risk of developing autism or ASD, such as male siblings of children with ASD, starting at the time where first symptoms of regression are observed, which is expected to be around the age of 12 months, or earlier. Differences in eye tracking, galvanic skin (skin conductance), and/or EEG response following exposure to pictures of familiar vs. unfamiliar faces between different treatment groups can be assessed after two weeks of either intervention in randomized sequence. From a standard power calculation based on the binomial distribution for this 'sign test' (Dixon W J, Mood A M (1946) *J Am Statist Assoc* 41:557-66; Fleiss J L, Levin B (1988) *J Clin Epidemiol* 41:727-30), a sample size of 50 subjects with early symptoms of regression will have 80% power to detect a 0.2 difference in response (0.7 vs. 0.5) at the conventional 5% level.

To explore potential risk/prognostic factors, samples can be taken from parents, the affected sibling, and the study subject and these samples can be genotyped or sequenced. A combination of family-based and cohort analysis, both using novel computational biostatistics approaches, can be used to identify genetic risk/predictive factors, including, but not limited to mutations in PTPRs/ANOs.

Example 3

Use of Mefenamic Acid in Autism Spectrum Disorders

Age for intervention: The window of opportunity for reducing the incidence of severe forms of autism may commence in very early stages of childhood development. The involvement of PTPRs suggests that treatment may be more effective if performed during the time of active neural development. For example, treatment may be more effective if completed before around 24 months, when some studies suggest that synaptogenesis in language-related areas ceases (Tau G Z, Peterson B S (2010) *Neuropsychopharmacology* 35:147-68.

With early treatment using the methods and compositions of the present invention regression may be averted, allowing other treatments targeting specific sub-phenotypes to be employed, later, if desired. For example, including bumetanide (Lemonnier E, Degrez C, et al. (2012) *Transl Psychiatry* 2:e202) and oxytocin (Preti A, Melis M, et al. (2014) *J Child Adolesc Psychopharmacol* 24:54-68) or, potentially, memantine. Similarly, treatment with the compositions of methods of the present invention may also be continued even if early treatment has already prevented regression.

Intervention: While, in principle, one could compensate for lack of dephosphorylation of GF receptors through PTPRs by blocking GF receptors with drugs like Gleevec® (imatinib), in young children the risk of interfering with GF receptors may be unacceptable, especially at stages when no definite diagnosis can yet be made, even if the majority of children with prodromal signs seen in eye-tracking is expected to develop toward the severe end of the spectrum. However, the ion channel modulators described herein have been used safely in children for decades to treat, e.g., arthritis and epilepsies.

MFA was introduced in the early 1960s as an NSAID and has been approved in the U.K. for the treatment of juvenile arthritis from 6 months (Heads of Medicines Agencies UK (2012)). In the U.S., MFA is approved for the treatment of pain and menstrual migraines, which have a poor response to analgesics (Pringsheim T, Davenport W J, et al. (2008) *Neurology* 70:1555-63). Only in the 1990s was it discovered that MFA exerts part, if not most, of its effect by reducing neuronal excitability through opening K$^+$ and modulating Cl$^-$ channels. (Peretz A, Degani N, et al. (2005) *Mol Pharmacol* 67:1053-66; Peretz A, Degani-Katzav N, et al. (2007) *PLoS One* 2:e1332)

In the present Example, MFA is administered to young children, for example from birth to two or three-years in age, in order to modulate (K⁺/Cl⁻) ion channels. Such treatments could prevent children from experiencing 'stranger anxiety' and intolerable 'migraine-like' events, and they may continue to speak and interact with people, rather than 'tuning out'. In turn, their brain regions for speech and eye-contact could be sufficiently stimulated to prevent them from being 'pruned', for example beginning at around the third year of life.

In the U.K., MFA has been used since the 1960s in children from 6 months of age at the proposed dose. Children with juvenile idiopathic arthritis (JIA) have been treated chronically without raising any safety concerns. Hence, doses, biological activity, tolerability, and feasibility of administering a MFA oral suspension in the at risk population are well established. Primary endpoints that can be used to assess the efficacy of treatment—for example progress in language development—are also firmly established. Prodrugs of mefenamic acid (MFA) have been shown to decrease the most frequent adverse events associated with MFA, such as transient GI disturbances. (Shah K, Shrivastava S K, et al. (2014) *Pak J Pharm Sci* 27:917-23).

Example 4

Mefenamic Acid Prodrug

The present Example describes an example of a fenamate prodrug, specifically a mirror prodrug comprising of two molecules of mefenamic acid (MFA) linked via a disulfide linker at the carboxyl moiety, as illustrated in FIG. 7A, to reduce gastrointestinal (GI) side effects, to slow release, to lower peak concentration in favor of more stable blood levels, and to reduce the risk of accidental overdose. (Prodrugs of NSAIDS have a "more favorable therapeutic ratio of antiinflammatory and gastrointestinal erosive activities". (Venuti M C, Young J M, et al. (1989) *Pharm Res* 6:867-73)). The mirror prodrug of mefenamic acid (MFA, N-(2, 3-xylyl)anthranilic acid) links two molecules with a disulfide linker that inactivates MFA in the intestines (low pH), but dissolves in serum (high pH) to release the parent drug molecules. MFA is available in the U.S. as Ponstel (in pill form for adults) and in the U.K. as Ponstan (also as an oral suspension for children from 6 mo of age). MFA (UNII: 367589PJ2C) is a nonsteroidal anti-inflammatory drug (NSAID), but with weak COX inhibition and high potency for opening potassium channels.

The MFA prodrug can be tested against placebo in a randomized, double-blind trial. Its effect on one or more indicators or symptoms of autism or an ASD (such as development of active language) can be assessed, for example in children with early signs of autism (see Example 5).

Synthesis: Fenamates are N-phenyl-substituted anthranilic acid derivatives comprising a class of molecules based on fenamic acid (2-(phenylamino)benzoic acid. MFA can be synthesized by the copper-catalyzed condensation of o-chlorobenzoic acid and 2,3,dimethylaniline (see (Kurali (2012) CN101704761B) which describes synthesis of MFA from o-chlorobenzoic acid and 2,3,dimethylaniline (CN101704761B)).

Properties: MFA is a white to grayish-white, odorless, microcrystalline powder with a melting point of 230-231° C. with effervescence (corrected) and water solubility of 0.004% at pH 7.1. The molecular weight is 241.3 and the pKa (in water) is 4.2. (Winder C V, Wax J, et al. (1962) *J Pharmacol Exp Ther* 138:405-13)

There is a paucity of animal models of autism and ASD'. Most animal models for autism model 'syndromic' forms of autism, where a single genetic variation causes an 'autism-like' phenotype. There is a lack of animal models for idiopathic autism. Because the methods and compositions of the present invention are postulated to involve, in part, broadly reducing neuronal excitability, animal models of neuronal excitability, in general, could be drawn on as models for idiopathic forms of autism. For example, fenamates, in general, and MFA, in particular, have shown efficacy in animal models of seizures. Accordingly, in some embodiments such seizure models could be used in conjunction with the novel compositions and methods described herein.

The properties of several MFA (and related) prodrugs have been studied. In a study of several NSAID esters and thioesters (including MFA), "each prodrug retained the anti-inflammatory activity characteristic of the corresponding parent drug but exhibited moderately to greatly reduced GI erosive properties and significantly reduced analgetic potencies." (Venuti M C, Young J M, et al. (1989) *Pharm Res* 6:867-73) A separate study on an MFA prodrug confirmed the high stability. (Jilani J A, Pillai G K, et al. (1997) *Drug Dev Ind Pharm* 23:319-23)

A sustained release of MFA occurred also with two glyceride prodrugs both of which showed anti-inflammatory and analgesic activity comparable to the parent drug, with less GI irritation (Table). (Khan M S, Akhter M (2005) *Pharmazie* 60:110-4) A disulfide linked NO-donor prodrug of the structurally similar DCF (FIG. 5) had a 25% lower $C_{max}$ (15.8±0.96 vs 20.19±6.01 µg/ml) and "exhibited prolonged release of the drug", resulting in an "unaltered overall bioavailability" and "comparable AUC". While the parent drug caused severe gastric damage at 50 mg/kg and markedly more damage at 200 mg/kg, the prodrug caused neither visual nor microscopic gastric damage at 320 mg/kg (equivalent to 200 mg/kg for the parent drug). (Pathan A R, Karwa M, et al. (2010) *Inflammopharmacol* 18:157-68) In another study of MFA (Velingkar V S, Desai D M, et al. (2011) *Int J Drug Design Discovery* 2:548-58), several prodrugs were shown to be "sufficiently stable" in the GI tract, while "the amount of free drug released on hydrolysis in 80% human plasma (pH 7.4) was greater than that released in aqueous buffers". Neither prodrug caused "any significant damage, . . . toxicity [or] behavioral changes", while some had higher anti-inflammatory activity than the parent drug. (Velingkar V S, Desai D M, et al. (2011) *Int J Drug Design Discovery* 2:548-58) A DCF prodrug exhibited activity without GI ulcerogenic effect. (de Campos M L, Baldan-Cimatti H M, et al. (2012) *Drug Metab Lett* 6:235-41) Aspirin tyrosol, ibuprofen tyrosol, and indomethacin tyrosol prodrugs were less ulcerogenic than the parent NSAIDs at an equimolar dose (ulcerative index (UI)=2.6 vs 57.4, 3.5 vs 45.8, and 9.6 vs 34.4, respectively). A mutual prodrug of MFA and gabapentin was found to "be stable during their passage through the GIT until reaching blood circulation". (Mandi M F, Alsaad H N (2012) *Pharmaceuticals* (*Basel*) 5:1080-91) A mutual prodrug of MFA and APAP had a 50% lower UI than an equipotent dose of MFA alone. Two prodrugs of MFA with menthol and thymol were "chemically stable [and] biolabile" . . . and had a "better ulcer index than the parent drug". (Shah K, Shrivastava S, et al. (2013) *Med Chem Res* 22:70-7) Mutual prodrugs of MFA and 3-hydroxymethyl propyphenazon (HMP) linked with and without a spacer showed twice the half-life (16.19 and 18.69 vs 7.7 and 8.98 h) in simulated gastric fluid (pH 1.2) compared to simulated intestinal fluid (pH 7.4). The prodrugs had "less tendency (p<0.001) to form ulcer when compared to the parent drugs", i.e., 0.25 and 1.00 vs 3.17 (MFA) and 1.25 (HMP) average number of ulcers) (Ohlan S, Nanda S, et al. (2013) *Med Chem Res* 22:5120-8).

evidence of drug accumulation. In adults receiving 1 g of MFA 4× daily, steady-state concentrations of 20 μg/ml were reached on the $2^{nd}$ day, consistent with a short half-life.

Distribution: MFA has been reported as being >90% bound to albumin. (Champion G D, Graham G G (1978) *Aust N Z J Med* 8 Suppl 1:94-100) The apparent volume of

TABLE 4

Pharmacokinetic, efficacy, and GI risk parameter estimates for fenamate prodrugs from animal models

| Drug(s) | Linker | $t_{1/2}$ [h] pH 1.2 (SGF) | $t_{1/2}$ [h] pH 7.5 (SIF) | $t_{1/2}$ [h] pH 7.5 (serum/plasma) | $t_{max}$ vs MFA | $C_{max}$ vs MFA | $AUC_{4h}$ | Rat: Hint paw vs MFA | Mouse: writhing vs MFA | GI risk vs MFA | Ref. |
|---|---|---|---|---|---|---|---|---|---|---|---|
| MFA | palmityl | >28.1 | 11.5 | | 1.33 | 1.41 | "sustained release" | 106% | 93% | 33% | (Khan MS, Akhter M (2005) *Pharmazie* 60: 110-4) |
| MFA | stearyl | >33.0 | 15.6 | | 1.33 | 1.41 | "sustained release" | 108% | 92% | 50% | (Khan MS, Akhter M (2005) *Pharmazie* 60: 110-4) |
| DCF-ONO₂ | Disulfide | >>2 | >>2 | .10 | 2.00 | .78 | "comparable" | "comparable" | | 25% | (Pathan AR, Karwa M, et al. (2010) *Inflammopharmacol* 18: 157-68) |
| MFA-APAP (best results) | Without spacer (best results) | "sufficiently stable" | | "shorter than in aqueous buffers" | | | | "better" | | "no signif. Damage" | (Velingkar VS, Desai DM, et al. (2011) *Int J Drug Design Discovery* 2: 548-58: M1) |
| MFA-gabapentin | Glycol spacer | 25.1 | 8.4 | <1.00 | | | | | | | (Mandi MF, Alsaad HN (2012) *Pharmaceuticals (Basel)* 5: 1080-91: 9a) |
| MFA-APAP | SE | 79.0 | 13.6 | 1.00 | | .78 | | "comparable" | "comparable" | 50% | (Shah K, Shrivastava SK, et al. (2013) *Acta Pol Pharm* 70: 905-11) |
| MFA-menthol | SE | 20.8 | 8.9 | | | | | 115% | 115% | 50% | (Shah K, Shrivastava S, et al. (2013) *Med Chem Res* 22: 70-7) |
| MFA-thymol | SE | 23.1 | 7.1 | | | | | 125% | 150% | 60% | (Shah K, Shrivastava S, et al. (2013) *Med Chem Res* 22: 70-7) |
| MFA-PPA | With spacer | 16.2 | 7.4 | | 4.0: 3.0 | | | ≈60% @2-6 h | 61% | 10% | (Ohlan S, Nanda S, et al. (2013) *Med Chem Res* 22: 5120-8) |
| MFA-PPA | Without spacer | 18.7 | 9.0 | | 3.0: 3.0 | | | ≈60% @2-6 h | 63% | 30% | (Ohlan S, Nanda S, et al. (2013) *Med Chem Res* 22: 5120-8) |

Table 4, above provides pharmacokinetic, efficacy, and GI risk parameter estimates for fenamate prodrugs from animal models. In the table SGF refers to simulated gastric fluid; SF refers to simulated intestinal fluid; SE refers to Steglich esterification; AUC refers to area under the curve; PPA refers to propyphenazone.

Pharmacokinetics and Product Metabolism in Humans

Absorption: MFA is rapidly absorbed from the GI tract. In adults, peak levels (PL) occur after 2 h (Table 4). In two 500 mg single oral dose studies, the mean absorption was 30.5 μg/h/ml (17% CV). (Tall A R, Mistilis S P (1975) *J Int Med Res* 3:176-82) After a 1 g oral dose, plasma PL of 10-20 μg/ml (Winder C V, Kaump D H, et al. (1966) *Rheumatology* VIII: 7-49) are attained in 2-4 h. The elimination half-life is ~2 h. After multiple doses, PLs are dose proportional with no distribution ($Vz_{ss}/F$) estimated following a 500 mg oral dose of MFA was 1.06 L/kg. (Tall A R, Mistilis S P (1975) *J Int Med Res* 3:176-82)

Further oxidation to a 3-carboxy MFA (metabolite 11) may occur. (McGurk K A, Remmel R P, et al. (1996) *Drug Metab Dispos* 24:842-9) MFA and its metabolites may undergo glucuronidation. A peak PL of ≈20 μg/mL was observed at 3 h for metabolite I and its glucuronide, and a peak PL of 8 μg/ml at 6-8 h for metabolite II and its glucuronide. (Winder C V, Kaump D H, et al. (1966) *Rheumatology* VIII: 7-49)

Excretion: Approximately 52% of a MFA dose is excreted into the urine primarily as glucuronides of MFA (6%), 3-hydroxy MFA (25%) and 3-carboxy MFA (21%). The fecal route of elimination accounts for ≤20% of the dose, mainly in the form of unconjugated 3-carboxy MFA. (Winder C V, Kaump D H, et al. (1966) *Rheumatology* VIII: 7-49)

The elimination half-life of MFA is ≈2 h. Metabolites I and II appear to have longer $t_{1/2}$ than the parent compound. (Winder C V, Kaump D H, et al. (1966) *Rheumatology* VIII: 7-49) Because both renal and hepatic excretion are involved in elimination, dosage adjustments in patients with renal/hepatic dysfunction may be necessary.

Approved indications for MFA: In the U.S., MFA was approved in 1967 (NDA #015034) and is available as a prescription drug (a) for relief of mild to moderate pain in patients ≥14 yr and (b) for treatment of primary dysmenorrhea (U.S. Food and Drug Administration (2008)) in capsules of 250 and 500 mg, in generic forms and under the brand name Ponstel® (Shinogi Inc.). The recommended dose is 250-500 mg 3-4 times daily for <7 days. In the U.K., MFA is licensed as an NSAID for the symptomatic relief of

TABLE 5

Pharmacokinetic Parameter Estimates for Mefenamic Acid in Children vs Adults

| PK Parameters | Preterm Children Mean (n) | (0-5 d) $CI_{.95}$ | Preterm Children Mean (n) | (6-22 d) $CI_{.95}$ | Healthy Adults Value | (18-56 yr) CV |
|---|---|---|---|---|---|---|
| $C_{max}$ (μg/ml) | 3.8 (12) | 3.5-4.2 | 3.7 (5) | 2.9-4.5 | 10.0 | |
| $T_{max}$ (h) | 8.0 (12) | 6.8-9.2 | 6.8 (5) | 6.1-7.5 | 2.0 | 66 |
| $t_{1/2}$ (h) | 21.7 (12) | 17.9-25.4 | 11.6 (5) | 9.4-13.8 | 2-4 | N/A |
| $t_{1/2}$ (h) | 27.0 (5) | 23.7-30.9 | 8.4 (1) | N/A | 2-4 | N/A |
| % excreted (5 d) | 16.6 (5) | 12.7-20.5 | 45.7 (1) | N/A | | |

Vz/F: Apparent volume of distribution; top: Ito (1994) (Ito K, Niida Y, et al. (1994) *Acta Paediatr Jpn* 36: 387-91); bottom: Sato (1997)(Sato J, Kudo N, et al. (1997) *Biol Pharmacol Bull* 20: 443-5)

Given that MFA, its metabolites and conjugates are primarily excreted by the kidneys, the potential exists for MFA metabolites to accumulate in patients with preexisting renal disease or significantly impaired renal function. As hepatic metabolism is also a significant pathway of MFA elimination, patients with acute and chronic hepatic disease may require reduced doses.

Pediatric use: Lacking most of the above risk factors, infants tolerate NSAIDs well. GI symptoms appear to be less common than in adults and renal toxicity is rare. (Hollingworth P (1993) *Br J Rheumatol* 32:73-7) Among ≈50 case reports suggesting AEs related to MFA (Table 5) is only one child <16 years old.

Children in poor cardiac, hepatic, and/or renal health, as well as those with comorbidities requiring corticosteroids and anticoagulants will be excluded from the study proposed herein.

Availability: In the U.S., MFA is available by prescription in 250 mg capsules for oral administration. It is indicated (a) for relief of mild to moderate pain in patients ≥14 years of age, when therapy will not exceed one week (7 days) and (b) for treatment of primary dysmenorrhea.

In the U.K., MFA is licensed as an anti-inflammatory analgesic for the symptomatic relief of rheumatoid arthritis (RA), osteoarthrosis as well as pain and pyrexia. It is also licensed for primary dysmenorrhea in adolescents and menorrhagia. In addition to 250 capsules, MFA is also available as 500 mg tablets and as a 50 mg/5 ml oral suspension, which contains the following posology information: (Heads of Medicines Agencies UK (2012)): "It is recommended that children under 12 years of age should be given MFA suspension (50 mg/5 ml) in the following dosing regime: Infants over 6 months—25 mg/kg of bodyweight daily in divided doses, or, 6 months to under 2 years—one 5 ml spoonful, or 2 years to under 5 years—two 5 ml spoonfuls, or 5 years to under 9 years—three 5 ml spoonfuls, or 9 years to 12 years—four 5 ml spoonfuls. Doses may be repeated as necessary, up to three times daily. Mefenamic acid should be taken preferably with or after food."

The UK Public Assessment Report: (Heads of Medicines Agencies UK (2012)) concludes: the "overall the safety profile of [MFA] in the paediatric population does not appear to be different from adults."

rheumatoid arthritis (RA), osteoarthrosis as well as pain and pyrexia. It is also licensed for primary dysmenorrhea in adolescents and menorrhagia. MFA is available in tablets, capsules and as an oral suspension for children [6 months-12 years] to be given at a dose of 25 mg/kg of bodyweight in divided doses. Duration should be ≤7 days, except for Still's Disease (JIA). (Heads of Medicines Agencies UK (2012))

Example 5

A Clinical Trial of a Fenamate (Mefenamic Acid) Prodrug for Safeguarding Active Language Development in Children with Early Signs of Idiopathic Autism The present invention provides compositions and methods that may be useful for treating subjects showing early indicators or symptoms of autism or an ASD, or subjects that are at risk of developing autism or an ASD. In some embodiments, treatment with a fenamate, such as MFA, or a prodrug thereof, is provided. Without wishing to be bound by theory, it is hypothesized that such treatments may reduce neuronal over-excitation during critical developmental periods and, thereby, avoid withdrawal from verbal and social interactions, which, over time, could cause experience-dependent pruning in functionally related cortical regions.

Clinical trial inclusion criteria: Children aged 9-15 months showing behavioral abnormalities in a parental questionnaire confirmed in a professional evaluation. The population can be enriched with idiopathic ASD cases by requiring abnormal eye-tracking (longitudinal changes in eye fixation can be detected in children before they are diagnosed with ASD). As in the case of head circumference (Rutter M, Andersen-Wood L, et al. (1999) *J Child Psychol Psychiatry* 40:537-49) the children progressing to more severe forms of ASD are expected to have more than the 33% increase in the mouth:eyes ratio and, thus, less of an overlap with TD children. Evidence suggests that a population can be reliably enriched with children at high risk of not developing language by including children with a mouth:eyes ratio above the average mouth:eyes ratio among control children (here: 0.75) as an early prodromal sign of maladaptation. (Elison J T, Paterson S J, et al. (2013) *Am J Psychiatry* 170:899-908) and early indicator or autism or an ASD.

Clinical trial exclusion criteria: Children taking corticosteroids, anticoagulants, or APAP/NSAIDs, as well as children in poor health, including those having heart disease, hepatic and/or renal dysfunction, as judged by the admitting physician.

As the etiology may differ in children with a syndromal form of autism, children with variations in MECP2 (Rett syndrome), FMR1 (fragile X), UBE3A (Angelman syndrome), and TSC1/2 (tuberous sclerosis) can be excluded.

Dosing scheme: The approved dose of MFA for children in the age group to be studied in this trial (in the U.K.) is 25-75 mg/kg/d. The recent increase in prevalence in autism (since the 1970s), in particular the increase of more severe forms, suggests that relative minor changes in the social environment suffice to trigger the increase in neuronal hyperexcitability leading to maladaptive behavior. A MFA ester prodrug was shown to have high bioavailability, albeit with a slower pharmacokinetics. (Jilani J A, Pillai G K, et al. (1997) *Drug Dev Ind Pharm* 23:319-23) Hence, the established safe dose of 25 mg/kg/d (Heads of Medicines Agencies UK (2012)) (b.i.d.) can be used in this trial.

Route of administration: The MFA prodrug can be administered as an oral suspension.

Risk reduction: Children with known risk factors for adverse events with treatment of MFA can be excluded. To avoid nephrotoxicity, parents can be advised to take measures to prevent their children getting dehydrated while on study drug. Children can be monitored for progress in language acquisition and adverse events at 1, 3, 6, 9, and 12 months by their pediatrician.

Illustrative Clinical Trial Aims

Aim 1: Effect of MFA in Preventing Language Regression in Children with Early Signs of Non-Syndromal Autism.

Trial design/outcome: A double-blind placebo-controlled randomized clinical trial is performed. The primary outcome can be the μ-score (Morales J F, Song T, et al. (2008) *Stat Appl Genet Mol* 7:19) of (a) number of new words over the first 3 months and (b) time to formation of 'mini-sentences' (censored at 12 months of treatment). The μ-scores can be compared between active treatment and placebo group by a bivariate (Hoeffding W (1948) *Ann Math Stat* 19:293-325) Mann-Whitney (Mann H B, Whitney D R (1947) *Ann Math Stat* 18:50-60)/Gehan (Gehan E A (1965) *Biometrika* 52:203-23)-type test statistic. Randomization, sample size, early failure: To facilitate recruitment and improve the power of the secondary analysis (see Aim 2) the number of children on placebo can be reduced through a 1:3 randomization (increasing the overall size target from 160 to 210). A lack of new words over 3 months can be treated as an early failure. Compassionate use: Subjects in the control group with early failure may be offered MFA on a compassionate basis and the randomization scheme can be adjusted to include an additional control subject, while maintaining blinding for all investigators involved in treatment or evaluation. Power: Using a binomial (univariate) test as a conservative approximation, a sample size of ~200 can have 95% power to detect a reduction in risk level of 25% (e.g., from 75% to 50%) at the (two-sided) 10% level (reflecting the absence of treatment alternatives, or 90% at the conventional 5% level) after 20% attrition.

Aim 2: (Secondary): Candidate Factors for Variations in MFA Efficacy.

μGWAS can identify genetic risk factors for treatment failure in groups of <200 subjects. Hence, if the Aim 1 difference is significant at the 37% level ("null hypothesis more likely to be true than false") (Elston R C (1991) *Biometrical Journal* 33:339-45), and no adverse events have been identified, the number of children in the MFA group can be increased to 400 and screening for genetic predictors of response can be performed. To reduce time to completion, Aim 2 recruitment can be commenced immediately after completion of Aim 1 recruitment if the results fulfill the above criteria. If the Aim 1 analysis fails in the total population, but shows a preponderance of evidence in favor of MFA (see above) and/or evidence for genetic variation associated with MFA effectiveness, additional studies can be performed to determine whether a benefit is seen in some subpopulations.

Aim 3: (Secondary): Correlation of Provoked EEG Responses with MFA Efficacy.

At centers with EEG equipment, children can be offered an assessment of EEG response to exposure to pictures of familiar vs. unfamiliar faces at baseline and after two and four weeks of treatment. A sample size of 50 subjects with early symptoms of regression will have 80% power to detect a 0.2 difference in response (0.7 vs 0.5) at the conventional 5% level.

The present invention is also further described by the following claims.

The invention claimed is:

1. A method of treating a symptoms of autism in a human subject in need thereof, the method comprising administering to the subject a therapeutically effective amount of a single active agent,
    wherein the single active agent is a fenamate or an analogue thereof, and
    wherein the fenamate analogue comprises a first and second active moiety, wherein the first active moiety is a fenamate, and wherein the first and second active moieties are linked directly or are linked by a disulfide, palmityl, stearyl, glycol, polyethylene glycol, or ester linker.

2. The method of claim 1, wherein the therapeutically effective amount of the fenamate or fenamate analogue is about 15 mg/kg/day to about 100 mg/kg/day.

3. The method of claim 1, wherein the fenamate is selected from the group consisting of: fenamic acid, mefenamic acid, niflumic acid, tolfenamic acid, flufenamic acid, meclofenamic acid, and diclofenac.

4. The method of claim 1, wherein the second active moiety is a calcium channel modulator.

5. A method of treating a symptom of autism in a human subject in need thereof, the method comprising administering to the subject a composition consisting of a therapeutically effective amount of a fenamate or an analogue thereof and an effective amount of a calcium channel modulator, wherein the fenamate analogue comprises a first and second active moiety, wherein the first active moiety is a fenamate, and wherein the first and second active moieties are linked directly or are linked by a disulfide, palmityl, stearyl, glycol, polyethylene glycol, or ester linker.

6. The method of claim 5, wherein the calcium channel modulator is gabapentin, pregabalin, or atagabalin.

7. The method of claim 1, wherein the method comprises administering to the subject a therapeutically effective amount of a single active agent, wherein the single active agent is mefenamic acid or a mefenamic acid analogue, wherein the mefenamic acid analogue comprises a first and second active moiety, wherein the first active moiety is mefenamic acid, wherein the second active moiety is gabapentin, and wherein the first and second active moieties are linked directly or are linked by a disulfide, palmityl, stearyl, glycol, polyethylene glycol, or ester linker.

8. The method of claim 1, wherein the human subject is less than 36 months in age.

9. The method of claim 1, wherein the fenamate analogue has a structure:

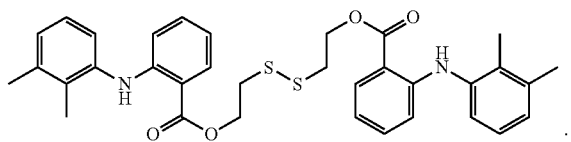

10. The method of claim 5, wherein the fenamate is selected from the group consisting of: fenamic acid, mefenamic acid, niflumic acid, tolfenamic acid, flufenamic acid, and diclofenac.

11. The method of claim 1, wherein the therapeutically effective amount of the fenamate or fenamate analogue is about 15 mg/kg/day to about 100 mg/kg/day and wherein the human subject is less than 36 months in age.

12. A method of treating a symptom of autism in a human subject in need thereof, the method comprising administering to the subject a
   a pharmaceutically effective amount of a single active agent
   wherein the single active agent is a fenamate,
   wherein the fenamate analogue comprises a first and second active moiety, wherein the first active moiety is a fenamate, and wherein the first and second active moieties are linked directly or are linked by a disulfide, palmityl, stearyl, glycol, polyethylene glycol, or ester linker,
   wherein the subject is a child aged 9 to 36 months of age, and
   wherein the single active agent is administered at a dose of from 15 mg/kg/day to 100 mg/kg/day.

13. The method of claim 12, wherein the fenamate is mefenamic acid.

14. The method of claim 12, wherein the symptom of autism is nonverbal communication.

15. The method of claim 1, wherein the fenamate is mefenamic acid.

16. The method of claim 1, wherein the symptom of autism is nonverbal communication.

17. The method of claim 5, wherein the fenamate is mefenamic acid.

18. The method of claim 5, wherein the symptom of autism is nonverbal communication.

19. The method of claim 5, wherein the therapeutically effective amount of the fenamate or fenamate analogue is about 15 mg/kg/day to about 100 mg/kg/day.

20. The method of claim 5, wherein the human subject is less than 36 months in age.

* * * * *